(12) United States Patent
Hopkins et al.

(10) Patent No.: US 11,051,812 B2
(45) Date of Patent: Jul. 6, 2021

(54) SURGICAL STAPLER WITH PARTIAL POCKETS

(71) Applicant: Applied Medical Resources Corporation, Rancho Santa Margarita, CA (US)

(72) Inventors: Timothy M. Hopkins, Rancho Santa Margarita, CA (US); Donald L. Gadberry, Capistrano Beach, CA (US); Matthew M. Becerra, Lake Forest, CA (US); Babak Jasemian, Trabuco Canyon, CA (US); Gary M. Johnson, Rancho Santa Margarita, CA (US); Steven E. Decker, Anaheim, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 474 days.

(21) Appl. No.: 15/847,575

(22) Filed: Dec. 19, 2017

(65) Prior Publication Data

US 2018/0103951 A1   Apr. 19, 2018

Related U.S. Application Data

(63) Continuation of application No. 14/212,357, filed on Mar. 14, 2014, now Pat. No. 9,872,683.

(Continued)

(51) Int. Cl.
*A61B 17/072* (2006.01)
*A61B 17/064* (2006.01)

(52) U.S. Cl.
CPC .... *A61B 17/07207* (2013.01); *A61B 17/0644* (2013.01); *A61B 2017/0641* (2013.01);

(Continued)

(58) Field of Classification Search
None
See application file for complete search history.

(56) References Cited

U.S. PATENT DOCUMENTS

| 2,073,960 | A | 3/1937 | Crosby |
| 2,140,593 | A | 12/1938 | Pankonin |

(Continued)

FOREIGN PATENT DOCUMENTS

| EP | 0 251 444 A1 | 1/1988 |
| EP | 0 492 283 A1 | 7/1992 |

(Continued)

OTHER PUBLICATIONS

Definition of "Either" by Merriam-Webster. Retrieved from URL https://www.merriam-webster.com/dictionary/either on Jun. 12, 2020 (Year: 2020).*

(Continued)

*Primary Examiner* — Valentin Neacsu
(74) *Attorney, Agent, or Firm* — John F. Heal

(57) ABSTRACT

A surgical stapler includes a jaw assembly at a distal end connected to a handle assembly that is configured to control the stapler and actuate the deployment of staples. The surgical stapler successfully eliminates intermediate caming portions commonly known as pushers that are located between the staples and a translating slider. The staples are located in pockets at an angle such that the base of the staple is parallel to an angled caming surface of the slider. The translating slider comes into direct contact with staples during deployment as the slider moves through each staple pocket where staples are partially supported by recesses along the slider pathway. The staples are deployed at an angle against the anvil surface. Because there are no pushers, a great deal of space is saved resulting in a much smaller (Continued)

diameter surgical stapler that is particularly suitable for laparoscopic stapling applications.

4 Claims, 41 Drawing Sheets

Related U.S. Application Data

(60) Provisional application No. 61/785,100, filed on Mar. 14, 2013.

(52) U.S. Cl.
CPC .............. *A61B 2017/07221* (2013.01); *A61B 2017/07228* (2013.01); *A61B 2017/07264* (2013.01); *A61B 2017/07278* (2013.01); *A61B 2017/07285* (2013.01)

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A * | 11/1994 | Kerrigan .............. B25C 5/0257 29/505 |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A * | 1/1996 | Blewett .............. A61B 17/072 227/175.1 |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,285 A * | 11/1996 | Chow .............. A61B 17/0644 606/219 |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |

(56) References Cited

U.S. PATENT DOCUMENTS

| | | |
|---|---|---|
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A * | 4/2000 | Green ............ A61B 17/115 227/179.1 |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 * | 10/2005 | Dworak ............ B21D 13/02 227/154 |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |

(56) References Cited

U.S. PATENT DOCUMENTS

| | | |
|---|---|---|
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,531 B1 * | 2/2011 | Ward .............. A61B 17/07207 227/156 |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,415 B2 * | 7/2012 | Ward .............. A61B 17/07207 227/175.1 |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |

(56) References Cited

U.S. PATENT DOCUMENTS

| | | |
|---|---|---|
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,328,063 B2 * | 12/2012 | Milliman ............ A61B 17/1114 227/175.1 |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |

(56) References Cited

U.S. PATENT DOCUMENTS

| | | |
|---|---|---|
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0180634 A1 | 8/2006 | Shelton, IV et al. |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1* | 3/2007 | Whitman ............. A61B 17/068 227/155 |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton |
| 2008/0029575 A1 | 2/2008 | Shelton |
| 2008/0041918 A1* | 2/2008 | Holsten ................... A61B 17/11 227/180.1 |
| 2008/0078807 A1* | 4/2008 | Hess ................... A61B 17/0644 227/181.1 |
| 2008/0105730 A1* | 5/2008 | Racenet ............... A61B 17/068 227/176.1 |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1* | 11/2009 | Beardsley ......... A61B 17/0644 227/178.1 |
| 2009/0277949 A1* | 11/2009 | Viola ................... A61B 17/072 227/178.1 |
| 2010/0069942 A1 | 3/2010 | Shelton, IV |
| 2010/0072258 A1* | 3/2010 | Farascioni ........ A61B 17/07207 227/180.1 |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1* | 2/2011 | Holsten ............... A61B 17/1114 227/176.1 |
| 2011/0087276 A1 | 4/2011 | Bedi et al. |
| 2011/0101067 A1* | 5/2011 | Johnson ............ A61B 17/07207 227/176.1 |
| 2011/0108601 A1* | 5/2011 | Clark ..................... B25C 3/006 227/119 |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1* | 6/2011 | Ward ............... A61B 17/07207 206/339 |
| 2011/0139852 A1 | 6/2011 | Zingman |
| 2011/0147433 A1 | 6/2011 | Shelton, IV et al. |
| 2011/0155787 A1 | 6/2011 | Baxter, III et al. |
| 2011/0290853 A1* | 12/2011 | Shelton, IV ..... A61B 17/07207 227/177.1 |
| 2012/0012640 A1* | 1/2012 | Racenet ............... A61B 17/068 227/177.1 |
| 2012/0018326 A1* | 1/2012 | Racenet ............ A61B 17/07207 206/339 |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1* | 4/2012 | Shelton, IV ..... A61B 17/00491 227/178.1 |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0211542 A1 | 8/2012 | Racenet |
| 2012/0286022 A1 | 11/2012 | Olson et al. |
| 2012/0318844 A1* | 12/2012 | Shelton, IV ........... A61B 90/92 227/176.1 |
| 2012/0325893 A1* | 12/2012 | Pastorelli ............ A61B 17/072 227/177.1 |
| 2013/0001270 A1 | 1/2013 | Kostrzewski |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |

(56) References Cited

U.S. PATENT DOCUMENTS

| | | |
|---|---|---|
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0183948 A1 | 6/2016 | Shelton, IV et al. |
| 2016/0262759 A1* | 9/2016 | Johnson ............ A61B 17/07207 |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 263 568 A2 | 12/2010 |
| EP | 2 361 562 A1 | 8/2011 |
| EP | 2 486 859 A2 | 8/2012 |
| EP | 2 772 192 A1 | 9/2014 |
| EP | 2 777 530 A1 | 9/2014 |
| EP | 2 923 661 A2 | 3/2015 |
| EP | 2 926 742 A1 | 10/2015 |
| EP | 3 238 639 A2 | 3/2017 |
| JP | 2001-087272 A | 4/2001 |
| RU | 2063710 | 7/1996 |
| WO | WO 83/02247 A1 | 7/1983 |
| WO | WO 02/30296 A2 | 4/2002 |
| WO | WO 02/096327 A2 | 12/2002 |
| WO | WO 2003/094747 A1 | 11/2003 |
| WO | WO 2004/032762 | 4/2004 |
| WO | WO 2012/052729 A1 | 4/2012 |
| WO | WO 2014/139440 A1 | 9/2014 |

OTHER PUBLICATIONS

International Searching Authority/ EPO, Invitation to Pay Additional Fees and Communication Relating to the Results of the Partial

(56) References Cited

OTHER PUBLICATIONS

International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, European Search Report for European Application No. 07784007.2, entitled "Surgical Stapler," dated Jun. 15, 2012, 6 pgs.
Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
International Searching Authority, U.S., The International Search Report and the Written Opinion of the International Searching authority for international application PCT/US2014/027768, titled "Surgical Stapler with Expandable Jaw", dated Jul. 25, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
European Patent Office, International Search Report and Written Opinion for International Application No. PCT/US2014/028211, titled Surgical Stapler with Partial Pockets dated Sep. 8, 2014.
The International Bureau of WIPO, International Preliminary Report on Patentability, dated Sep. 24, 2015, for International Application No. PCT/US2014/028211.

\* cited by examiner

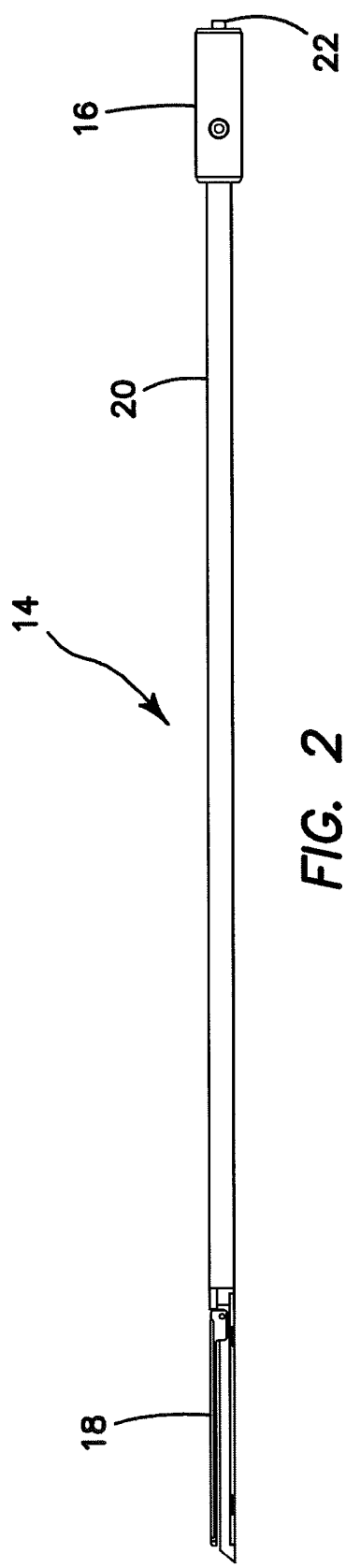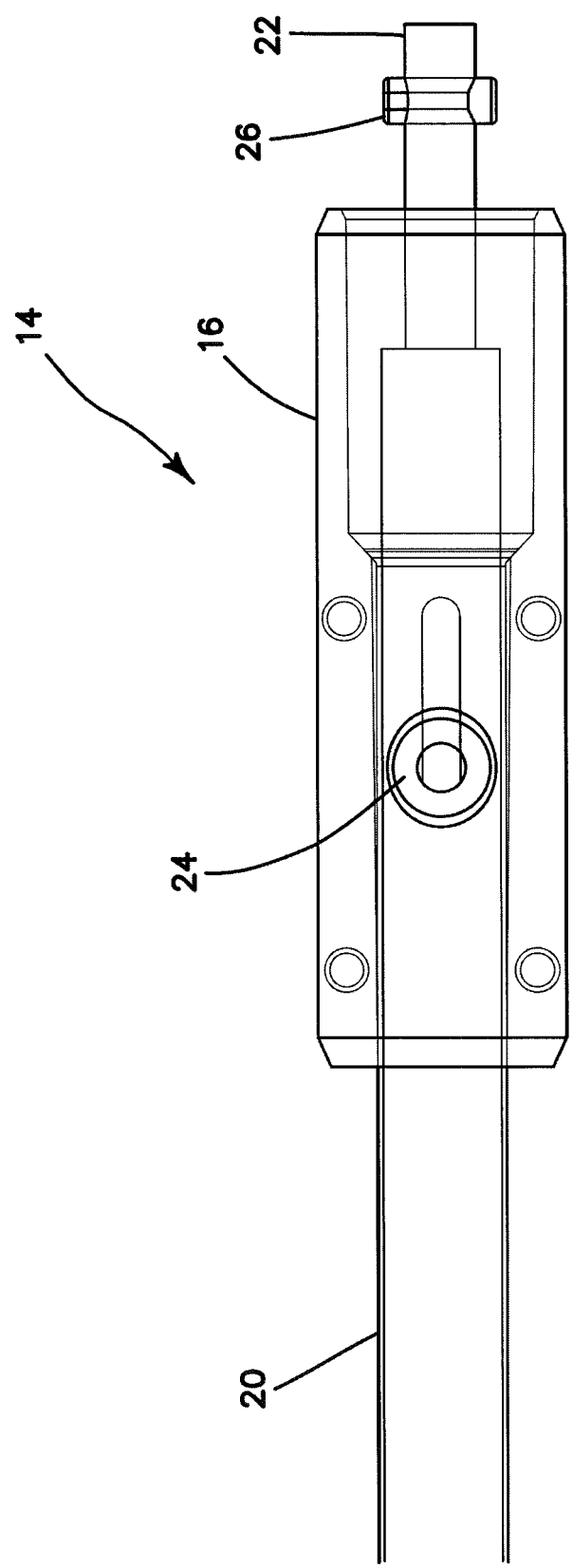

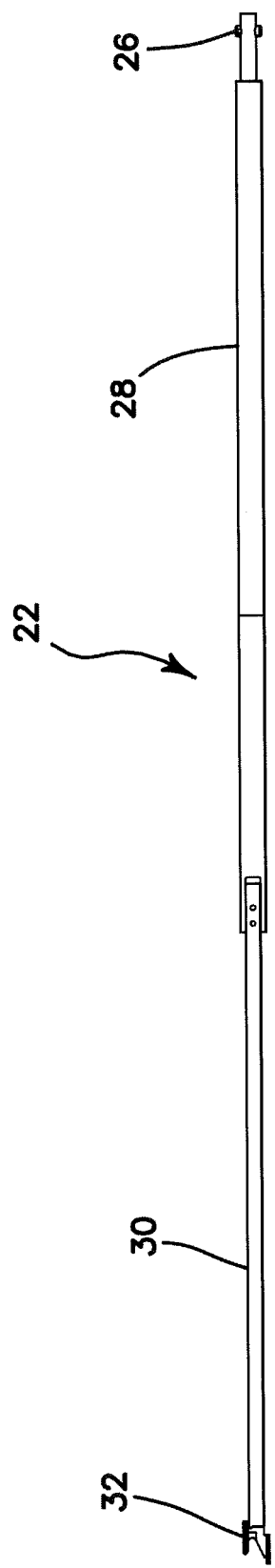
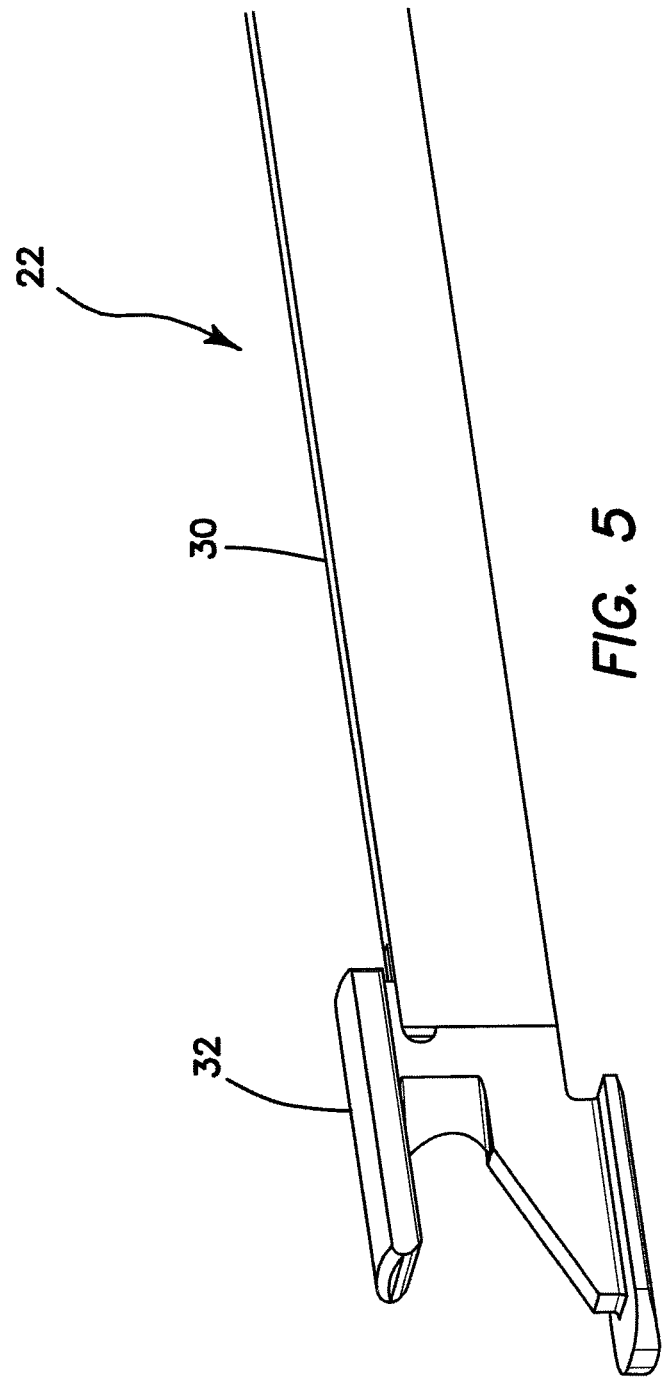

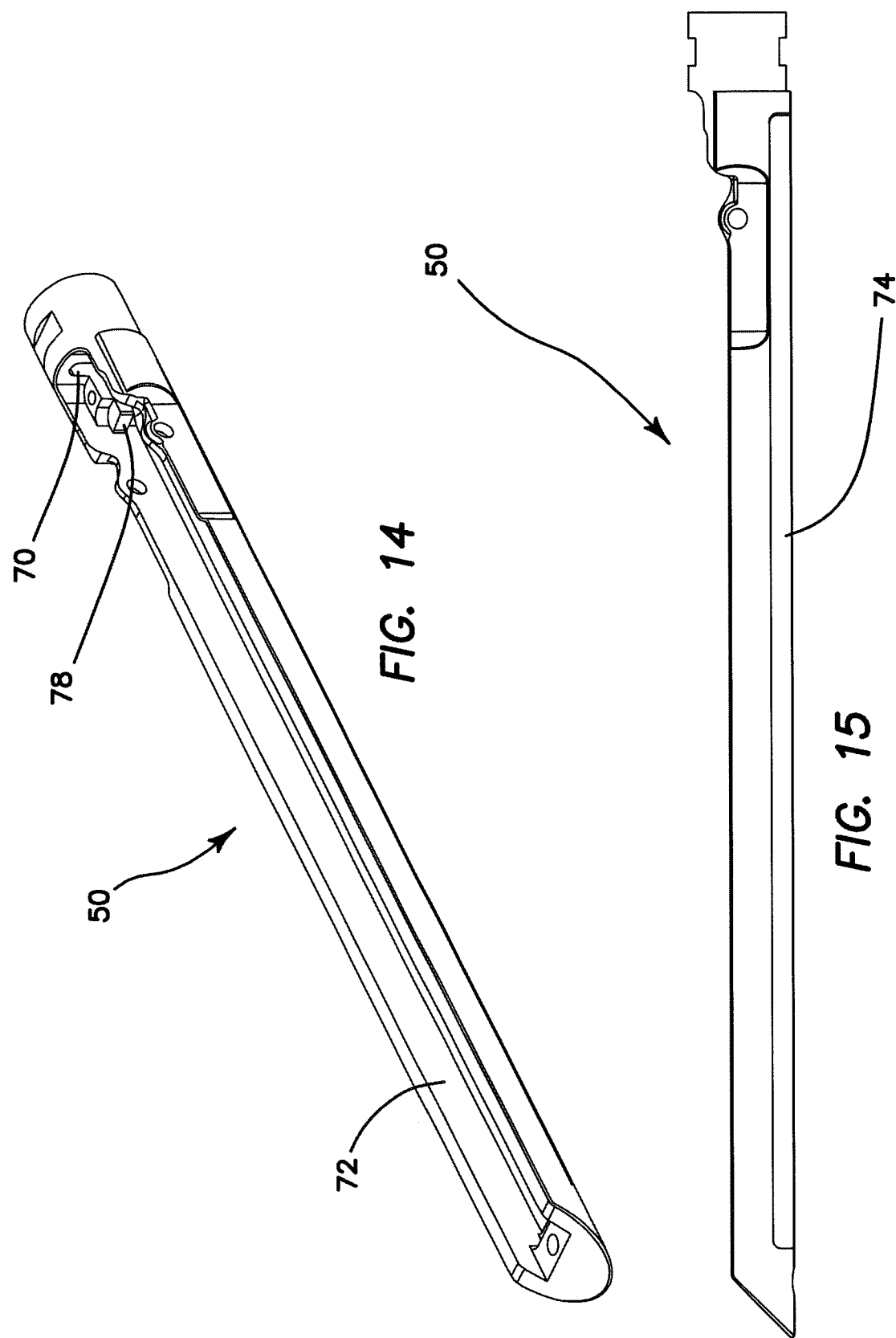

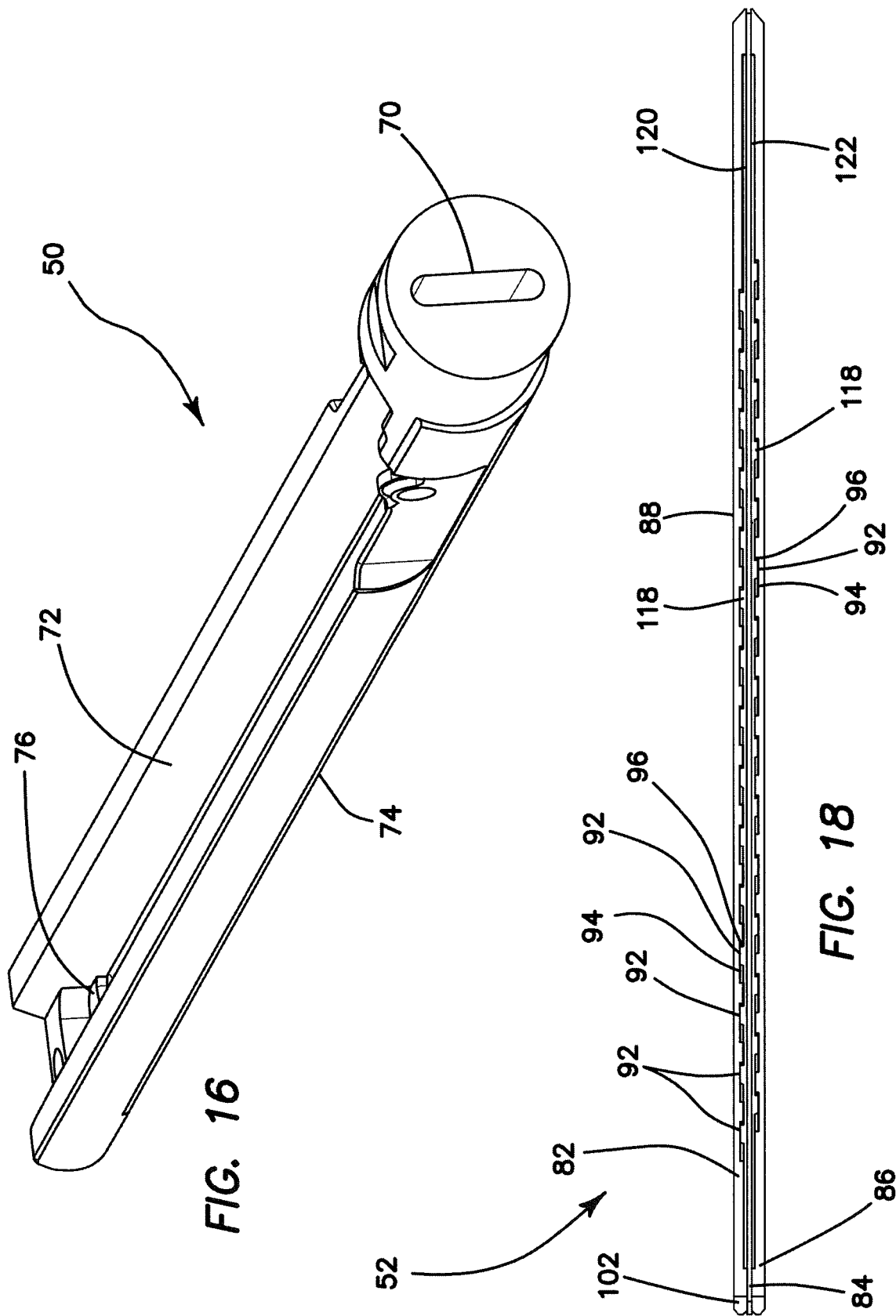

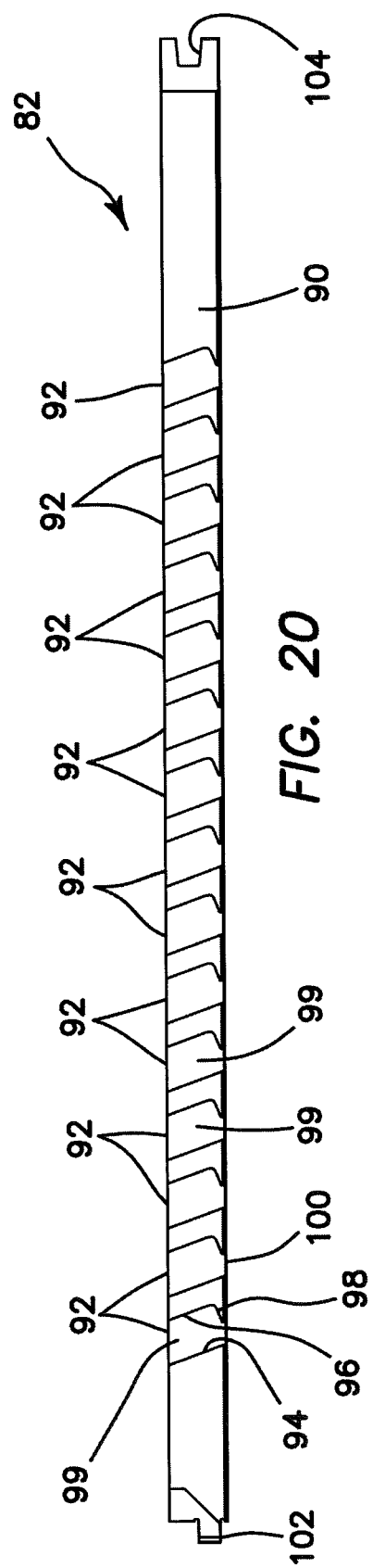
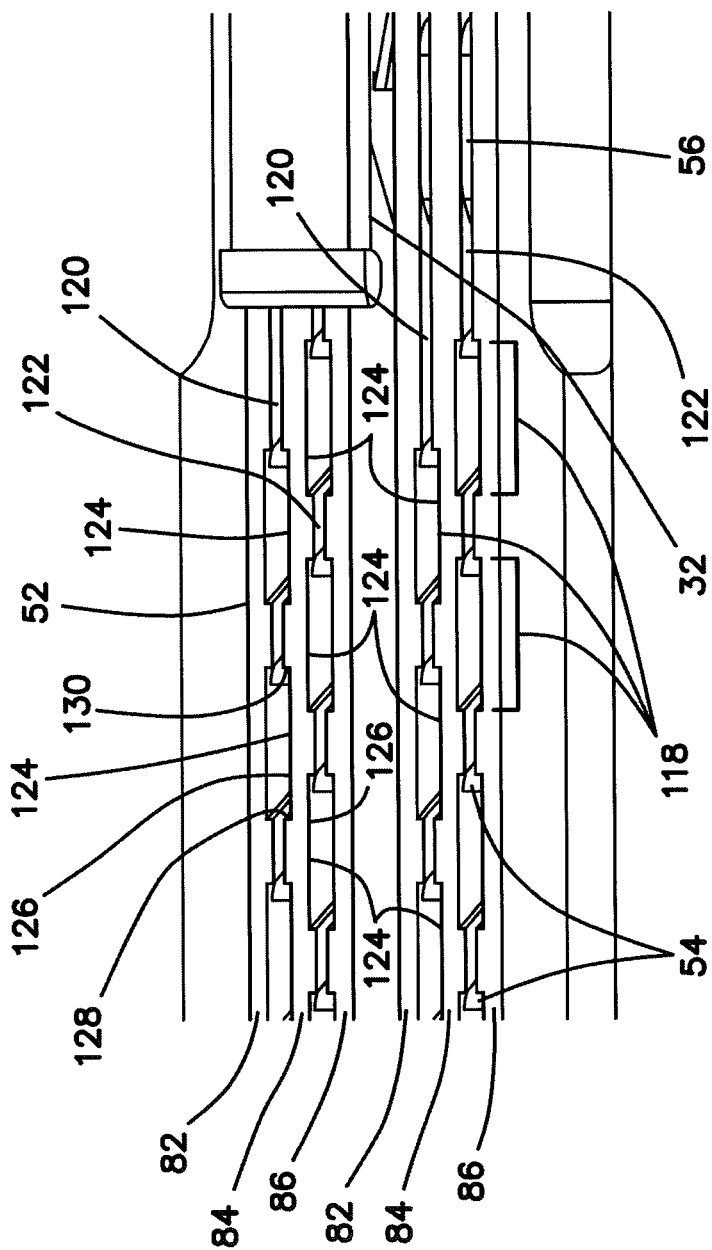

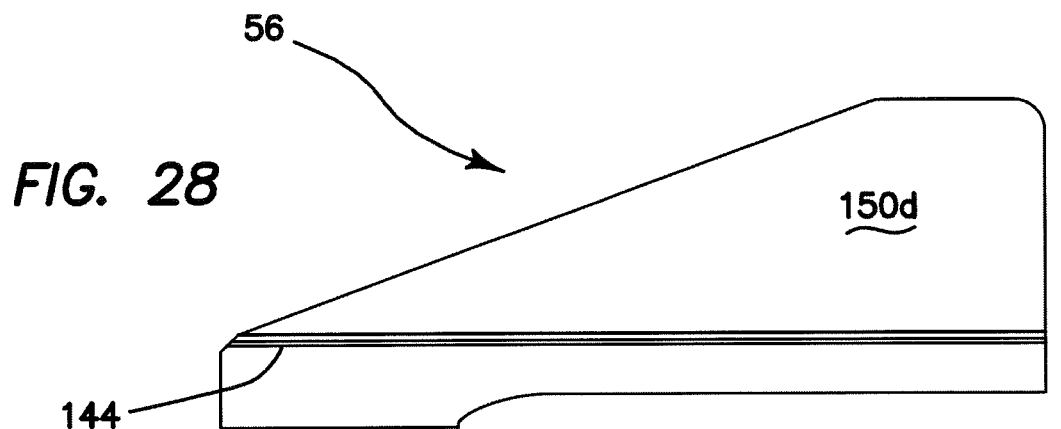
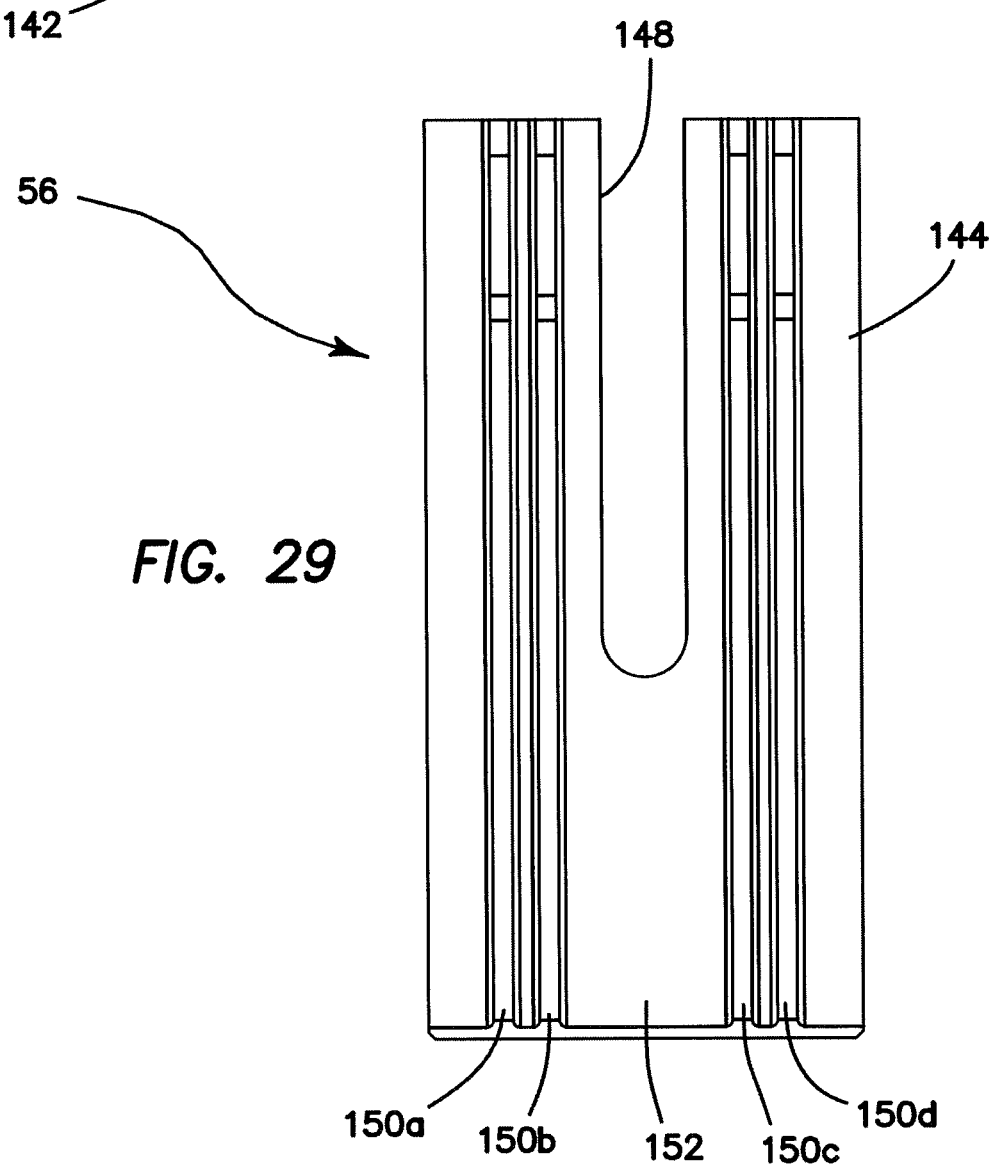

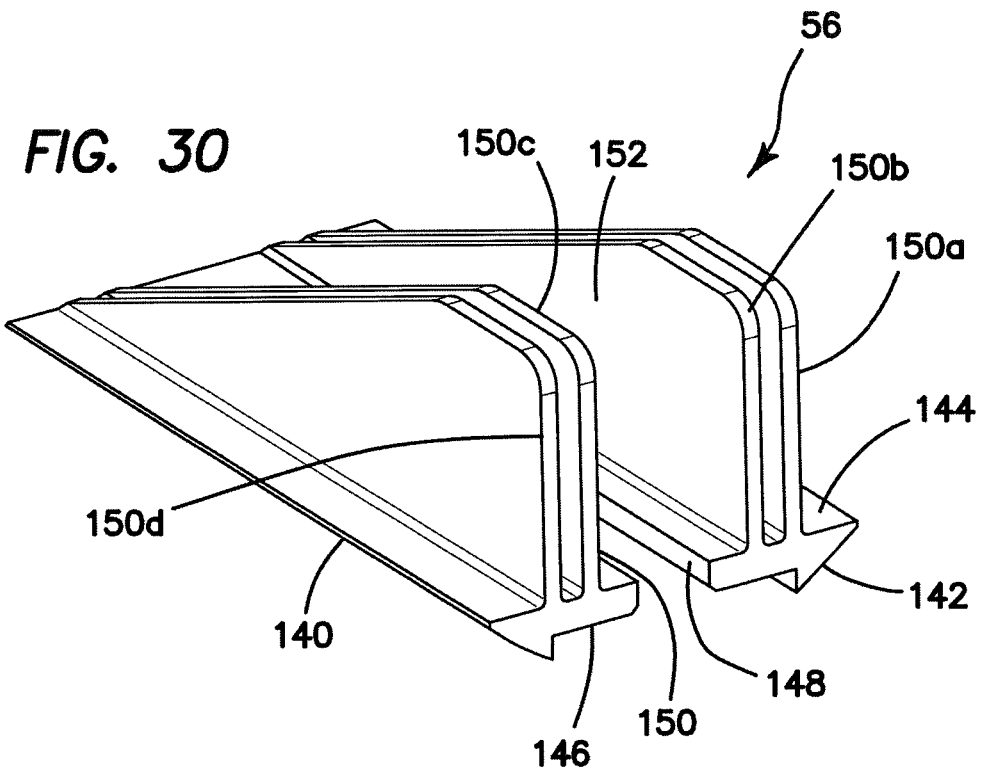
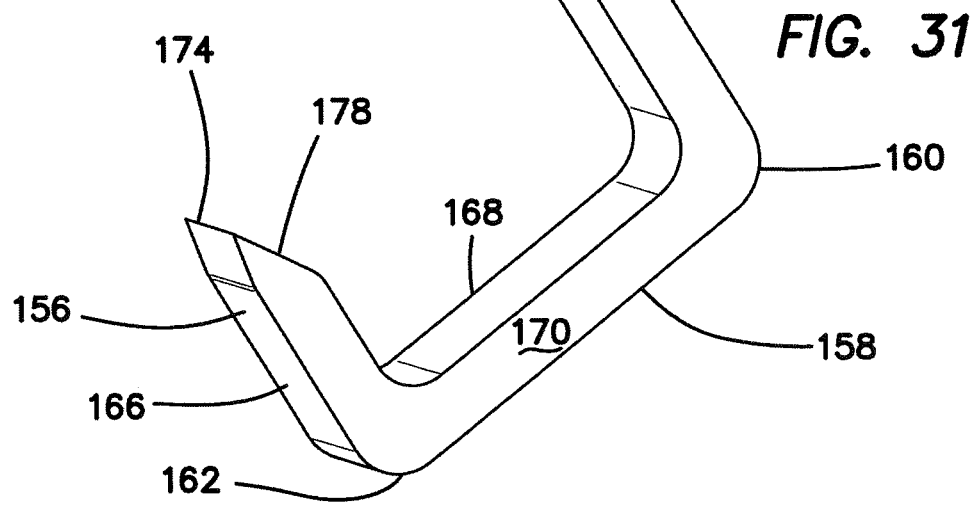

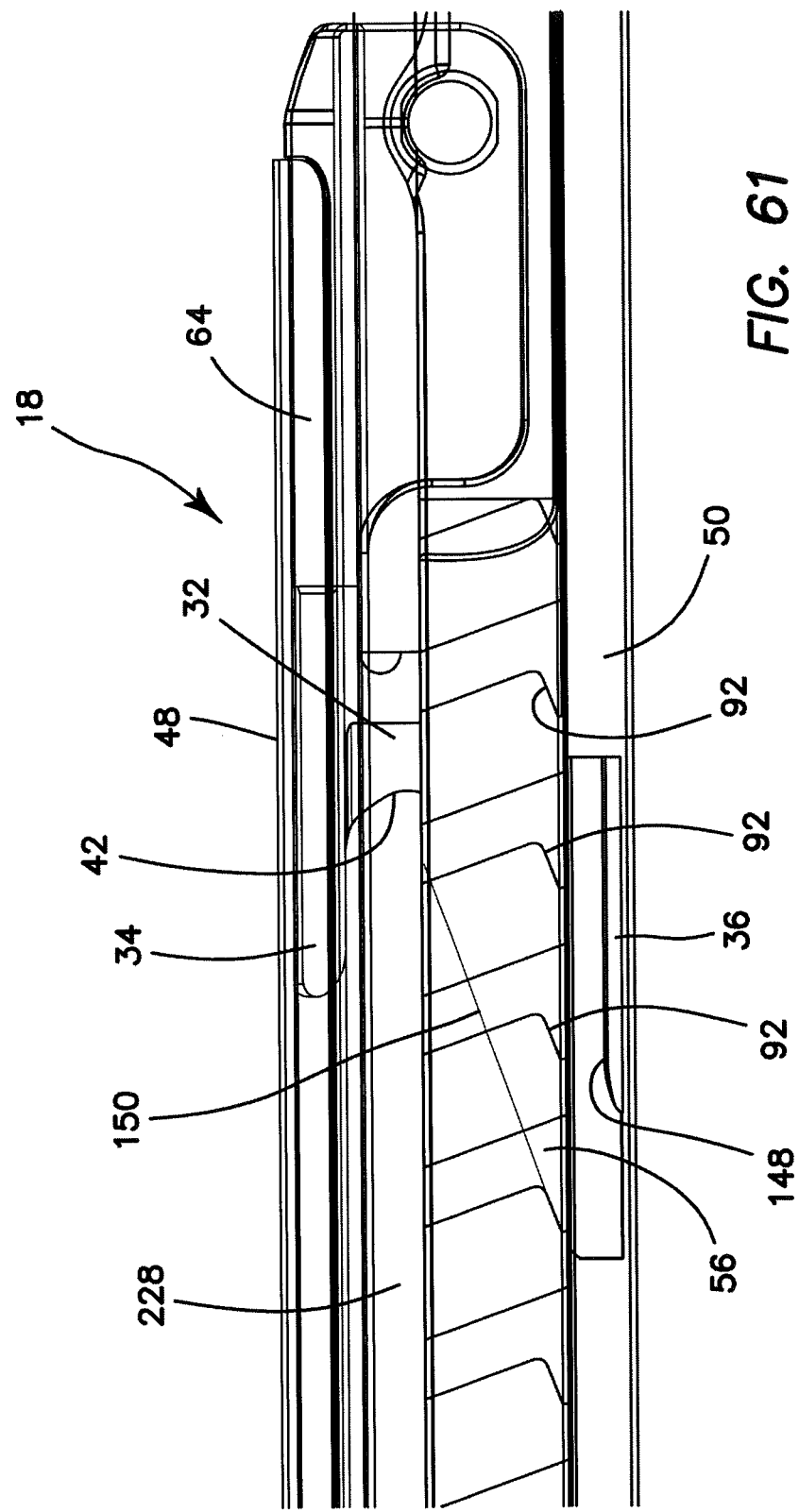

SURGICAL STAPLER WITH PARTIAL POCKETS

CROSS-REFERENCE TO RELATED APPLICATIONS

This application is a continuation of U.S. application Ser. No. 14/212,357, filed Mar. 14, 2014 entitled "Surgical stapler with partial pockets," which claims the benefit of U.S. Provisional Patent Application Ser. No. 61/785,100 filed on Mar. 14, 2013 entitled "Surgical stapler with partial pockets" which are incorporated herein by reference in their entirety.

FIELD

This disclosure relates to surgical instruments, and more particularly, to surgical stapling instruments and staples for sequentially applying a plurality of surgical staples to body tissue.

BACKGROUND

A typical surgical stapler apparatus comprises a handle at a proximal end and two elongated jaw-like members joined together at a hinge at a distal end. The jaw-like members articulate to open and close to capture tissue between the jaw-like members. The user controls the device from the handle to open and close the jaw-like members, actuate deployment of staples and in general manipulate and control the device. One of the jaw members carries a disposable cartridge containing staples arranged in two or more rows. The other one of the jaw-like members comprises an anvil against which the staples are driven to deform the staple legs. Staples are driven out of the cartridge by a caming surface or slider that moves longitudinally against a plurality of laterally positioned pushers that push each staple out of the cartridge individually. The caming surface of the slider is angled to complement the angular surface of the pushers. The cooperation between the angular surfaces of the pushers and the slider is a key step of the surgical stapling process. Misalignment can cause the staples to jam the device. Some staplers include a blade that follows the caming surface so as to cut the tissue between the two or more rows of delivered staples.

Surgical staplers are used in a variety of surgical techniques including laparoscopic and/or endoscopic or other minimally invasive surgical procedures in which the stapler is inserted through a cannula or tube positioned within a small incision in a patient's body. In laparoscopic, endoscopic or minimally invasive surgery, a trocar or cannula is inserted across body tissue of a patient to access a body cavity and to create a channel for the insertion of a camera, such as a laparoscope. The camera provides a live video feed capturing images that are then displayed to the surgeon on one or more monitors. Additional trocars are inserted to create additional pathways through which surgical instruments, including surgical staplers, can be inserted for performing procedures observed on the monitor. The targeted tissue location such as the abdomen is typically enlarged by delivering carbon dioxide gas to insufflate the body cavity and create a working space large enough to accommodate the scope and instruments used by the surgeon. The insufflation pressure in the tissue cavity is maintained by using specialized trocars having seals that prevent the insufflation gas from escaping and collapsing the surgical working space. Laparoscopic surgery offers a number of advantages when compared with an open procedure. These advantages include reduced pain and hemorrhaging and shorter recovery times.

As laparoscopic surgery evolves to become even more minimally invasive with incisions and cannula diameters becoming smaller and smaller, surgical staplers for use in laparoscopic/endoscopic procedures must be designed to fit within the small lumen of a cannula. Generally, a surgical stapler is inserted into a cannula such that the jaw-like members are in a closed orientation to inside the patient where the jaw-like members are opened to grasp and staple tissue. The handle of the stapler resides outside of the patient in control of the surgeon user. A portion of the shaft of the stapler between the jaw-like members and the handle is long enough to extend from outside the patient to inside the patient. During the surgical procedure, the elongate shaft of the stapler resides inside the cannula into which it was inserted. The distal jaw-like members include many components such as an anvil for forming staples, a staple cartridge with a plurality of staples, a caming surface such as a slider, pushers, a blade and other components which must all be small enough to fit through a small diameter cannula and made to function reliably and repeatedly from outside the patient. While conventional laparoscopic staplers are approximately 12 millimeters in diameter, the present invention provides a surgical stapler designed to fit inside a cannula having a diameter as small as approximately 5-10 mm.

SUMMARY

According to one aspect of the invention, a surgical stapler is provided. The surgical stapler includes a handle assembly and a cartridge assembly removably connected to the handle assembly. The cartridge assembly has a proximal end and a distal end and includes a jaw assembly at the distal end. The jaw assembly includes a first jaw and a second jaw. The first jaw has an anvil surface and the second jaw has a top surface. The second jaw is movable relative to the first jaw and the jaw assembly includes a closed position in which the anvil surface is adjacent to a top surface and a gap is defined between the top surface and the anvil surface. The second jaw includes a first surface and a second surface substantially parallel to each other and perpendicular to the top surface. The first surface and second surface defines a first slot between the first surface and the second surface extending along a length of the second jaw. The first slot has a slot width. The first surface includes a plurality of recesses formed into the first surface. Each recess includes a recessed wall, a front sidewall, and a rear sidewall. The second jaw includes a plurality of staple pockets. Each staple pocket is defined by the recessed wall, front sidewall, rear sidewall, a bottom wall, second surface and an opening to the top surface of the second jaw. The bottom wall is formed as part of the first surface, second surface or other surface. An actuator is coupled to the handle assembly. The cartridge assembly includes a first caming surface having a thickness. The first caming surface is movable by the actuator within the first slot and along a length of the second jaw. A plurality of staples is positioned in the plurality of staple pockets. Each staple has a staple width and is positioned within a pocket such that a portion of the staple width resides within the first slot and a portion of the staple width is located and supported by the recess in the first surface. The bottom wall is formed as part of the first surface, second surface or other surface and configured such that the first caming surface contacts a portion of the staple. With translation of the first caming surface within the first slot, the first caming surface passes through one or more staple pockets making contact with that portion of the staple width resident within the first slot to urge the staple out of the opening and against the anvil surface.

According to another aspect of the invention, a surgical stapler is provided. The surgical stapler includes a handle assembly and a cartridge assembly removably connected to the handle assembly. The cartridge assembly includes a proximal end and a distal end. A jaw assembly is located at the distal end of the cartridge assembly. The jaw assembly has a longitudinal axis and includes a first jaw connected to a second jaw. The first jaw includes an anvil surface that is a smooth and flat without any staple-forming pockets. The second jaw has a top surface. The second jaw is movable relative to the first jaw such that the jaw assembly includes a closed position in which the anvil surface is adjacent to a top surface and a gap is defined between the top surface and the anvil surface. The second jaw includes a plurality of staple pockets. Each staple pocket has a longitudinal axis and an opening at the top surface. An actuator is coupled to the handle assembly. At least one caming surface is movable by the actuator within the second jaw and along a length of the second jaw. A plurality of staples is positioned inside the staple pockets. Each staple includes at least a first leg and a second leg interconnected by base and an open configuration for penetrating tissue and a closed configuration for retaining tissue. The plurality of staples is located inside the staple pockets in an open configuration. With the jaw assembly in a closed position, translation of the caming surface along the second jaw ejects the staples from the staple pockets toward the anvil surface of the first jaw to deform the staples from an open configuration against the anvil surface to a closed configuration.

According to another aspect of the invention, a surgical stapler is provided. The surgical stapler includes a handle assembly and a cartridge assembly removably connected to the handle assembly. The cartridge assembly includes a proximal end and a distal end. A jaw assembly is located at the distal end of the cartridge assembly. The jaw assembly has a longitudinal axis and includes a first jaw connected to a second jaw. The first jaw includes an anvil surface that is a smooth and flat without any staple-forming pockets. The second jaw has a top surface. The second jaw is movable relative to the first jaw such that the jaw assembly includes a closed position in which the anvil surface is adjacent to a top surface and a gap is defined between the top surface and the anvil surface. The second jaw includes a plurality of staple pockets. Each staple pocket has a longitudinal axis and an opening at the top surface. An actuator is coupled to the handle assembly. At least one caming surface is movable by the actuator within the second jaw and along a length of the second jaw. A plurality of staples is positioned inside the staple pockets. Each staple includes an open configuration for penetrating tissue and a closed configuration for retaining tissue. The plurality of staples is located inside the staple pockets in an open configuration. With the jaw assembly in a closed position, translation of the caming surface along the second jaw ejects the staples from the staple pockets toward the anvil surface of the first jaw to deform the staples from an open configuration against the anvil surface to a closed configuration.

According to another aspect of the invention, a surgical stapler is provided. The surgical stapler includes a handle assembly and a cartridge assembly removably connected to the handle assembly. The cartridge assembly includes a proximal end and a distal end and a jaw assembly at the distal end. The jaw assembly has a longitudinal axis and includes a first jaw connected to a second jaw. The first jaw has an anvil surface and the second jaw has a top surface. The second jaw is movable relative to the first jaw such that the jaw assembly includes a closed position in which the anvil surface is adjacent to a top surface defining a gap between the top surface and the anvil surface. The second jaw includes a plurality of staple pockets having a plurality of openings at the top surface. The staple pockets are arranged in at least three substantially parallel rows along the top surface of the second jaw. The stapler includes an actuator coupled to the handle assembly and at least one caming surface movable by the actuator along a length of the second jaw. A blade is provided and configured to be movable within the gap defined between the top surface and the anvil surface when the first jaw and second jaw are in the closed position. The blade is configured to sever tissue located between the first jaw and the second jaw defining a cutting line. A plurality of staples is positioned inside the plurality of staple pockets. The caming surface is configured to eject staples from the staple pockets and against the anvil surface to deform the staples with translation of the caming surface along the second jaw. The second jaw includes a number of rows of staple pockets on one side of the blade that is different from a number of rows of staple pockets on the other side of the blade cutting line.

According to another aspect of the invention, a surgical stapler is provided. The surgical stapler includes a handle assembly removably connected to a cartridge assembly. The cartridge assembly includes a jaw assembly at the distal end. The jaw assembly has a longitudinal axis and includes a first jaw connected to a second jaw. The first jaw has a longitudinal axis and an anvil surface. The anvil surface includes a series of parallel channels. Each channel has a length and a surface that may be any shape, semi-cylindrical, curved, concave, square, or rectangle and configured for assisting in closing the staple in the desired direction. The lengths of the channels are perpendicular to the longitudinal axis of the jaw assembly. The second jaw has a top surface and is movable relative to the first jaw. The jaw assembly has a closed position in which the anvil surface is adjacent to a top surface and a gap is defined between the top surface and the anvil surface. The second jaw includes a plurality of staple pockets. Each staple pocket has an opening at the top surface. An actuator coupled to the handle assembly is provided. The stapler includes at least one caming surface movable by the actuator within the second jaw and along a length of the second jaw. A blade is provided and configured to be movable within the gap defined between the top surface and the anvil surface when the first jaw and second jaw are in the closed position. The blade is configured to sever tissue located between the first jaw and the second jaw defining a cutting line. A plurality of staples is positioned inside the staple pockets. Each staple includes an open configuration for penetrating tissue and a closed configuration for retaining tissue. The plurality of staples is located inside the staple pockets in an open configuration. The channels extend across the anvil surface on either side of the cutting line. With the jaw assembly in a closed position, translation of the caming surface along the second jaw ejects the staples from the staple pockets toward the anvil surface of the first jaw to deform the staples from an open configuration against the anvil surface to a closed configuration. The channels are configured to permit the formation of staples into a closed configuration.

According to another aspect of the invention, a surgical stapler is provided. The surgical stapler includes a handle assembly removably connected to a cartridge assembly. The cartridge assembly has a proximal end and a distal end and a jaw assembly located at the distal end. The jaw assembly has a longitudinal axis and includes a first jaw connected to a second jaw. The first jaw has a longitudinal axis and an anvil surface. The anvil surface includes a series of parallel channels. Each channel has a length and a surface that may be any shape, curved, concave, semi-cylindrical, square, or rectangle and configured for assisting in closing the staple in the desired direction. The length of each channel is parallel to the longitudinal axis of the jaw assembly and extends along the anvil surface. The second jaw has a top surface. The second jaw is movable relative to the first jaw. The jaw assembly includes a closed position in which the anvil surface is adjacent to a top surface and a gap is defined between the top surface and the anvil surface. The second jaw includes a plurality of staple pockets having a plurality of openings at the top surface. The staple pockets are arranged in parallel rows along the top surface of the second jaw. An actuator is included and coupled to the handle assembly. At least one caming surface is movable by the actuator within the second jaw and along a length of the second jaw. The surgical stapler further includes a plurality of staples positioned inside the staple pockets. Each staple includes an open configuration for penetrating tissue and a closed configuration for retaining tissue. The plurality of staples is located inside the staple pockets in an open configuration. With the jaw assembly in a closed position, translation of the caming surface along the second jaw ejects the staples from the staple pockets toward the anvil surface of the first jaw to deform the staples from an open configuration against the anvil surface to a closed configuration. The channels are configured to permit the formation of staples into a closed configuration.

According to another aspect of the invention, a surgical stapler is provided. The surgical stapler includes a handle assembly removably connected to a cartridge assembly. The cartridge assembly has a proximal end and a distal end and includes a jaw assembly at the distal end. The jaw assembly includes a first jaw connected to a second jaw. The first jaw has an anvil surface and the second jaw has a top surface. The first jaw is connected to the second jaw such that the second jaw is movable relative to the first jaw. The jaw assembly includes a closed position in which the anvil surface is adjacent to a top surface and a gap is defined between the top surface and the anvil surface. The second jaw includes a first surface and a second surface substantially parallel to each other and perpendicular to the top surface. The first surface includes a plurality of recesses formed into the first surface. Each recess has a recessed wall, a front sidewall, a rear sidewall and a bottom wall. The second jaw includes a plurality of staple pockets. Each staple pocket is defined by each recess including an opening to the top surface of the second jaw. The first surface includes a plurality of longitudinally extending grooves formed into the first surface. The surgical stapler further includes an actuator coupled to the handle assembly. A first caming surface is also provided. The first caming surface includes a plurality of projections sized and configured to fit within the longitudinally extending grooves of the first surface and translate therein. The first caming surface is movable by the actuator along a length of the second jaw. The surgical stapler includes a plurality of staples positioned in the plurality of staple pockets. Each staple has a staple width and is positioned within and supported by a staple pocket. With translation of the first caming surface along the jaw assembly, the projections of the first caming surface pass through one or more staple pockets making contact with a portion of the staple width to urge the staple out of the opening and against the anvil surface.

BRIEF DESCRIPTION OF THE DRAWINGS

FIG. 2 is a side view of a stapler cartridge assembly according to the present invention.

FIG. 3 is semi-transparent side view a proximal end of a stapler cartridge assembly according to the present invention.

FIG. 4 is side view of an actuator shaft and I-beam according to the present invention.

FIG. 5 is a perspective view of a distal end of an actuator shaft and I-beam according to the present invention.

FIG. 14 is a top perspective view of a lower jaw according to the present invention.

FIG. 15 is a side view of a lower jaw according to the present invention.

FIG. 16 is a top rear perspective view of a lower jaw according to the present invention.

FIG. 18 is a top view of a staple cartridge according to the present invention.

FIG. 20 is a side view of first plate of a staple cartridge according to the present invention.

FIG. 22 is a top perspective sectional view of a staple cartridge, I-beam and slider according to the present invention.

FIG. 28 is a side elevational view of a slider according to the present invention.

FIG. 29 is a top view of a slider according to the present invention.

FIG. 30 is a top rear perspective view of a slider according to the present invention.

FIG. 31 is a top perspective view of a staple according to the present invention.

FIG. 61 is a semi-transparent, side elevational, sectional view of an end effector according to the present invention.

DETAILED DESCRIPTION

Figure 1:
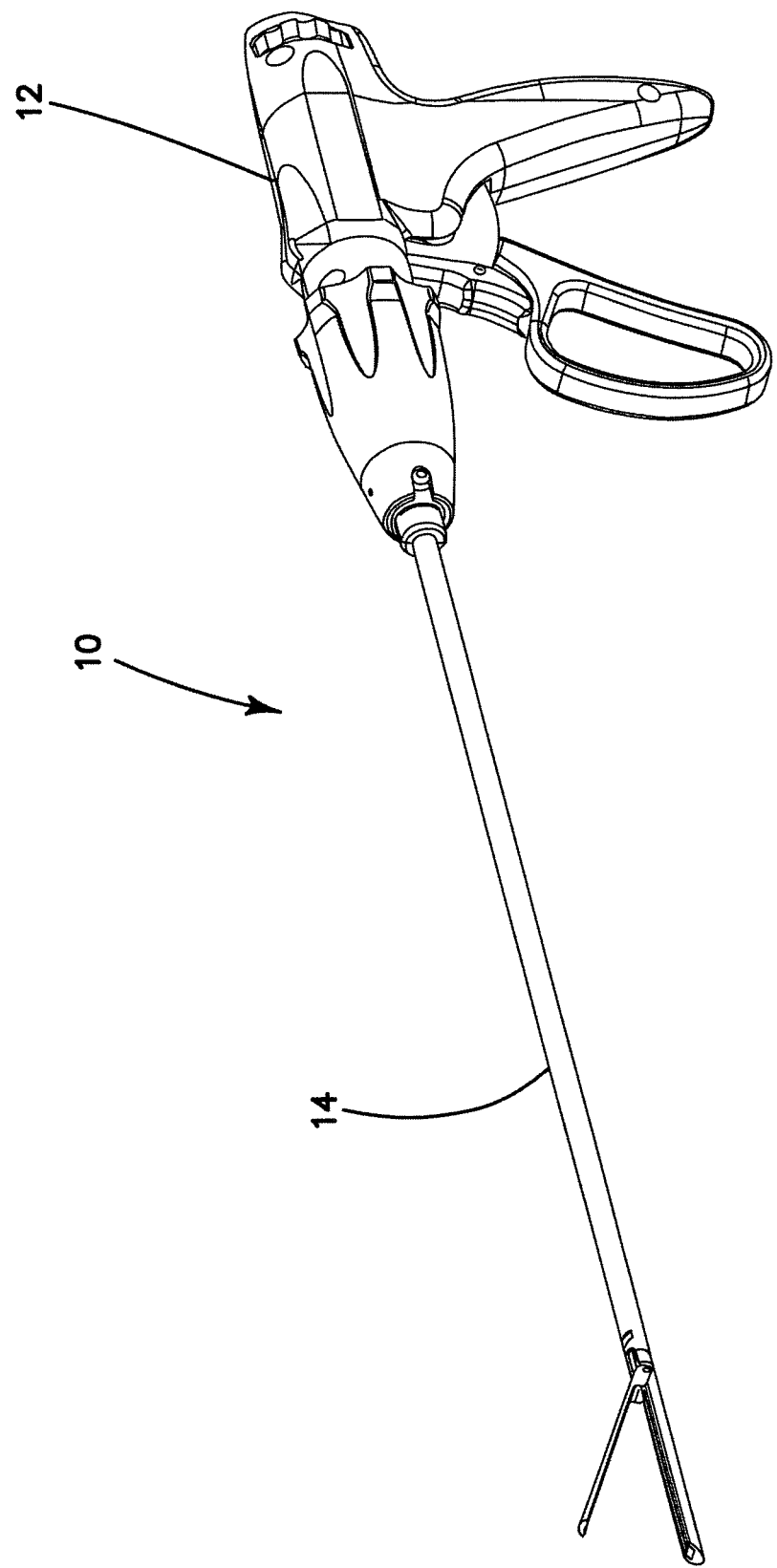
FIG. 1 is a perspective view of a surgical stapler according to the present invention.

Referring to FIG. 1, there is shown a perspective view of a surgical stapler 10 according to the present invention. The stapler 10 is comprised of a handle assembly 12 removably connected to a stapler cartridge assembly 14. The handle assembly 12 is configured to control the instrument and actuate deployment of staples located in the distal end of the stapler cartridge assembly 14. After the staples have been expended from the stapler 10, the stapler cartridge assembly 14 is removed from the handle assembly 12 and a new stapler cartridge assembly 14 is connected to the handle assembly 12 for continued stapling.

Turning to FIG. 2, the stapler cartridge assembly 14 will now be discussed in detail. The stapler cartridge assembly 14 includes a connector 16 at the proximal end and an end effector 18 at the distal end. An outer tube 20 is connected to the end effector 18 at the distal end and to the connector 16 at the proximal end. An actuator shaft 22 is disposed inside the lumen of the outer tube 20. The outer tube 20 is substantially cylindrical having an outer diameter of approximately 5-10 mm. The actuator shaft 22 is configured to slide longitudinally relative to the outer tube 20. Detail of the proximal end of the stapler cartridge assembly 14 is shown in FIG. 3.

Turning to FIG. 3, the proximal end of the stapler cartridge assembly 14 is shown. The connector 16 includes a bolt 24 that extends laterally outwardly from the outer surface of the connector 16. A similar bolt 24 extends on the opposite side of the connector 16 and is not visible in FIG. 3. The bolt 24 is configured for a bayonet-like connection with the handle assembly 12 of the stapler 10 that includes a complementary slot for receiving the bolt 24 to secure the cartridge assembly 14 to the handle assembly 12. FIG. 3 also illustrates the actuator shaft 22 moved proximally relative to the outer tube 20 when compared to FIG. 2 in which the actuator shaft 22 is shown to be moved more distally relative to the outer tube 20. As seen in FIG. 3, the proximal end of the actuator shaft 22 includes a bolt 26 that extends laterally outwardly from the actuator shaft 22. The bolt 26 is configured for a bayonet-like connection with an actuator shaft of the handle assembly 12 which includes a complementary slot for receiving the bolt 26. Mating the bolt 24 of the connector 16 to handle assembly 12 simultaneously mates the bolt 26 of the actuator shaft 22 to the actuator shaft of the handle assembly 12. When connected to the handle assembly 12, the handle assembly 12 is used to move the actuator shaft 22 forward and backward inside the outer tube 20 to effect opening and closing of the distal jaw-like members and the deployment of staples.

Turning to FIG. 4, the actuator shaft 22 will now be described. The actuator shaft 22 is an elongated shaft having a substantially cylindrical proximal portion 28 having actuator bolts 26 at the proximal end for connection with the actuator of the handle assembly 12. The substantially cylindrical portion 28 is sized to fit closely inside the lumen of the outer tube 20. The cylindrical portion 28 is connected with pins to an extended I-beam portion 30 toward the distal end of the actuator shaft 22. The distal end of the actuator shaft 22 includes an I-beam 32 connected to the extended I-beam portion 30. The I-beam 32 is connected to the extended I-beam portion 30 as shown in FIG. 5.

Figure 6:
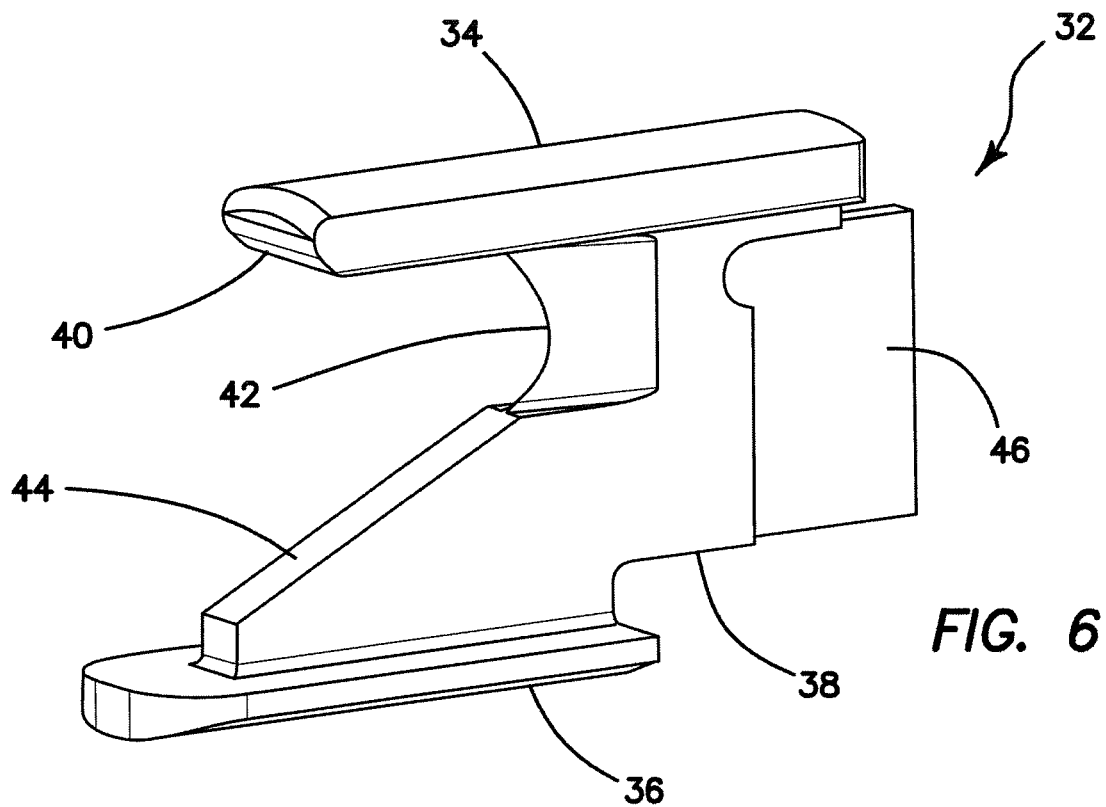
FIG. 6 is a perspective view of an I-beam according to the present invention.
Figure 7:
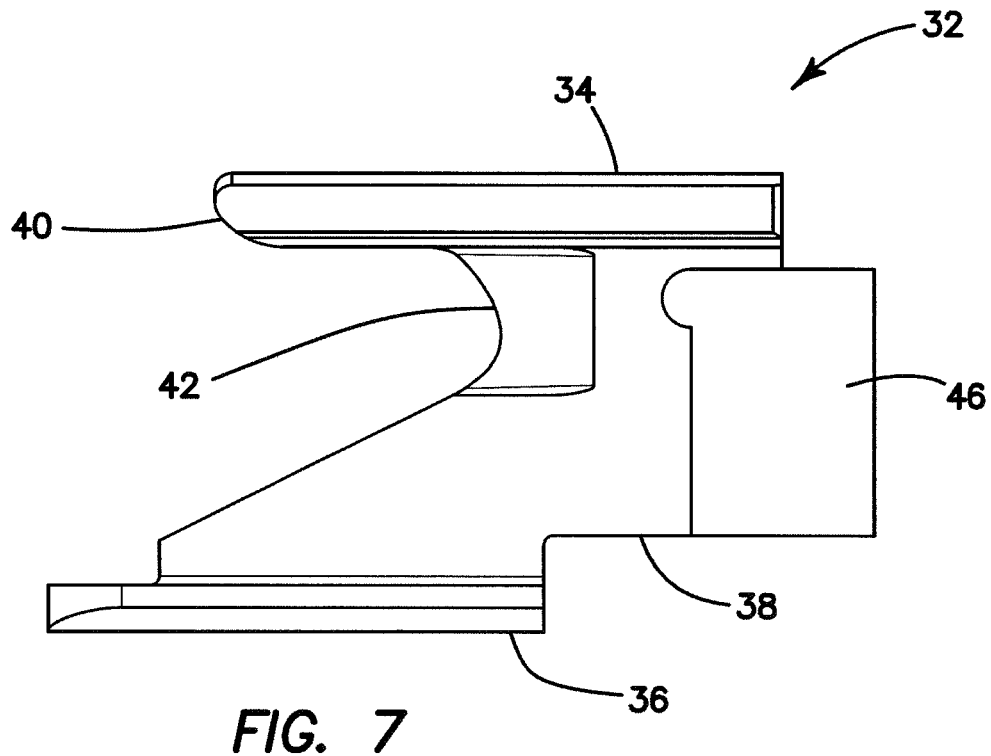
FIG. 7 is a side view of an I-beam according to the present invention.
Figure 8:
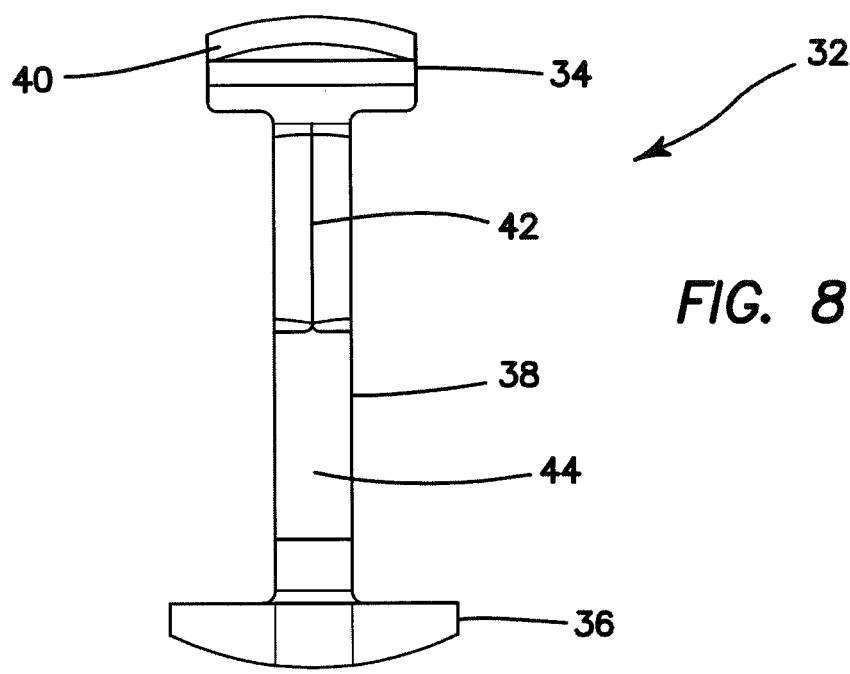
FIG. 8 is an end view of an I-beam according to the present invention.

Turning now to FIGS. 6-8, the I-beam 32 will now be described. The I-beam 32 includes a top portion 34 and a bottom portion 36 interconnected by a middle portion 38. The top portion 34 includes a beveled front end 40 and a curved top. The middle portion 38 includes a blade 42 and an angled portion 44 at the front end. At the back end, the middle portion 38 includes an extension 46 for connecting with the extended I-beam portion 30 as shown in FIG. 5. The bottom portion 36 leads the front end of the I-beam 32 and includes a curved bottom. The front-elevational view of the I-beam is shown in FIG. 8 which illustrates the profile to be in the shape of a capital letter "I".

Figure 9:
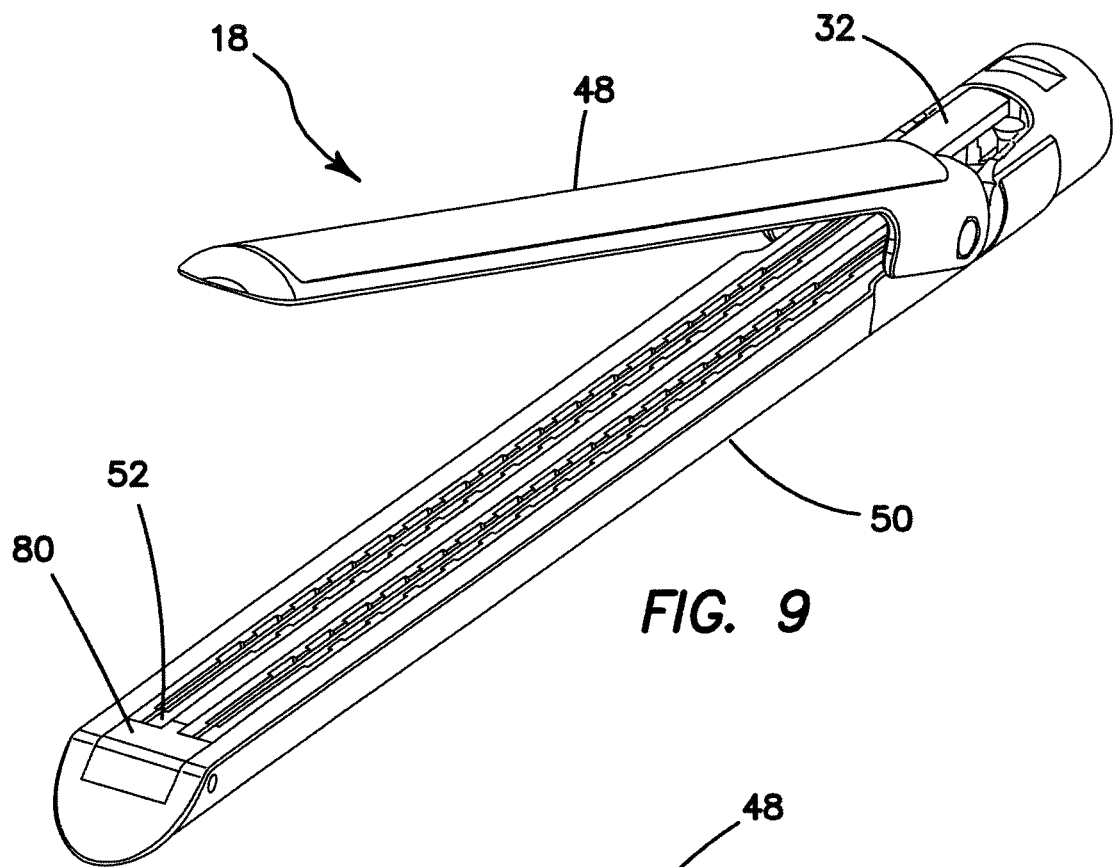
FIG. 9 is a perspective view of an end effector with jaws in an open position according to the present invention.

Turning now to FIG. 9, the end effector 18 will be described. The end effector 18 includes an upper jaw 48 hinged to a lower jaw 50. At least one staple cartridge 52 containing a plurality of staples 54 is disposed inside the lower jaw 50. The at least one staple cartridge 52 is configured to received a plurality of staples 54 that are not visible in FIG. 9. The end effector 18 further includes a slider 56 configured to urge the staples 54 out of the cartridge 52. The slider 56 is not visible in FIG. 9.

Figure 11:
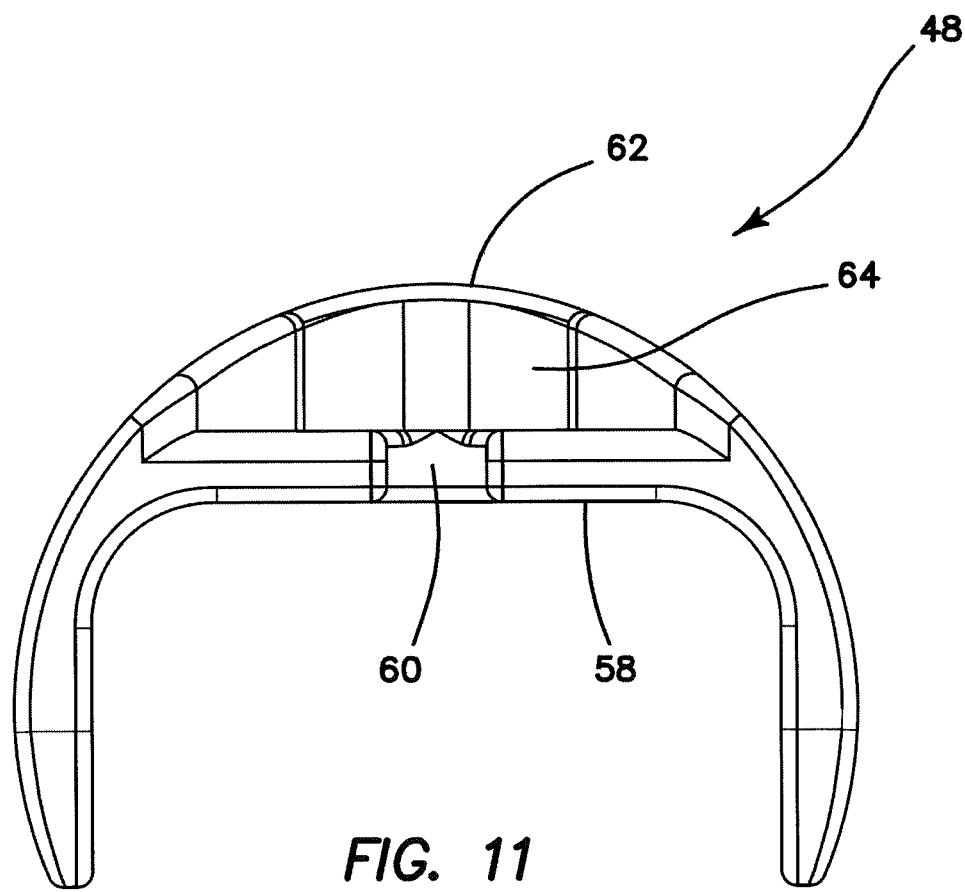
FIG. 11 is an end view of an upper jaw according to the present invention.
Figure 10:
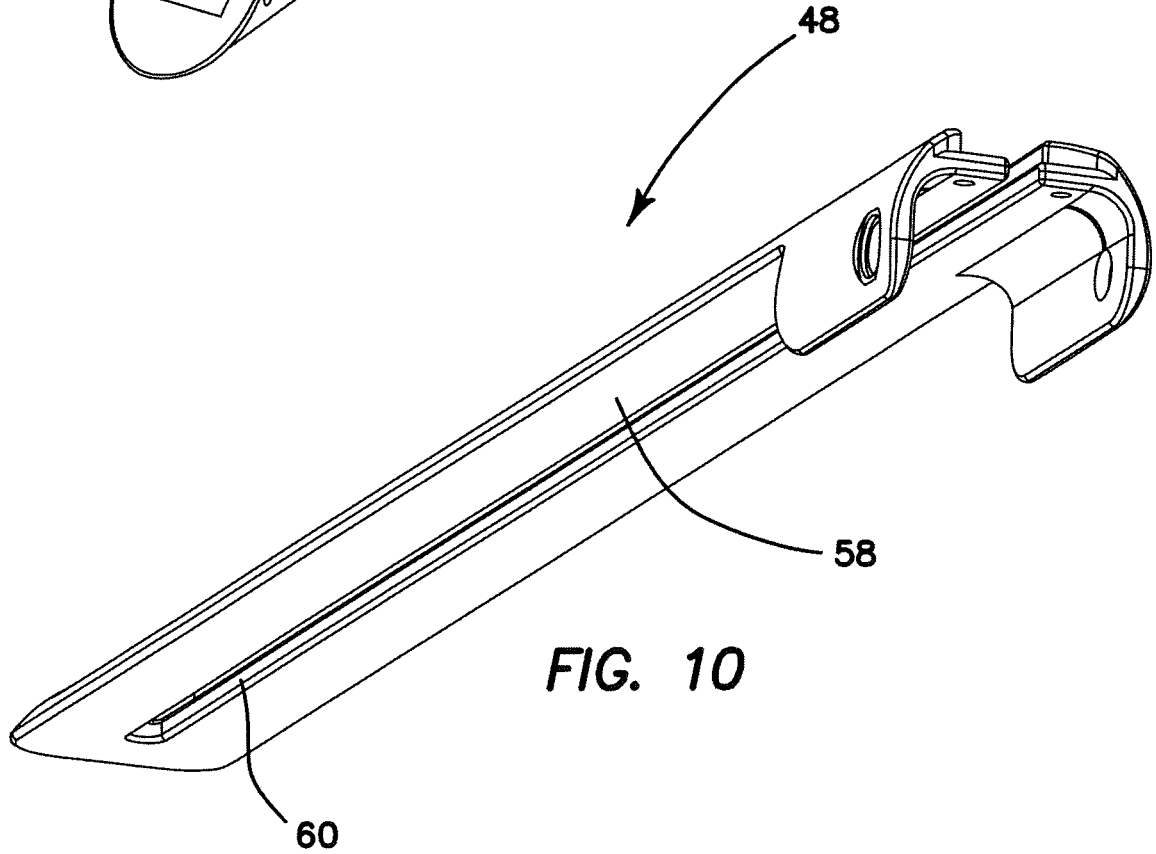
FIG. 10 is a bottom perspective view of an upper jaw according to the present invention.

Turning to FIGS. 10-11, the upper jaw 48 will now be described. The upper jaw 48 includes a flat anvil surface 58 or plate defining a central slot 60. The central slot 60 is elongated with an open proximal end. The central slot 60 is sized and configured to receive at least a portion of the middle portion 38 of the I-beam 32 such that the I-beam 32 slides relative to the upper jaw 48 inside and along the central slot 60. The outer surface of the upper jaw 48 is curved and substantially semicircular in shape to conform to a cylindrical lumen of a cannula in which it is inserted. The upper jaw 48 includes a top cover 62. The top cover 62 forms part of the outer circumference of the upper jaw 48 and together with the anvil surface 58 define therebetween a passageway 64 for receiving the top portion 34 of the I-beam 32 such that the top portion 34 slides relative to the upper jaw 48 inside the passageway 64. At the proximal end, the upper jaw 48 further includes flanges having apertures for receiving pins and connecting to the lower jaw 50.

Figure 12:
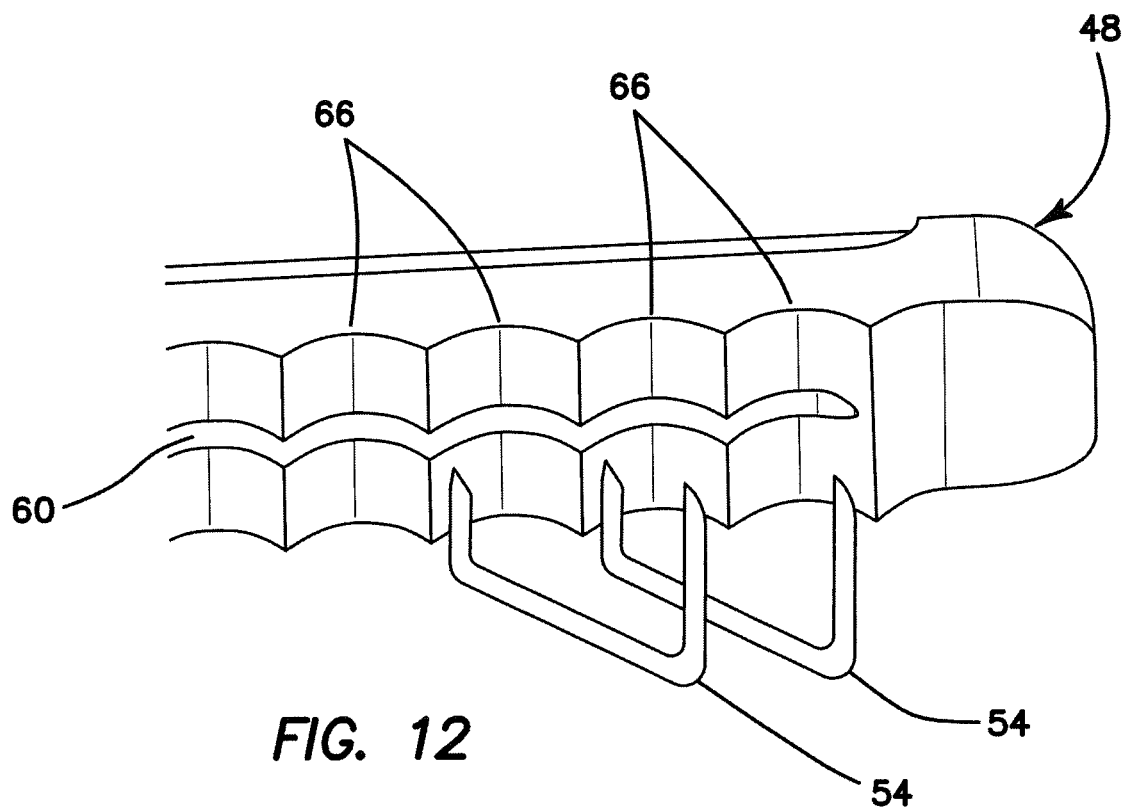
FIG. 12 is a bottom perspective view of an upper jaw with curved channels according to the present invention.
Figure 13:
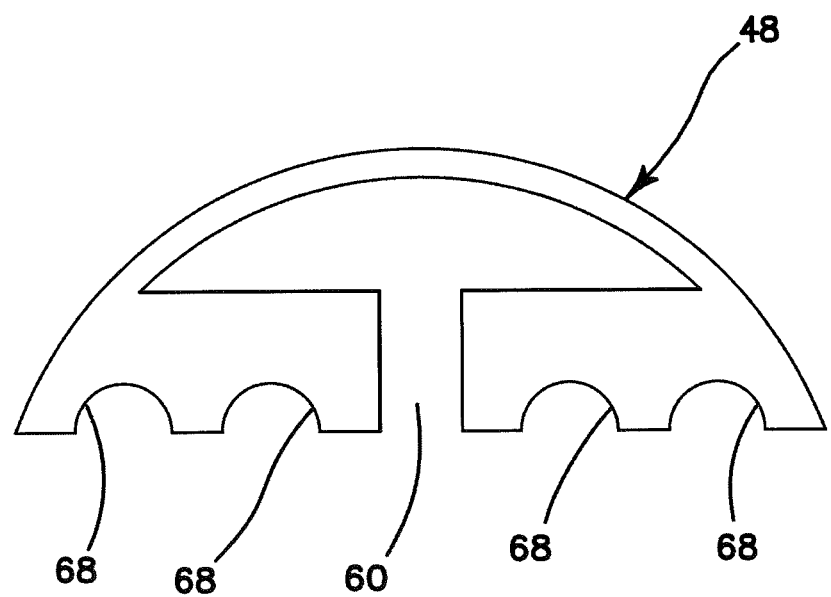
FIG. 13 is an end view of an upper jaw with curved channels according to the present invention.
Figure 17:
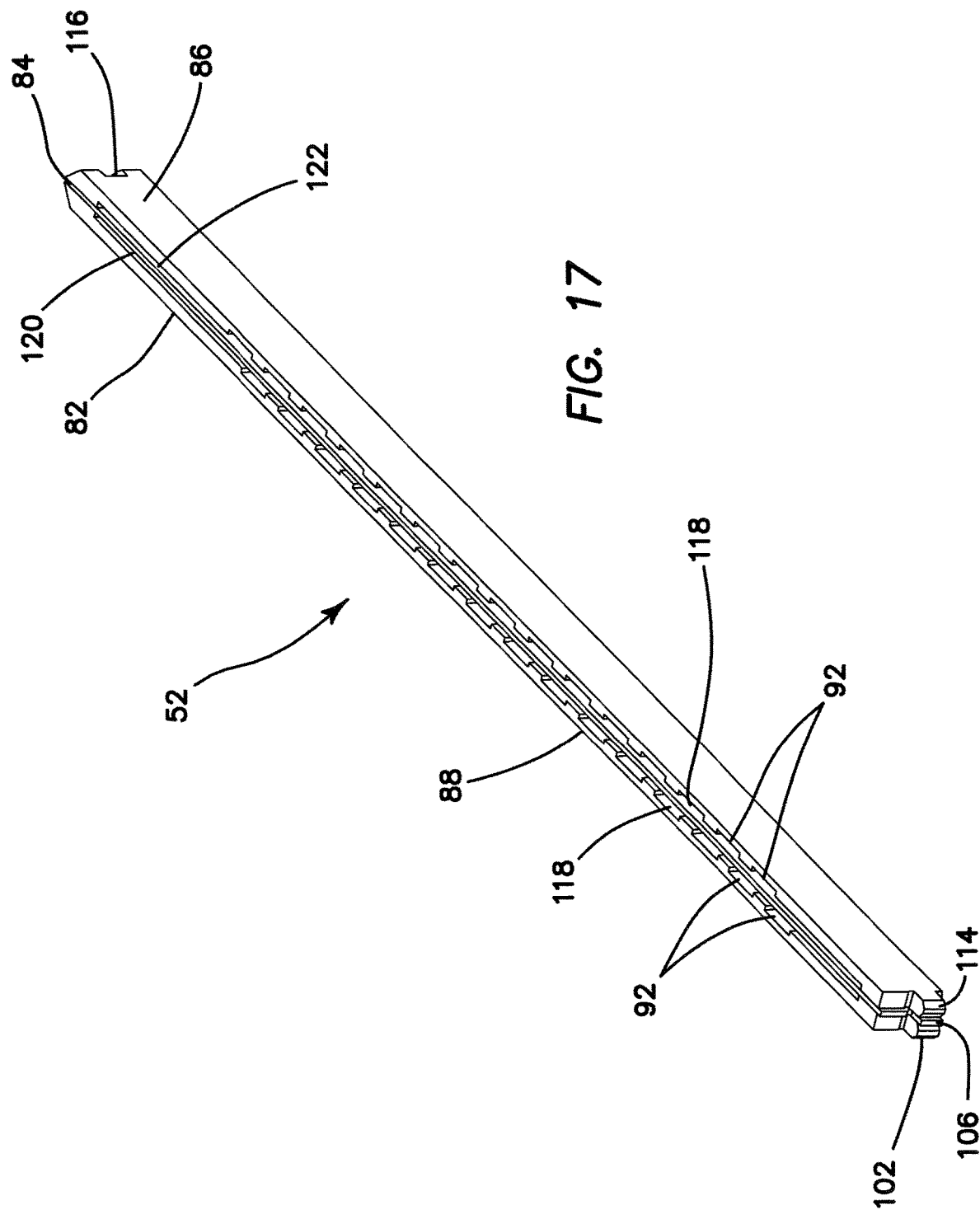
FIG. 17 is a top perspective view of a staple cartridge according to the present invention.
Figure 19:
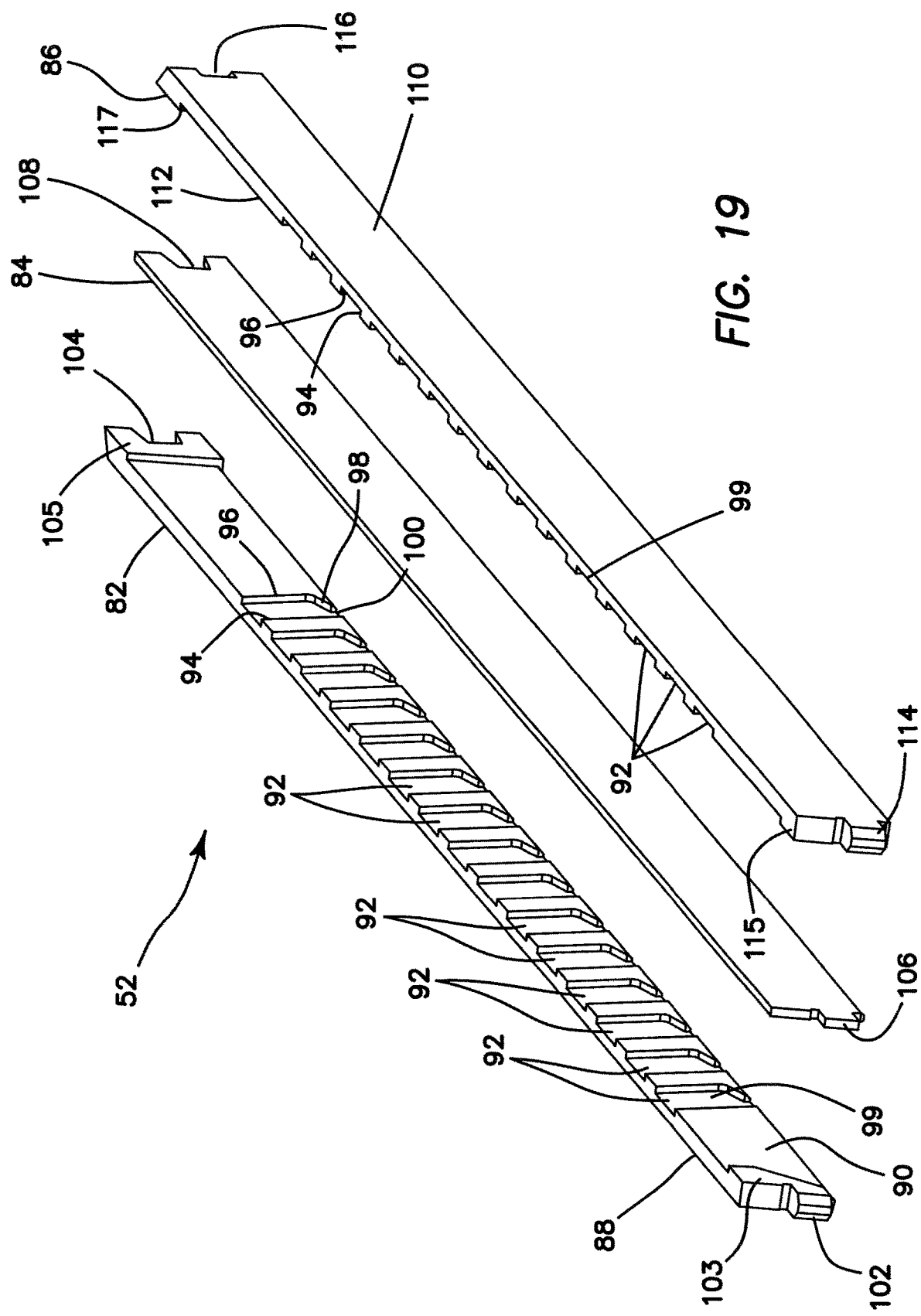
FIG. 19 is an exploded top perspective view of a staple cartridge according to the present invention.
Figure 21:
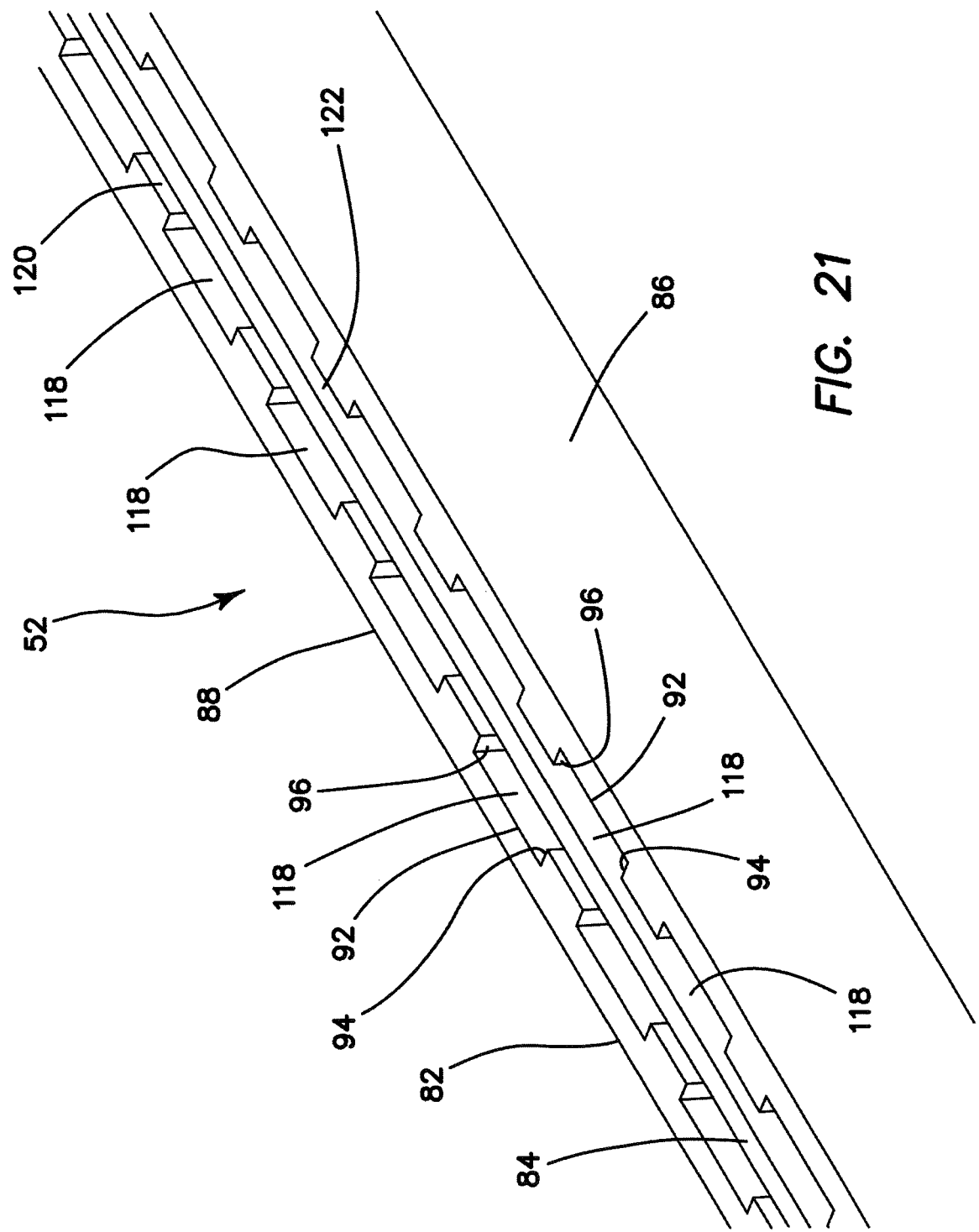
FIG. 21 is a top perspective sectional view of a staple cartridge according to the present invention.

A typical anvil of a conventional surgical stapler includes staple-forming pockets in the surface of the anvil that are designed to receive the legs of a staple and guide, angulate and bend the staple legs as the staple is urged against the anvil. These surface formations of a typical anvil aid in the deformation of the staple as it is deployed to achieve proper staple formation. Any misalignment between the staple-forming pockets and the staple leads to the staples missing the staple forming pockets, resulting in catastrophic failure of the staple line. The detailed staple-forming pockets introduce significant manufacturing difficulties and increase costs of production. Advantageously, the present invention does not utilize staple-forming pockets in the surface of the anvil. The anvil surface is smooth and/or flat. By redesigning the staple to not require anvil pockets to be formed, anvil pockets are eliminated completely simplifying the design while advantageously bringing an additional level of reliability to the stapler 10. Slight misalignment is no longer a concern especially with flat plate designs. The simplified design is also a major benefit for manufacturing as the anvil costs are reduced and the need for ultra-high precision parts to maintain perfect alignment are no longer needed. In one variation, the anvil surface 58 is completely flat as shown in FIG. 10. In another variation shown in FIG. 12, the anvil surface includes a series of curved channels 66 having substantially smooth surfaces against which staples can deform into the proper configuration. The lengths of the channels 66 are perpendicular to the longitudinal axis of the upper jaw 48. The wave-like arrangement of channels 66 defines a central slot 60 in the anvil surface and reduces the need for critical alignment from side to side. Critical alignment of the staple is not required as the channels 66 are wide enough to easily receive the staple legs. The curvature of the channels 66 assists in deflecting the staple legs in the proper direction. In another variation, the anvil surface includes two or more longitudinal curved channels 68 that extend along the axis of the device as shown in FIG. 13. The elongate curved channels 66, 68 permit the formation of staples 54 without the worry and cost of proper alignment of each staple with each staple-forming pocket. Although the channels 66, 68 are shown to be curved, they can have square or rectangular cross-sections for assisting in closing the staple in the desired direction.

Referring now to FIGS. 14-16, the lower jaw 50 will be described. The lower jaw 50 is an elongate piece sized and configured to complementarily mate with the upper jaw 48. The lower jaw 50 has an open top and a curved outer surface. The cross-section of the lower jaw 50 is substantially semi-circular in shape except at the proximal end where it is substantially circular in cross-section. The depending flanges of the upper jaw 48 attach to the lower jaw 50 via pins inserted into apertures in the lower jaw 50 near the proximal end. When attached together, the upper jaw 48 and lower jaw 50 create a substantially cylindrical profile. The distal end of the lower jaw 50 is angled and the cylindrical proximal end defines a vertically oriented slot 70 visible in FIG. 16. This slot 70 is sized and configured to receive the extended I-beam portion 30 of the actuator shaft 22 with the I-beam itself 32 residing inside the lower jaw 50 distal of the slot 70. The cylindrical proximal end is adapted for attachment to the outer tube 20. The lower jaw 50 further includes a staple cartridge receiving portion 72. When one or more staple cartridges 52 are inserted into the staple cartridge receiving portion 72 of the lower jaw 50, a passageway is defined between the one or more staple cartridges 52 and a bottom cover 74. This passageway is sized and configured to receive the bottom portion 36 of the I-beam 32 such that the bottom portion 36 slides longitudinally with respect to lower jaw 50 inside the passageway. Inside the staple cartridge receiving portion 72, there is a ledge 76 at the distal end for securing the front end of one or more staple cartridges 52. A tongue 78 is formed at the proximal end for mating with a groove of the staple cartridge 52 to secure the proximal end of the staple cartridge 52 to the lower jaw 50. A cartridge retainer 80, shown in FIG. 9, covers the distal end tongues of staple cartridges 52 after being inserted into the lower jaw 50.

Referring now to FIGS. 17-22, the staple cartridge 52 will be described. The staple cartridge 52 comprises first plate 82, a second plate 84 and a third plate 86 connected together. The plates 82, 84, 86 are made from any polymer material, metal such as aluminum or stainless steel or glass filled nylon. The first plate 82 is elongate and substantially rectangular in shape and includes an outer surface 88 and an inner surface 90. The outer surface 88 is smooth and the inner surface 90 is formed with a plurality of staple holding locations 92. The staple holding locations 92 are recesses formed in the inner surface 90 of the first plate 82. Each staple holding location 92 is substantially U-shaped and defined by a front sidewall 94 formed oppositely and substantially parallel to a rear sidewall 96. The rear sidewall 96 is interconnected to a bottom wall 98 forming an L-shaped continuous wall defining a gap 100 between the bottom wall 98 and the front sidewall 94. In one variation, no gap 100 is formed. Instead, the bottom wall 98 interconnects with both the front sidewall 94 and rear sidewall 96 to form a complete U-shaped staple holding location 92. The U-shaped staple holding locations are angled approximately 30-90 degrees with 90 degrees being a vertical non-angled orientation. The recessed wall 99 is recessed with respect to the inner surface 90. The first plate is approximately 0.020-0.025 inches thick and the depth of each recess or thickness of each sidewall 94, 96, 98 is approximately 0.005-0.008 inches. The staple holding locations 92 are configured for partially receiving and holding a complementary, substantially U-shaped staple that is thicker than the thickness of the sidewalls 94, 96, 98. The distal end of the first plate 82 includes a tongue 102 and the proximal end of the first plate 82 includes a groove 104 for connecting with the ledge 76 and tongue 78 of the lower jaw 50. The distal end and proximal end of the first plate 82 further include spacers 103, 105, respectively, that extend inwardly and are configured to space the inner surface 90 from the second plate 84. The first plate 82 is made of metal or plastic.

The second plate 84 or middle shim 84 is a thin elongate substantially rectangular shaped plate of metal or plastic having smooth outer surfaces. The second plate 84 is approximately 0.010-0.020 inches thick. The distal end includes a tongue 106 and the proximal end includes a groove 108 that are configured for connecting with the ledge 76 and tongue 78 of the lower jaw 50. In another variation, two second plates 84a, 84b are provided and each is approximately 0.005 inches in thickness. The first second plate 84a is sprung such that the first second plate exerts a force towards the first plate 82 and the other second plate 84b is also sprung such that it exerts a force towards the third plate 86.

The third plate 86 is substantially identical to and a mirror image of the first plate 82. The third plate 86 is elongate and substantially rectangular in shape and includes an outer surface 110 and an inner surface 112. The outer surface 110 is smooth and the inner surface 112 is formed with a plurality of staple holding locations 92 substantially identical to and a mirror image of the staple holding locations 92 of the first plate 82. The staple holding locations 92 are recesses formed in the inner surface 112 of the third plate 86. Each staple holding location 92 is substantially U-shaped and defined by two oppositely formed substantially parallel sidewalls, a front sidewall 94 and a rear sidewall 96. The rear sidewall 96 is interconnected to a bottom wall 98 forming an L-shape continuous wall defining a gap 100 between the bottom wall 98 and the front sidewall. In one variation, no gap 100 is formed. Instead, the bottom wall 98 interconnects with both the front sidewall 94 and rear sidewall 96 to form a complete U-shaped staple holding location 92. The recessed wall 99 is recessed with respect to the inner surface 112. The U-shaped staple holding locations are angled approximately 30-90 degrees with 90 degrees being a vertical non-angled orientation. The third plate is approximately 0.020-0.025 inches thick and the depth of each recess or thickness of each sidewall 94, 96, 98 is approximately 0.005-0.008 inches. The staple holding locations 92 are configured for partially receiving and holding a complementary, substantially U-shaped staple that is thicker than the thickness of the sidewalls 94, 96, 98. The distal end of the third plate 82 includes a tongue 114 and the proximal end of the third plate 86 includes a groove 116 for connecting with the ledge 76 and tongue 78 of the lower jaw 50. The distal end and proximal end of the third plate 82 further include spacers 115, 117, respectively, that extend inwardly and are configured to space the inner surface 112 of the third plate 86 from the second plate 84.

The first plate 82, second plate 84 and third plate 86 are connected or sandwiched together to form a staple cartridge 52 having two rows of staggered staple pockets 118 for placement on one side of the blade 42 of the I-beam 32. The staple pockets 118 are staggered to form a more complete closed line of staples. A second staple cartridge 52 is placed on the other side of the blade 42 of the I-beam 32 forming two rows of staple pockets 118 on the other side of the blade 42 for a total of four rows of staple pockets 118. The cartridges 52 can be modified with additional plates to create more than two rows of staples and can include three or four rows of staples on each side of the I-beam 32. The staple pockets 118 are defined by the recessed wall 99, the front sidewall 94, rear sidewall 96, bottom wall 98 and the outer surface of the second plate 84. Each pocket 118 includes an open top and a partially open bottom. In one variation, the bottom is closed. Because the spacers 103, 105 of the first plate 82 space the inner surface 90 of the first plate 82 from the second plate 84, a first slot 120 is formed between the first plate 82 and the second plate 84. The first slot 120 is configured for receiving a first angled caming surface of the slider 56 that will be described in greater detail herein below. The first slot 120 intersects with the first row of staple pockets 118. Because the spacers 115, 117 of the third plate 86 space the inner surface 112 of the third plate 86 from the second plate 84, a second slot 122 is formed between the third plate 86 and the second plate 84. The second slot 122 is configured for receiving a second angled caming surface of the slider 56 that will be described in greater detail herein below. The second slot 122 intersects with the second row of staple pockets 118. The same configuration appears on the staple cartridge disposed on the other side of the I-beam 32. The staple cartridge 52 is considered to be a single unit holding all the staples on either side of the I-beam 32 or alternatively, there are two staple cartridge units, one disposed on either side of the I-beam 32.

Turning now to FIG. 22, there is shown another variation of the staple cartridge 52 wherein the second plate 84 is not smooth but also includes a plurality of staple holding locations 124 similar to the staple holding locations 92 of the first and third plates 82, 86. In this variation, both opposite outer surfaces of the second plate 84 include recesses defined by a recessed wall 126 that is recessed from the outer surface, a front sidewall 128, a rear sidewall 130 and a bottom wall (not shown). The bottom wall may or may not include a gap. The staple holding locations 124 in a first outer surface of the second plate 84 are located opposite to the staple holding locations 92 of the first plate 82 which together define the staple pocket 118. Also, the staple holding locations 124 formed in a second outer surface of the second plate 84 are located opposite to the staple holding locations 92 of the third plate 86 which together define the staple pockets 118. The staple holding locations 124 have the same angle as their opposite staple holding locations 92 in the first and third plates 82, 86. Each pocket 118 defined by staple holding locations 92 and 124 are configured to receive substantially U-shaped staples 54 such that they are supported by the sidewalls yet include an unsupported portion of the staple 54 that resides in the first and second slots 120, 122. This unsupported portion of the staple 54 that resides in either the first or second slots 120, 122 is exposed for contact with the angled caming surface of the slider 56 as it passes through the slot and urges the staple 54 upwardly out of the pocket 118. In this variation in which the second plate 84 includes staple holding locations 124, the depth of the staple receiving portions 92, 124 are approximately 0.005 inches each and the width of each slot 120, 122 is approximately 0.005-0.006 inches with the total thickness of the staple 54 being approximately 0.015 inches with approximately 0.005 inches of the staple residing in the slot 120, 122, approximately 0.005 inches of the staple residing in and supported by the staple holding location 92 of the first plate 82 and approximately 0.005 inches of the staple residing in and supported by the staple holding location 124 of the third plate 86. FIG. 22 illustrates the standard arrangement in which two rows of staggered staple pockets 118 are located on either side of the slider I-beam 32 blade 42 for delivering a total of four lines of staggered staples 54. In another variation, the staple cartridge 52 is configured to include an additional fourth plate (not shown) sandwiched together for creating a third row of staples pockets 118 on either side of the blade 42 for a total of six rows of staggered staples 54. Any number of staple rows is within the scope of the present invention achieved by the adding of additional plates.

Figure 23:
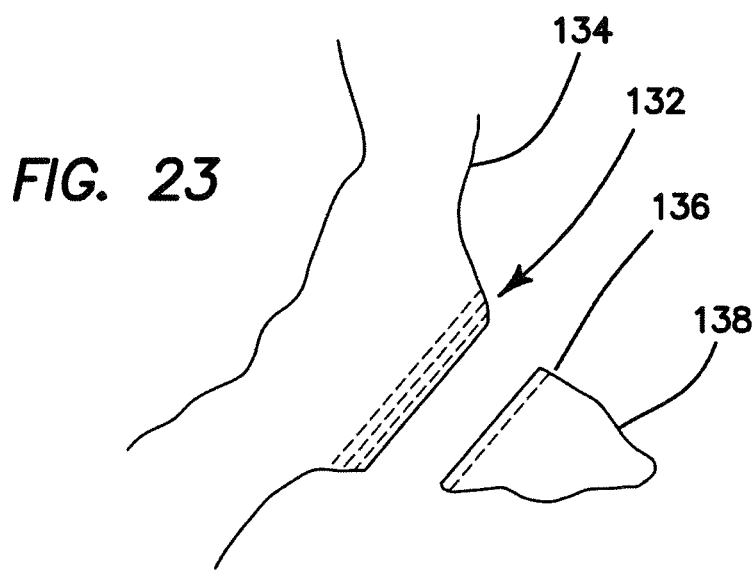
FIG. 23 is a schematic of removed tissue resolved with an asymmetric staple cartridge according to the present invention.
Figure 24:
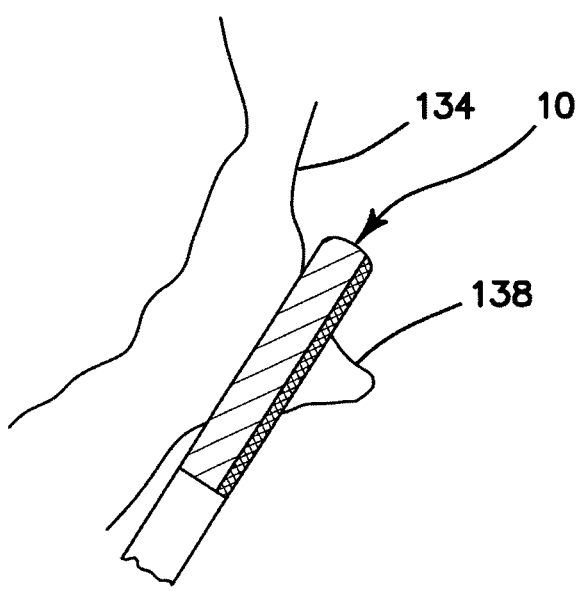
FIG. 24 is a schematic of an asymmetric stapler grasping tissue according to the present invention.
Figure 25:
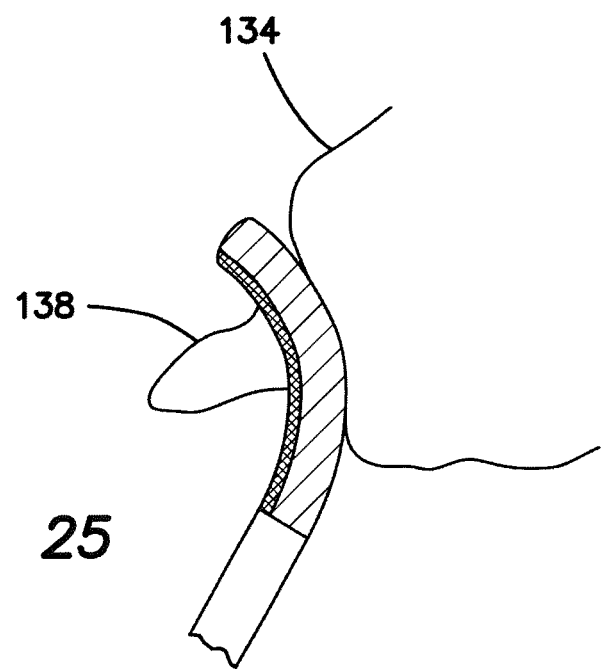
FIG. 25 is a schematic of an asymmetric stapler with a curved end effector according to the present invention.
Figure 26:
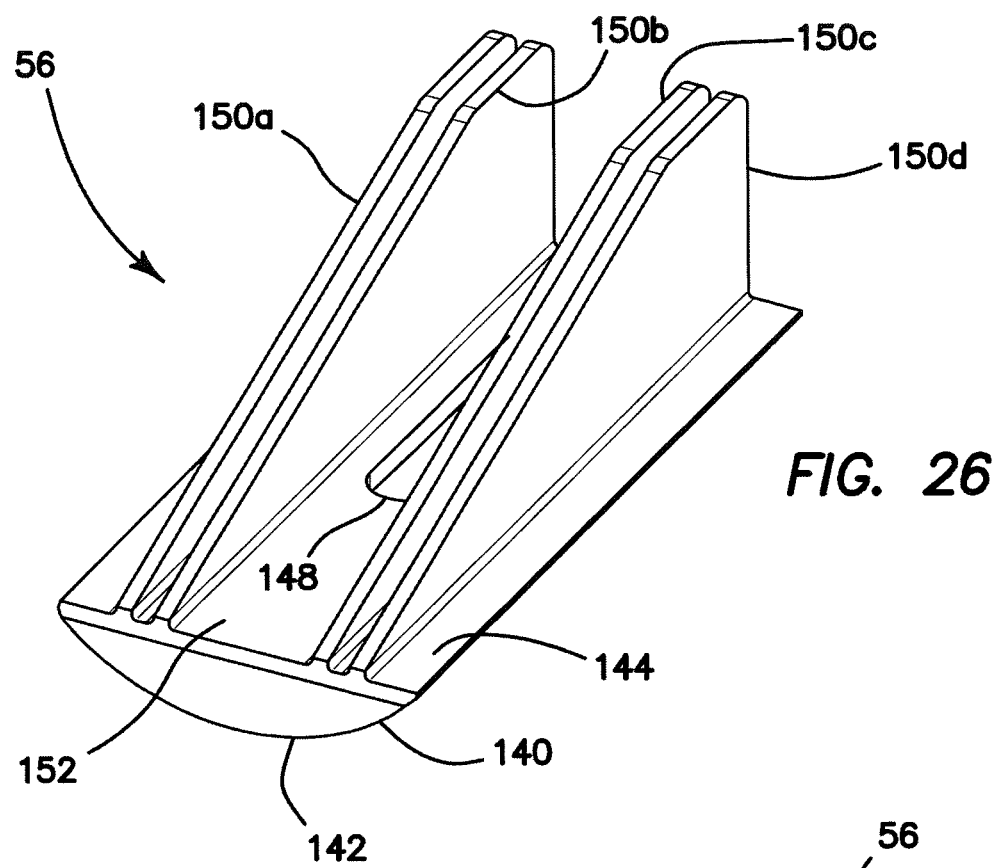
FIG. 26 is a top perspective view of a slider according to the present invention.
Figure 27:
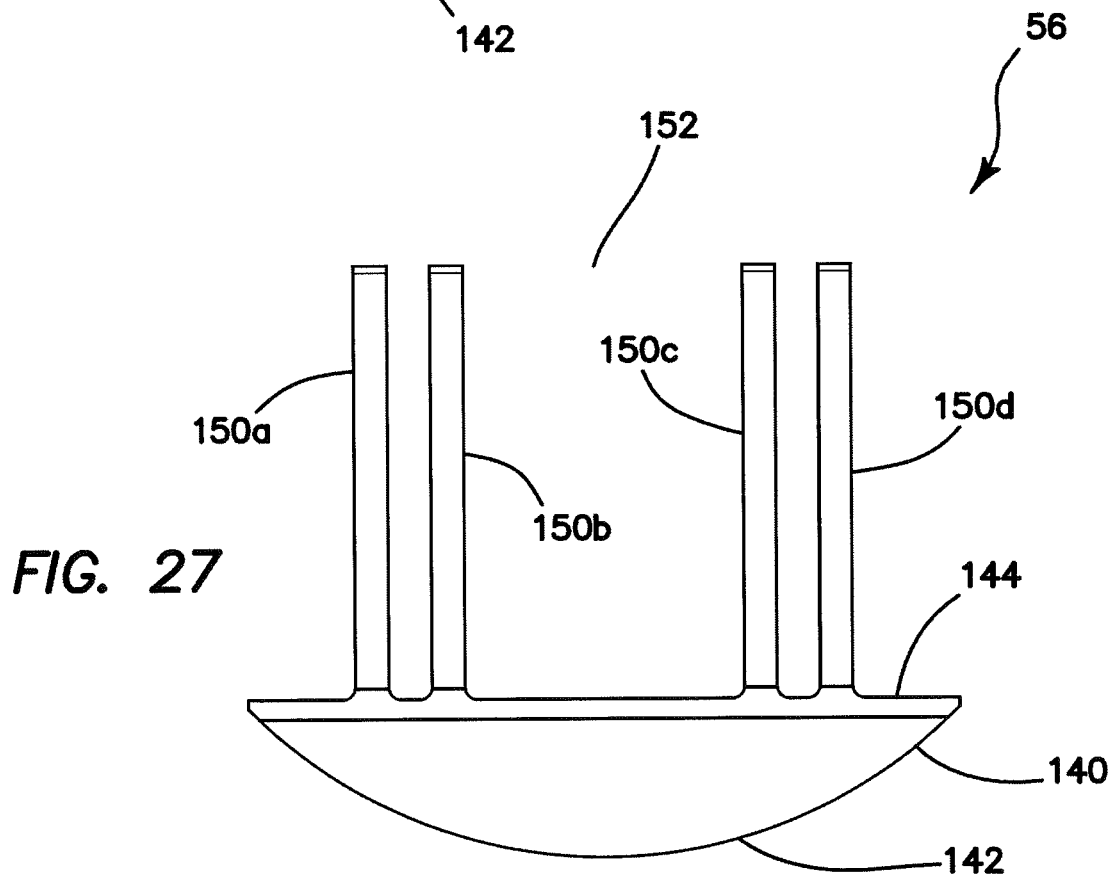
FIG. 27 is an end view of a slider according to the present invention.

Turning now to FIGS. 23-25, in one variation of the invention, an asymmetrical staple cartridge is provided. The asymmetrical staple cartridge utilizes a different number of rows of staple pockets on either side of the I-beam 32 blade 42. In one variation, the staple cartridge includes two or three rows of staple pockets on one side of the I-beam 32 blade 42 and only one row of staple pockets on the other side of the I-beam 32 blade 42 creating a total of three or four rows of staples with one row of staples delivered on one side of the cutting line. The staple cartridge may be a single unitary piece or be comprised of two cartridges, one having two or three rows of staple pockets for delivering two or three rows of staples placed on one side of the blade 42 and a second staple cartridge having only one row of staple pockets for delivering only one row of staples on the other side of the blade 42. The asymmetric stapler advantageously results in a smaller device with a decreased diameter of the end effector 18. Alternatively, the saved space in the end effector 18 can be utilized to advantageously provide additional structural support in a device of the same diameter. While two to three rows of staples on both sides of the blade 42 may be preferred for holding living tissue, a specimen to be removed may only require one row of staples on one side of the cutting line designed for short term holding onto tissue to be removed. The resulting smaller device diameter would be beneficial in certain procedures such as in the removal of an endoluminal polyp. In such a procedure, the endoluminal polyp removal stapler would have two or three rows of staples on one side of the blade for delivering two or three rows of staples into the colon side of the cutting line and one row of staples for delivering one row of staples into the polyp side of the cutting line. Through the use of different number of staple rows on either side of the cutting line, the staplers can be tailored to their specific surgical applications. The result is a dramatic reduction in instrument size, in particular, the diameter of the end effector 18, or alternatively an instrument with of same size but having increased instrument strength and reliability. FIG. 23 illustrates the resulting cut employing an asymmetrical stapler according to the present invention. FIG. 23 shows three lines 132 of staggered staples delivered into the organ side 134 and one line of staples 136 delivered into the removed tissue 138. In order to provide to the surgeon user visual indication as to which side of the stapler 10 delivers fewer rows, the end effector 18 of the stapler 10 is color coded such that the side of the stapler 10 that has fewer rows of staples is colored a different color from the side of the stapler that has two or more rows of staples as shown in FIG. 24. For example, the side of the stapler with a single line of staples is colored red and the other side of the blade is colored green. Other markings on the stapler 10 are possible. In another variation shown in FIG. 25, the end effector 18 of the stapler is curved such that the surgeon knows to place the concave portion of the curvature against or on the side of the polyp 138, for example, and the convex side of the curved end effector against the colon side 134. The curved jaws assist the surgeon user in denoting proper orientation of the stapler with the concave side of the curvature having few rows of staples compared with the concave side of the blade which has a greater number of rows of staples. In another variation, the concave side of the stapler blade includes fewer rows of staples relative to the convex side of the stapler blade.

Turning now to FIGS. 26-30, the slider 56 will be described. The slider 56 includes a slider base 140 having a bottom surface 142 and a top surface 144. At least a portion of the bottom surface 142 toward the distal end is curved to conform to the curved bottom 74 of the lower jaw 50. At the proximal end of the slider 56, the bottom surface 142 includes a recessed portion 146 sized and configured to receive the bottom portion 36 of the I-beam 32. A slot 148 is formed in the slider base 140 that opens at the proximal end and extends toward the distal end of the slider base 140. The slot 148 is sized and configured to receive at least the lower middle portion 38 of the I-beam 32. In one variation, the front end of the slider 56 that leads distal translation includes a beveled or angled front surface to assist in urging staples from the device. Upstanding from the top surface 144 of the slider base 140 are at least two angled caming surfaces 150. FIGS. 26-30 depict a slider 56 that includes four upstanding angled caming surfaces 150a, 150b, 150c, 150d. An asymmetrical staple cartridge according to the present invention will have a slider 56 that corresponds to the number of staple rows on each side of the I-beam blade 42. Two angled caming surfaces 150a, 150b are separated by an I-beam receiving portion 152 from the two angled caming surfaces 150c, 150d. The I-beam receiving portion 152 is sized and configured to receive the middle portion 38 of the I-beam 32. Each caming surface 150 is approximately 0.005 inches thick and includes an angled distal end. The angle of the caming surface 150 corresponds to the angle of the staple holding locations 92 and 124 which ranges from approximately 30-90 degrees wherein 90 degrees is a vertical caming surface 150. The slider 56 is disposed inside the lower jaw 50 inside a lower passageway defined between the one or more staple cartridges 52 and the bottom cover 74. The slider 56 is retained in the lower jaw 50 between the one or more staple cartridges 52 and bottom cover 74 yet the slider 56 is free to translate longitudinally distally and proximally with respect to the lower jaw 50. The upwardly extending caming surfaces 150a and 150b extend upwardly through slots 120 and 122, respectively, of the staple cartridge 52 on one side of the blade 42 of the I-beam 32. The other two upwardly extending caming surfaces 150c and 150d extend upwardly through slots 120 and 122, respectively, of the other side of the staple cartridge 52 or second staple cartridge 52 on the other side of the blade 42 of the I-beam 32. The slider caming surfaces 150 are configured to contact staples residing inside staple pockets 118 and sequentially urge them out towards the anvil surface 58 of the upper jaw 48 as the slider 56 translates along the end effector 18.

Turning now to FIGS. 31-34, a staple 54 according to the present invention will be described. The staple 54 is shown in its undeformed or open condition. The staple 54 includes a first leg 154 and a second leg 156 interconnected by a base 158. The first leg 154 intersects with the base 158 at approximately 90 degrees and defines a first intersection 160. The second leg 156 intersects with the base 158 at approximately 90 degrees and defines a second intersection 162. The first leg 154 is longer than the second leg 156. The staple 54 includes an inner surface 164 and an outer surface 166 interconnected by a first sidewall 168 and second sidewall 170. The inner surface 164 intersects with the outer surface 166 at a first point 172 at the first leg 154 and at a second point 174 at the second leg 156. The first point 172 and second point 174 are line intersections in FIG. 31 that are perpendicular to the length of the staple 54. In another variation, the line intersections are parallel to the length of the staple 54. In another variation, the first point 172 and/or the second point 174 are point intersections. In another variation, the first point 172 and/or second point 174 are planar surfaces or any other geometric shape that is suitable for puncturing and penetrating tissue through which the staple is delivered. The first leg 154 includes a first tip 176 at the free distal end of the first leg 154 and the second leg 156 includes a second tip 178 at the free distal end of the second leg 156. The first and second tips 176, 178 begin where the first and second legs 154, 156, respectively, begin to taper or decrease in cross-sectional area in the direction distally along the leg 154, 156.

Figure 32:
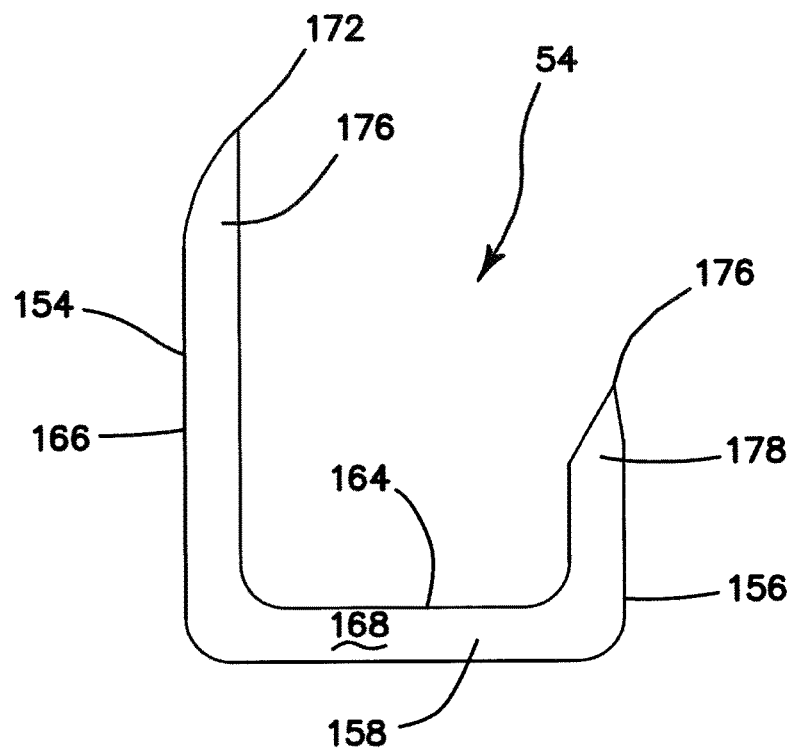
FIG. 32 is a side view of a staple according to the present invention.
Figure 33:
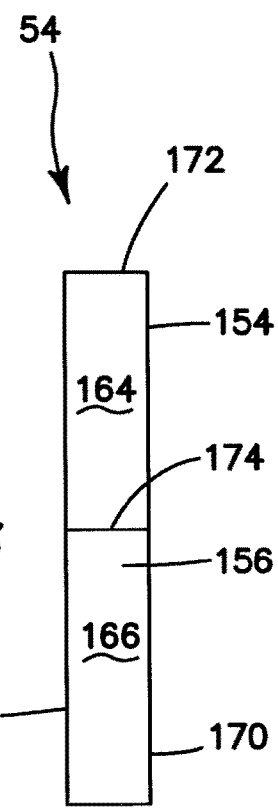
FIG. 33 is an end view of a staple according to the present invention.
Figure 34:
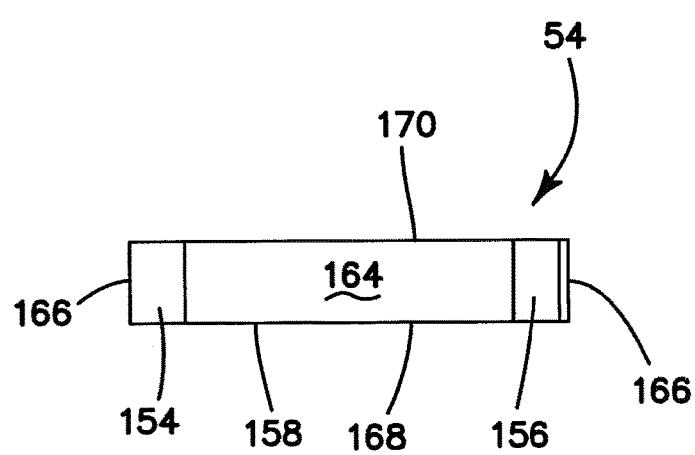
FIG. 34 is a top view of a staple according to the present invention.

With particular attention to FIGS. 32-34, the first leg 154 is approximately 0.097 inches long and the second leg 156 is approximately 0.050 inches long. The ratio of the shorter second leg 156 to the longer first leg 154 is approximately ½. The overall length of the base 158 is approximately 0.080 inches and each leg 154, 156 is perpendicular to the base 158. The radius of curvature of the outer surface 166 at the first and second intersections 160, 162 is approximately 0.009 inches. The distance between the first sidewall 168 and the second sidewall 170 or thickness of the staple is approximately 0.015 inches. The distance between the inner surface 164 and the outer surface 166 or width of the first and second legs 154, 156 is approximately 0.010 inches. The distance between the inner surface 164 and the outer surface 166 or width of the base 158 is also approximately 0.010 inches. The first tip 176 includes a curved outer surface 166 having a radius of curvature of approximately 0.034 inches. This curve forms a convex outer surface 166 in the location of the first tip 176. The inner surface 164 at the first tip 176 is perpendicular to the base 158 and intersects with the curved outer surface 166 at a line intersection defining the first point 172. The second tip 178 includes an angled outer surface 166. The portion of the outer surface 166 in the location of the second tip 178 is angled approximately 10 degrees from vertical towards the inner surface 164. The portion of the inner surface 164 in the location of the second tip 178 is angled approximately 30 degrees from vertical towards the outer surface 166. Together the angled outer surface 166 and the angled inner surface 164 in the location of the second tip 178 form an angle of approximately 40 degrees therebetween and define a line intersection at the second point 174.

Figure 35:
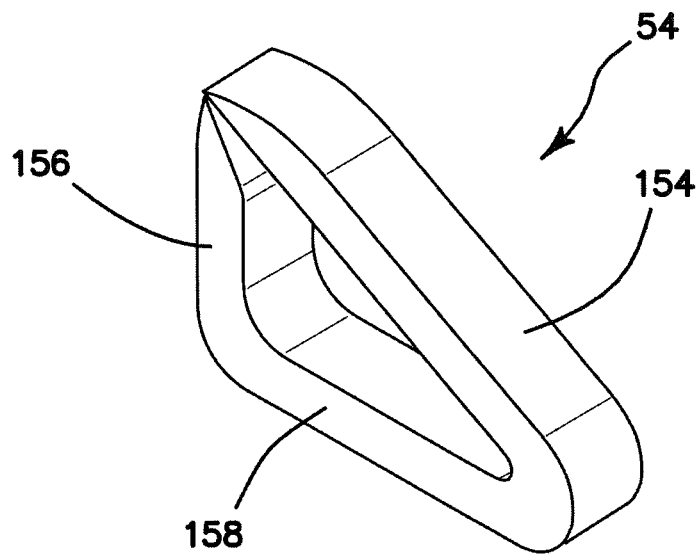
FIG. 35 is a top perspective view of a staple in a closed configuration according to the present invention.
Figure 36:
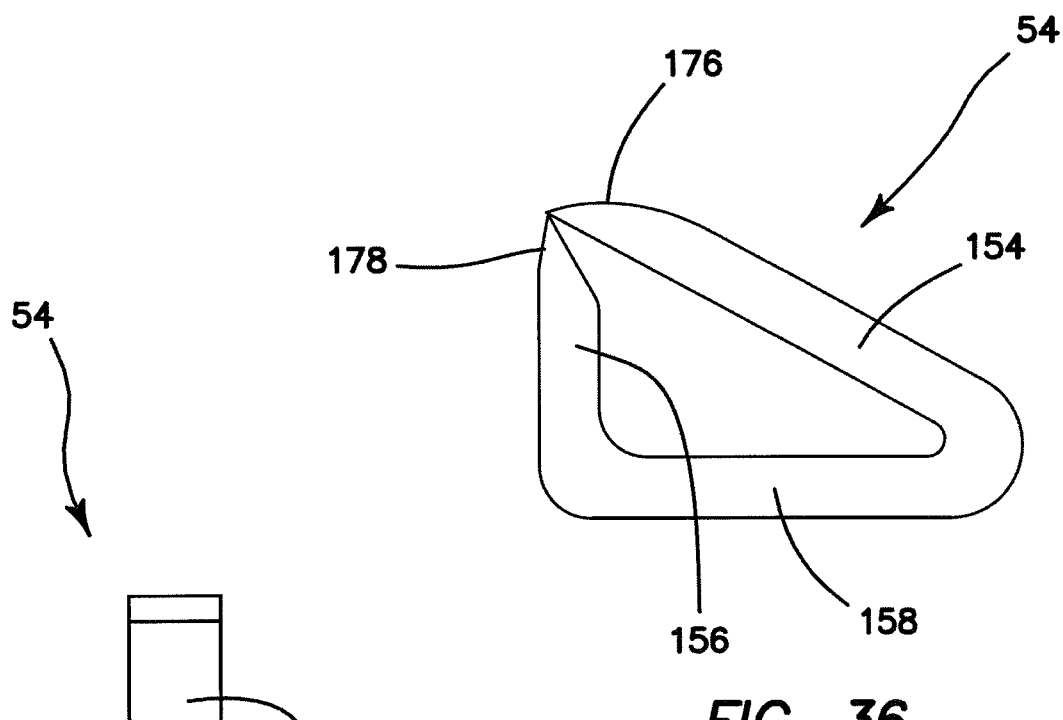
FIG. 36 is a side elevational view of a staple in a closed configuration according to the present invention.
Figure 37:
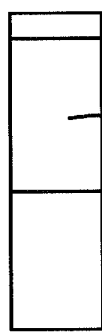
FIG. 37 is an end view of a staple in a closed configuration according to the present invention.
Figure 44A:
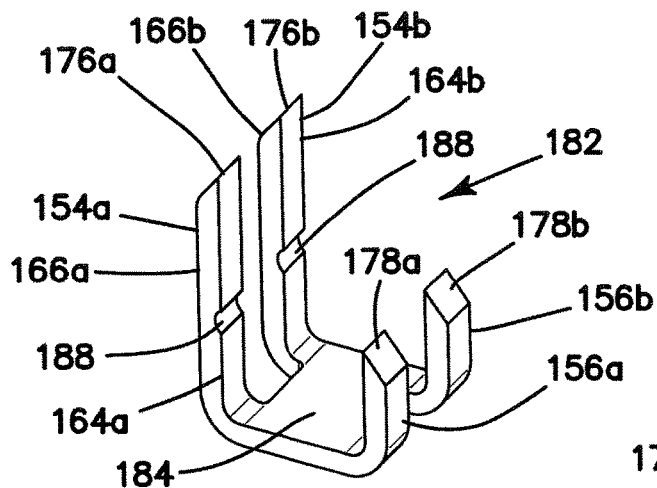
FIG. 44A is a top perspective view of a four-pronged staple according to the present invention.
Figure 44B:
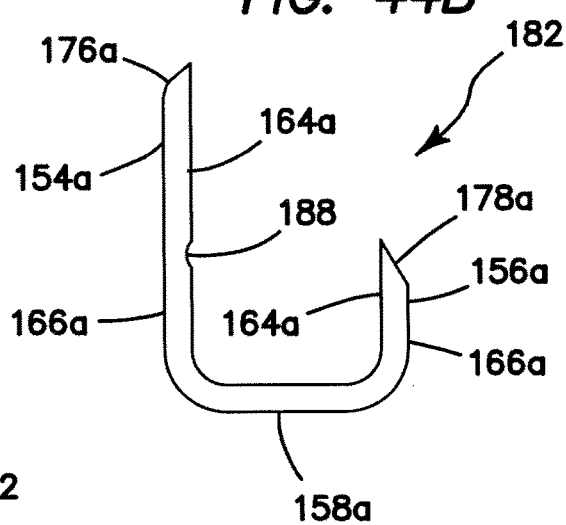
FIG. 44B is a side elevational view of a four-pronged staple according to the present invention.
Figure 44C:
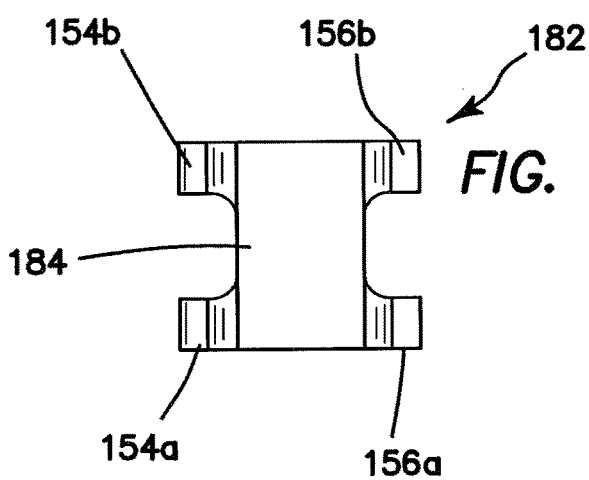
FIG. 44C is a top view of a four-pronged staple according to the present invention.
Figure 44D:
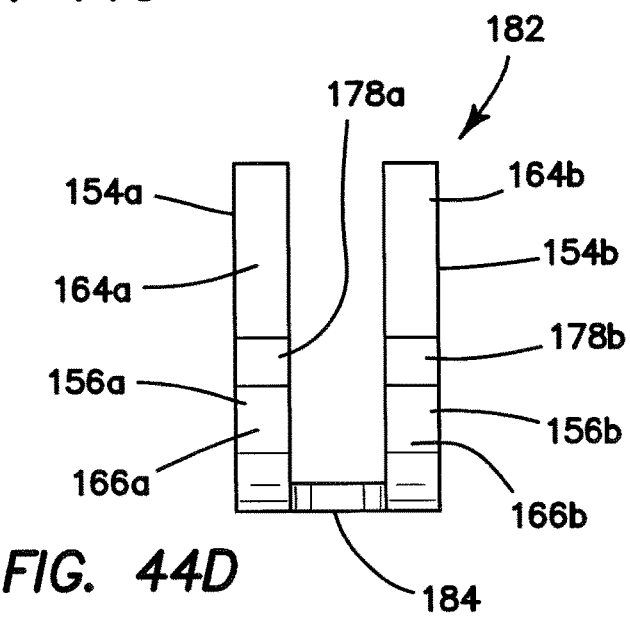
FIG. 44D is an end view of a four-pronged staple according to the present invention.
Figure 45A:
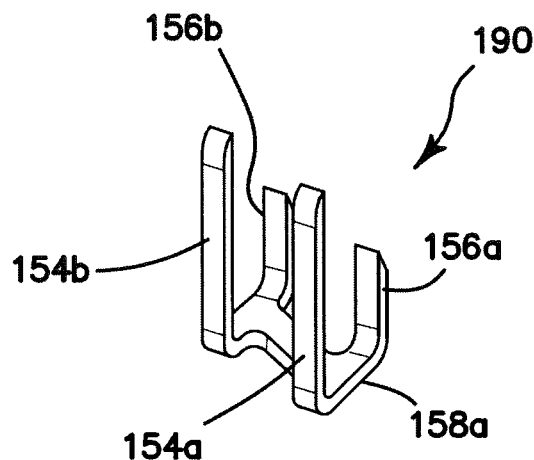
FIG. 45A is a top perspective view of a four-pronged staple according to the present invention.
Figure 45B:
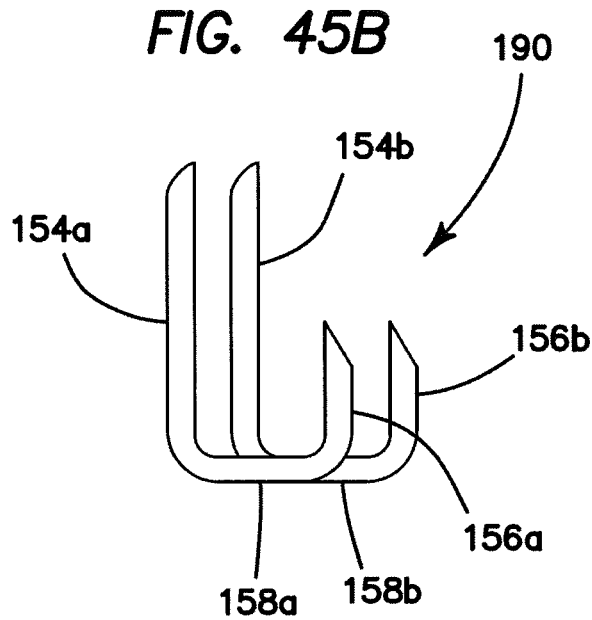
FIG. 45B is a side elevational view of a four-pronged staple according to the present invention.
Figure 45C:
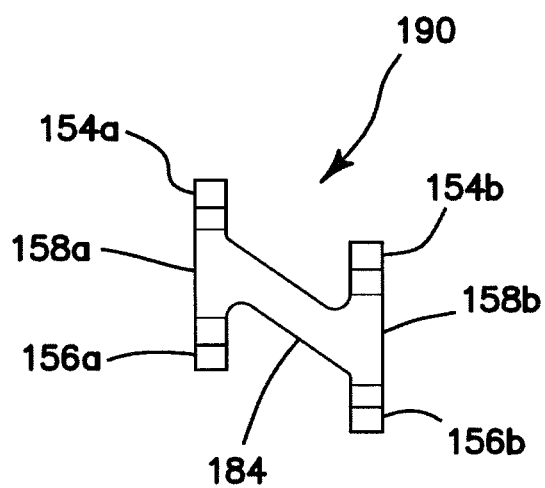
FIG. 45C is a top view of a four-pronged staple according to the present invention.
Figure 45D:
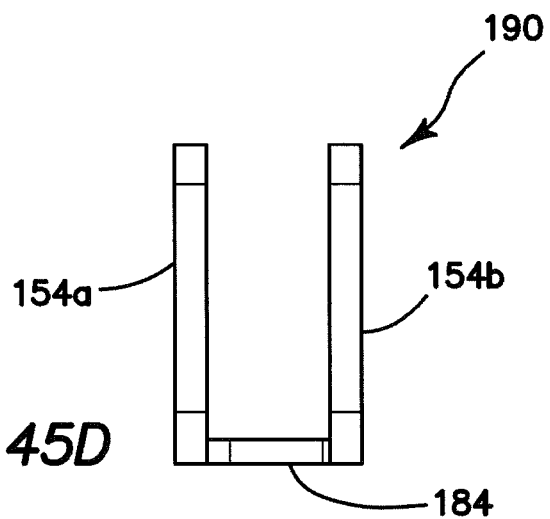
FIG. 45D is an end view of a four-pronged staple according to the present invention.
Figure 46A:
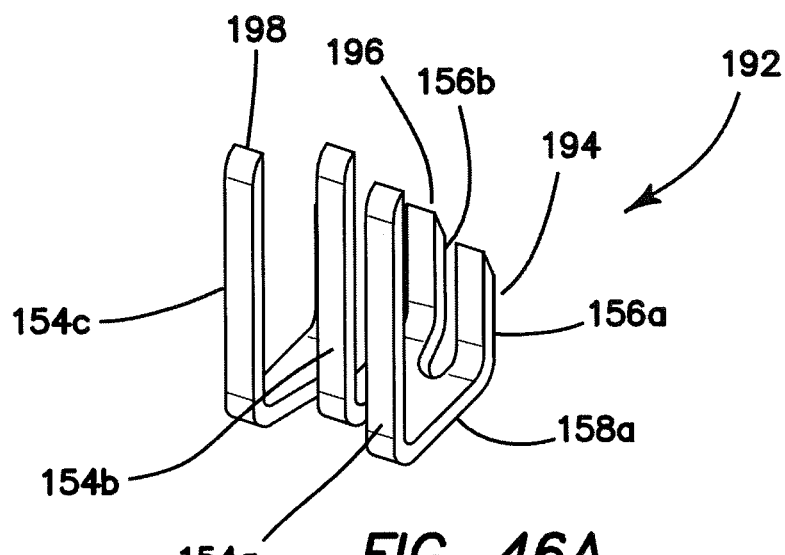
FIG. 46A is a top perspective view of a six-pronged staple according to the present invention.
Figure 46B:
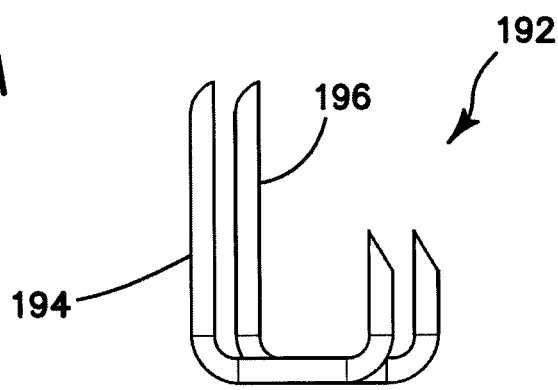
FIG. 46B is a side elevational view of a six-pronged staple according to the present invention.
Figure 46C:
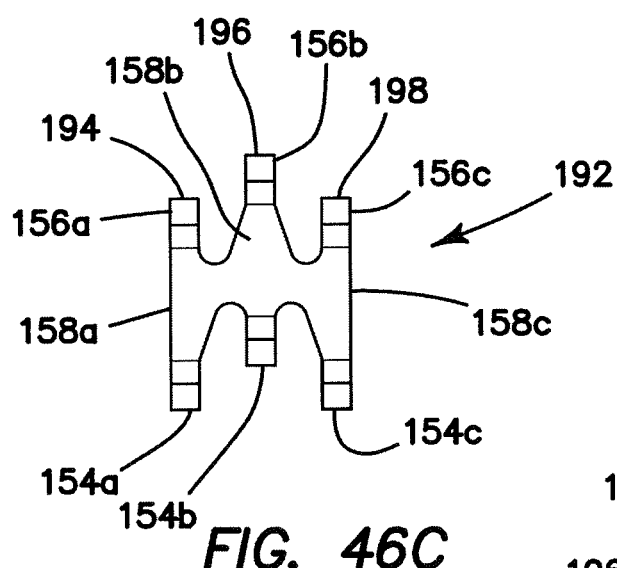
FIG. 46C is a top view of a six-pronged staple according to the present invention.
Figure 46D:
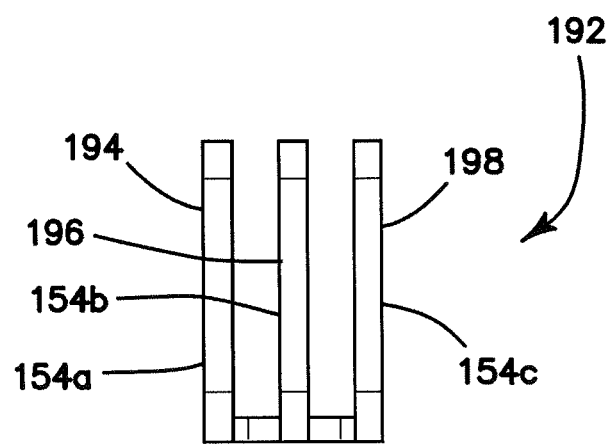
FIG. 46D is an end view of a six-pronged staple according to the present invention.

With particular attention to FIGS. 35-37, the staple 54 is shown in its deformed or closed configuration in which the first leg 154 is angled towards the second leg 156 to form a triangular shape or delta or D-shaped configuration. The triangular shape results when the first leg 154 is deformed as a result of urging the undeformed staple 54 from staple pockets 118 in the lower jaw 50 against the anvil surface 58 of the upper jaw 48 of the stapler 10 of the present invention. In this delta configuration, the second leg 156 remains upstanding and substantially perpendicular to the base 158 and the first leg 154 is deflected to towards the second leg 156 until the first and second tips 176, 178 meet or are substantially in juxtaposition to each other. The resulting angle of the deflected first leg 154 with respect to the base 158 is approximately 29 degrees. In one variation, the staple has a circular cross-section. In another variation of the staple 54, a stress concentration is formed in the first leg 154 to create a weaker location in the first leg 154 so that deformation, bending or deflection of the first leg 154 takes place in the location of the stress concentration. An example of a stress concentration is at least one notch formed in the inner surface 164 at a location along the first leg 154 to encourage bending of the first leg 154 to occur at the stress concentration. An example of stress concentration in the form of a notch 188 is shown in FIGS. 44A and 44B. In another variation, stress concentrations such as one or more notches are strategically placed to effect a variety of closed staple shapes. For example, closed staple shapes are not limited to a triangular shaped staple but also include rectangular, square, rhombus, and trapezoid shapes. Furthermore, in another variation, notches are formed to capture one leg inside the notch formed in the opposite staple leg to create a locking variant in which the closed staple shape includes interlocked first and second legs configured resist forces that would open the staple from a closed and interlocked configuration.

Figure 38:
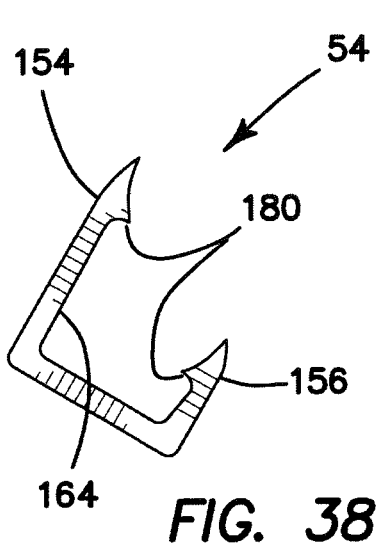
FIG. 38 is a side view of a staple with barbs according to the present invention.
Figure 39:
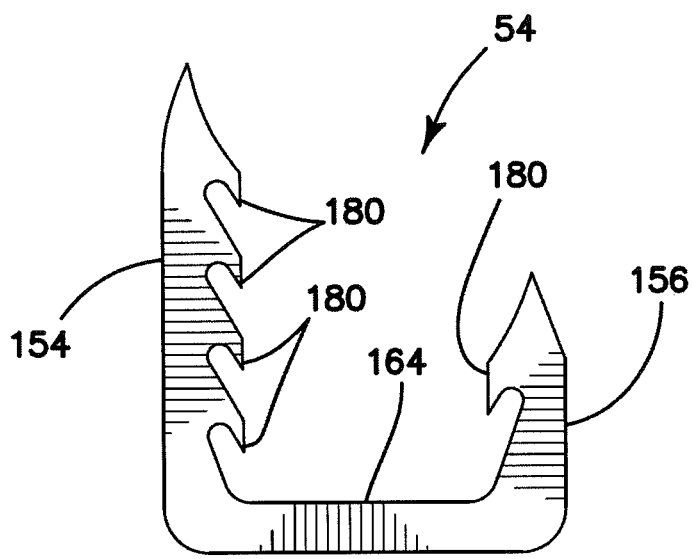
FIG. 39 is a side view of a staple with barbs according to the present invention.

Turning to FIGS. 38-39, the staple 54 is shown to include at least one barb 180. In the variation shown in FIG. 38, a single barb 180 is provided near the distal end of each leg 154, 156 formed in the inner surface 164 of the staple 54. Barbs assist in providing an increased mechanical hold of the staple into tissue and can be formed on either or both legs and on the inner surface 164 or outer surface 166. Multiple barbs 180 along one of the legs are shown in FIG. 39. In FIG. 39, four barbs 180 are formed in the inner surface of the first leg 154 and one barb 180 is formed in the inner surface of the second leg 156. Smaller barbs 180 such as micro and nano sized barbs are also within the scope of the present invention.

Figure 40:
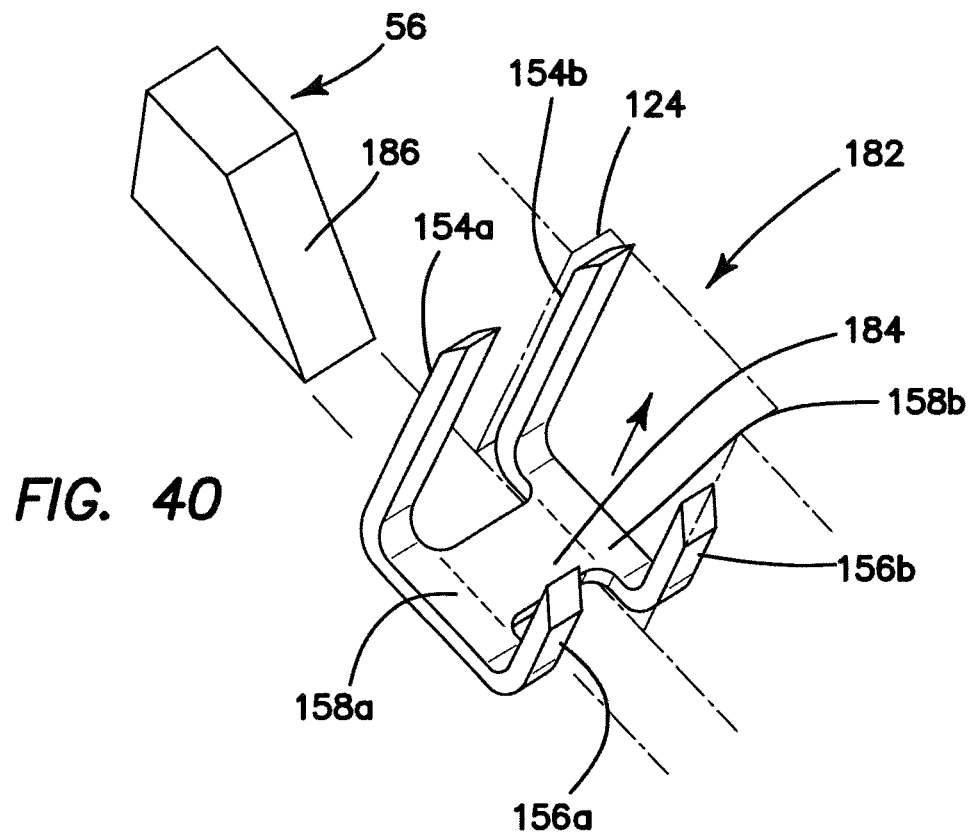
FIG. 40 is a top perspective sectional view of a four-pronged staple in a staple pocket, and a slider according to the present invention.
Figure 41:
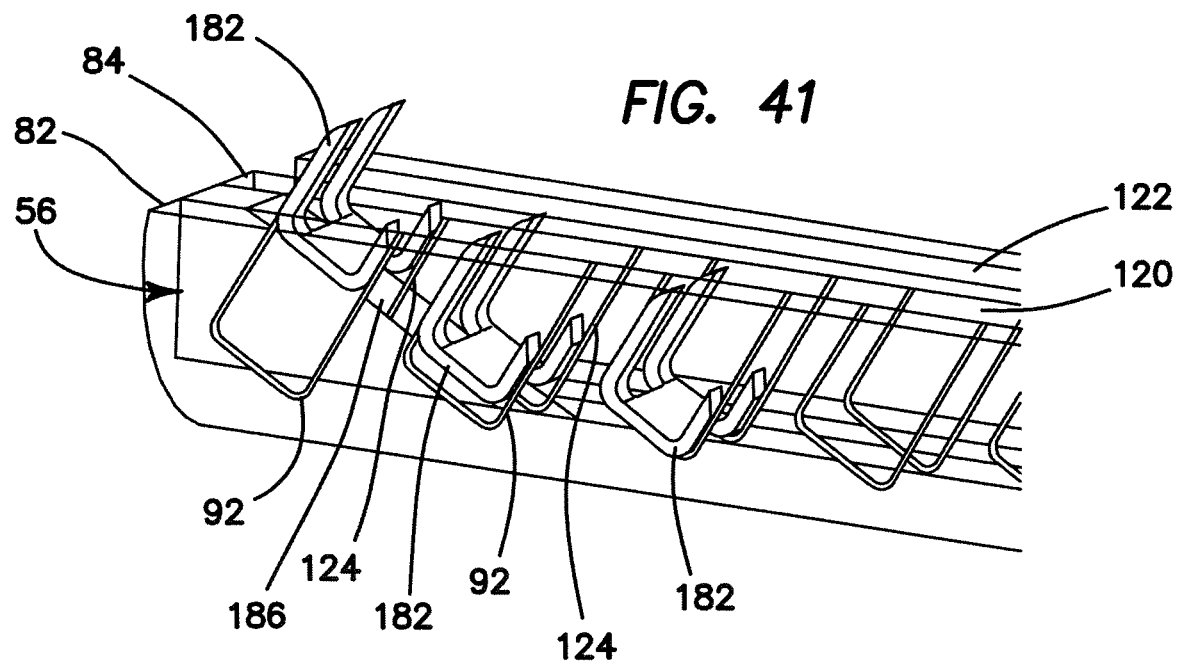
FIG. 41 is a semi-transparent, top perspective, sectional view of a slider and a plurality of four-pronged staples loaded in a lower jaw and a slider according to the present invention.
Figure 42A:
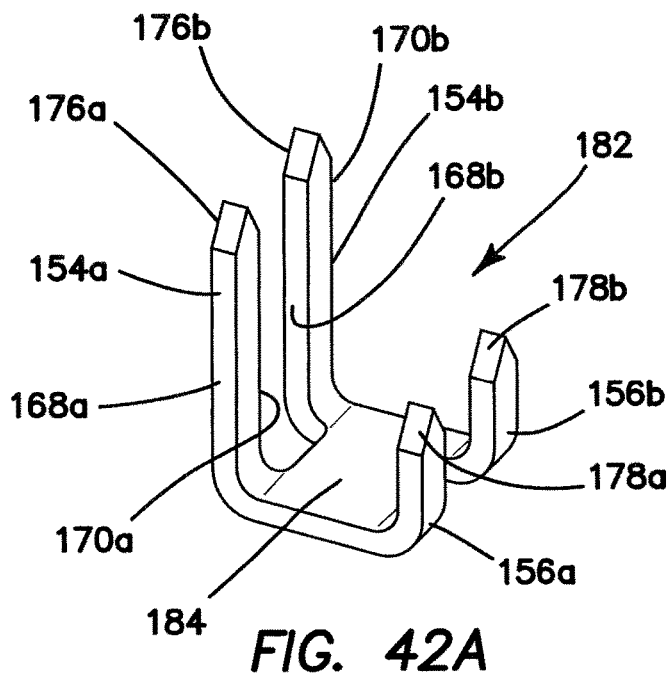
FIG. 42A is a top perspective view of a four-pronged staple according to the present invention.
Figure 42B:
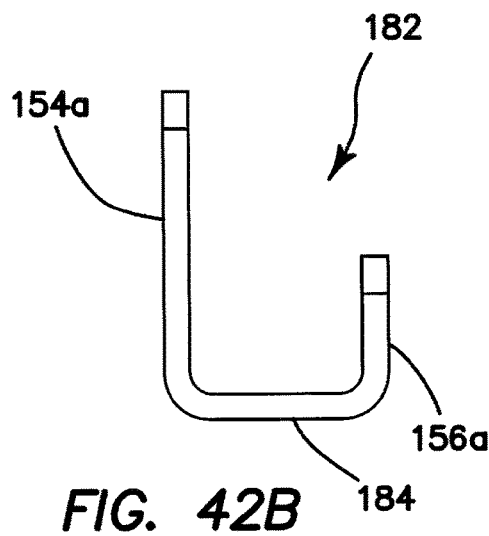
FIG. 42B is a side elevational view of a four-pronged staple according to the present invention.
Figure 42C:
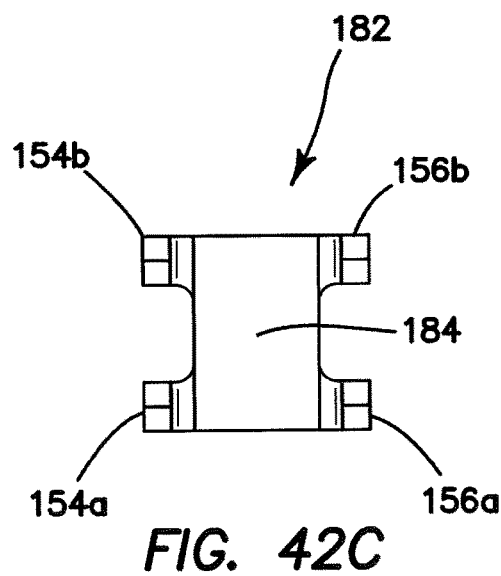
FIG. 42C is a top view of a four-pronged staple according to the present invention.
Figure 42D:
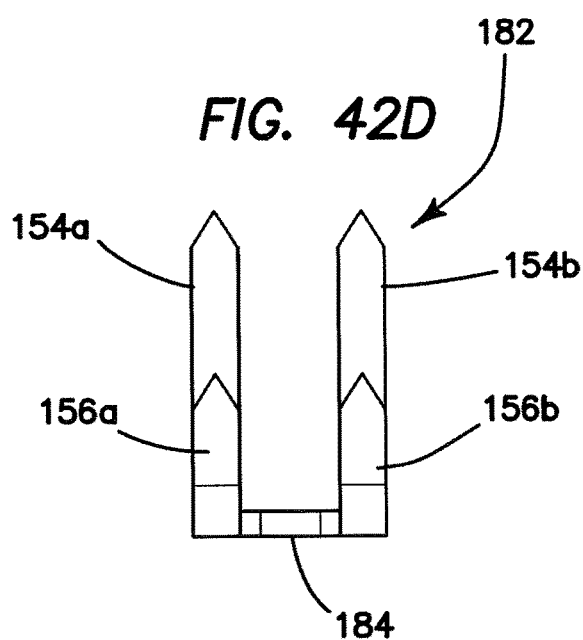
FIG. 42D is an end view of a four-pronged staple according to the present invention.

Turning now to FIGS. 40-41, there is shown a four-pronged staple 182. The four-pronged staple 182 includes a longer first leg 154a interconnected to a shorter second leg 156a by a base 158a and a second longer first leg 154b interconnected to a shorter second leg 156b by a base 158b. Each pair of staple legs 154a, 156a and 154b, 156b and their interconnected bases 158a, 158b are substantially identical to the staple 54 depicted and described with respect to FIGS. 31-37, except in the four-pronged staple 182 the two pairs of legs are interconnected by a enlarged base portion 184 that has the same thickness as staple bases 158a, 158b which are approximately 0.010 inches thick. The enlarged base portion 184 is connected to base 158a and base 158b and serves as a caming surface for engagement with a slider 56 that includes an enlarged angled slider caming surface 186. The staple cartridge 52 is still formed in a similar manner as described with respect to FIGS. 17-22 except that it is adapted to receive a wider staple having wider slots 120, 122 to accommodate the wider four-pronged staple 182 and wider slider 56. The cartridge 52 adapted for the four-pronged staple 182 is preferably similar to that described with respect to FIG. 22 in which the first plate 82 and second plate 84 include oppositely formed angled staple holding locations 92, 124, respectively. At least a portion of the first leg 154a, second leg 156a and base 158a is disposed in the staple holding location 92 of the first plate 82 and at least a portion of the first leg 154b, second leg 156b and base 158b is disposed in the staple holding location 124 of the second plate 84. An additional third plate 86 may hold another row of four-pronged staples 182 between the third plate 86 and second plate 84 as described above with another slider caming surface 186 residing in the second slot 122. The four-pronged staples 182 are angled to match the angle of the slider 56 caming surface 186 such that when the slider 56 is pushed forward by the translating I-beam 32, the angled slider caming surface 186 contacts the enlarged base portion 184 of the staple 182 to urge the staple 182 upwardly and out of the cartridge 52 and against the anvil surface 58 of the upper jaw 48 where the staple 182 is deformed into tissue. The deformed staple includes two triangular shaped closures wherein the first legs 154a, 154b are bent towards the second legs 156a, 156b, respectively.

Figure 43A:
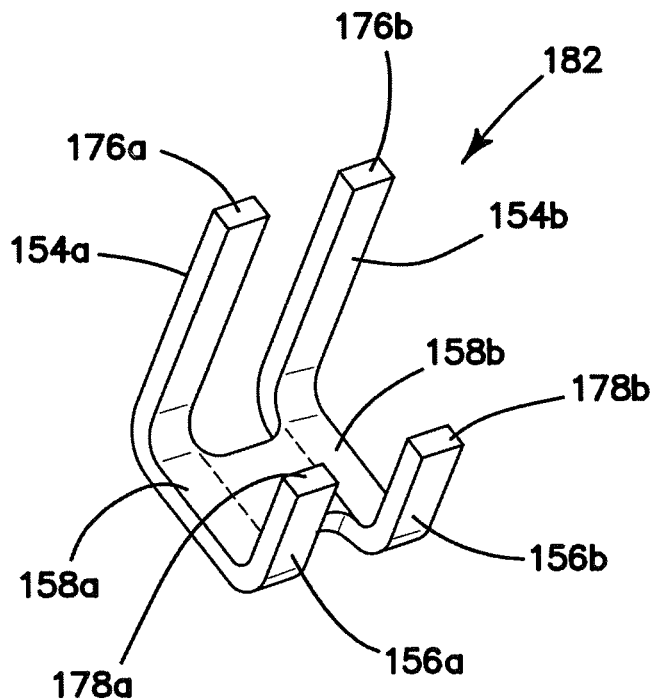
FIG. 43A is a top perspective view of a four-pronged staple according to the present invention.
Figure 43B:
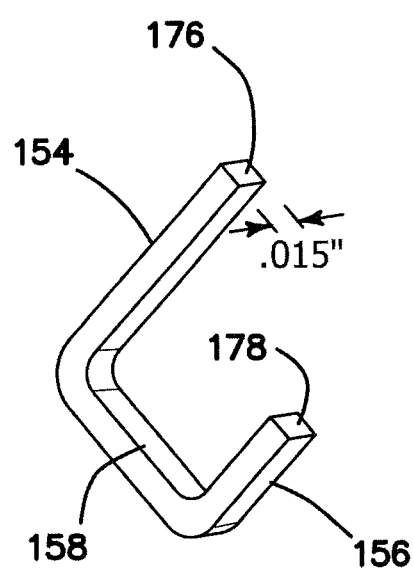
FIG. 43B is a top perspective view of a staple according to the present invention.

FIGS. 42A-42D illustrate various views of a four-pronged staple 182 that includes an even larger base portion 184 to provide additional strength to the staple 182. The first and second tips 176a, 176b, 178a, 178b include angled first and second sidewalls 168a, 168b, 170a, 170b to form line intersections that are parallel to the length of the staple 182. A four-pronged staple 182 having flat, blunt first tips 176a, 176b and second tips 178a, 178b are shown in FIG. 43A. The four-pronged staple 182 of FIG. 43A may be cut along dotted lines to form two single staples 54 having only two legs 154, 156 each with flat first and second tips 176, 178 as shown in FIG. 43B.

Turning now to FIGS. 44A-44D, there is shown a four-pronged staple 182 having notches 188 formed in the inner surface of first legs 154a, 154b. The notches 188 are curved semi-cylindrically shaped indentations that create stress concentrations in the legs 154a, 154b such that while being deformed the legs 154a, 154b will tend to bend in the location of the notches 188. In the variation of the four-pronged staple 182 of FIGS. 44A-44D, the first tips 176a, 176b include curved outer surfaces 166a, 166b intersecting with straight inner surfaces 164a, 164b to form line intersections that are perpendicular to the length of the staple 182. The second tips 178a, 178b are formed by angled outer surfaces 166a, 166b intersecting with straight inner surfaces 164a, 164b to form line intersections that are perpendicular to the length of the staple 182. When deformed, the first legs 154a, 154b are bent at the notches 188 such that first tips 176a, 176b contact second tips 178a, 178b to form two connected triangular shaped closures.

With reference to FIGS. 45A-45D, a four-pronged staple 190 having staggered legs is shown. A first two-pronged staple having a longer first leg 154a interconnected to a shorter second leg 156a by a base 158a is connected via an angled enlarged planar base portion 184 to a second two-pronged staple having a longer first leg 154b interconnected to a shorter second leg 156b by a base 158b such that the first two-pronged staple is offset or staggered with respect to the second two-pronged staple. The first and second two pronged staples are substantially identical to the staple described above with respect to FIGS. 31-37. The angled base portion 184 interconnecting the two two-pronged staples allows the first two-pronged staple to be offset from the second two-pronged staple resulting in a four-pronged staple 190 with staggered legs 154a, 154b, 156a, 156b. The enlarged base portion 184 serves as a caming surface for caming against the angled caming surface 150 of the slider 56. When actuated the two longer first legs 154a, 154b are deformed against the anvil surface 58 towards the second legs 156a, 156b, respectively, to form two triangular shaped closures capturing tissue therebetween. When an entire row of four-pronged staples 190 are deployed, the result is two effective rows of staggered staples.

Turning now to FIGS. 46A-46D, there is shown a six-pronged staple 192. The six-pronged staple 192 includes a first two-pronged staple 194 connected to a second two-pronged staple 196 connected to a third two-pronged staple 198 in a staggered fashion. The first, second and third two-pronged staples 194, 196, 198 are substantially identical to the two pronged staple 54 of FIGS. 31-37 described above. The first two-pronged staple 194 includes a longer first leg 154a interconnected to a shorter second leg 156a by a base 158a. The second two-pronged staple 196 includes a longer first leg 154b interconnected to a shorter second leg 156b by a base 158b. The third two-pronged staple 196 includes a longer first leg 154c interconnected to a shorter second leg 156c by a base 158c. Each of the two-pronged staples 194, 196, 198 is connected to each other at their bases 158a, 158b, 158c, respectively. The first two-pronged staple 194 is connected to the second two-pronged staple 196 by an angled extended base portion therebetween such that the first two-pronged staple 194 is offset from the second two-pronged staple 196. The second two-pronged staple 196 is connected to the third two-pronged staple 198 by an angled extended base portion therebetween such that the second two-pronged staple 196 is offset from the third two-pronged staple 198. The three two-pronged staples 194, 196, 198 are connected such that the first and third two-pronged staples 194, 198 are in alignment with respect to each other and the middle second two-pronged staple 196 is offset relative to the first and third two-pronged staples 194, 198. The six-pronged staple 192 is loaded in an angled manner into a cartridge as described above with respect to FIGS. 22, and 40-41 wherein the first two-pronged staple 194 is disposed at least in part into a staple holding location 92 of the first plate 82 and the third two-pronged staple 198 is disposed at least in part into a staple holding location 124 of the second plate 84 such that the middle or second two-pronged staple 196 resides inside the first slot 120 together with a slider 56 having an enlarged caming surface 186 of the like described with respect to FIGS. 40-41 against which the base portions engage for deployment. Of course a third-plate 86 with staple holding locations 92 is loaded with staples 192 in the same manner for engagement with a second slider 56 residing inside the second slot 122. After the six-pronged staple 192 is urged by the slider against the anvil surface 58, the first legs 154a, 154b, 154c are deflected towards the second legs 156a, 156b, 156c, respectively, to form three triangular shaped closures that capture tissue. These three triangular shaped closures are staggered with respect to each other yet interconnected to form a wide and strong stapling of tissue.

Figure 47A:
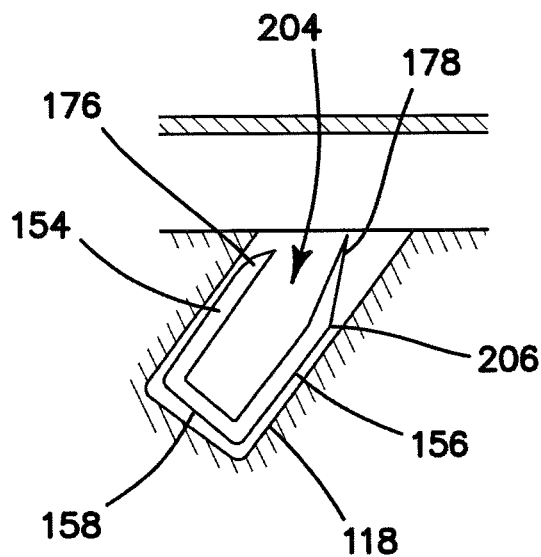
FIG. 47A is a side sectional view of a staple inside a staple pocket of a lower jaw and an upper jaw according to the present invention.
Figure 47B:
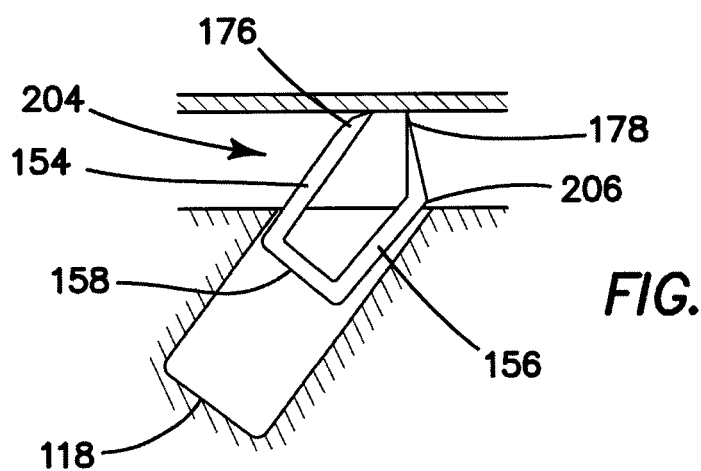
FIG. 47B is a side sectional view of a staple contacting the upper jaw according to present invention.
Figure 47C:
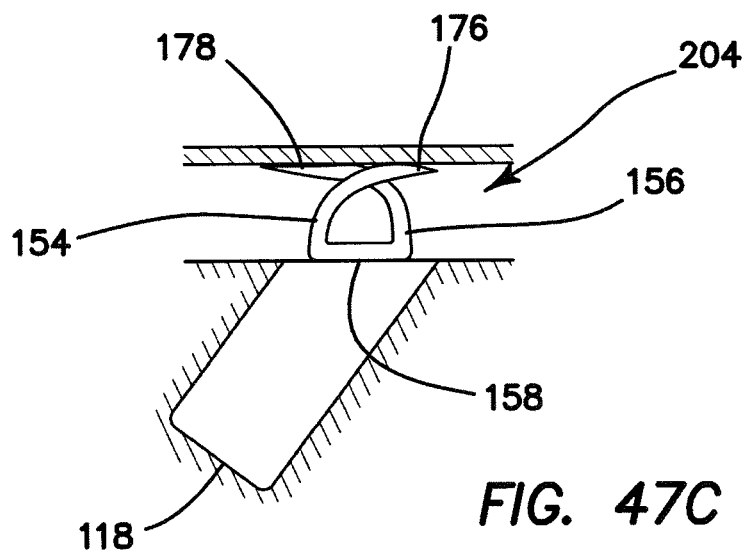
FIG. 47C is a side sectional view of a staple contacting the upper jaw and deforming according to the present invention.

Referring now to FIGS. 47A-47C, another staple variation is shown. In this variation, the staple 204 includes a first leg 154 interconnected to a second leg 156 by a base 158. The first leg 154 is substantially straight when undeformed and includes a first tip 176 having an angled or chamfered outer surface. The second leg 156 is slightly longer than the first leg 154. The second leg 156 also includes an elbow 206 at which the second leg 156 is bent slightly towards the first leg 154 while in the undeformed condition as shown in FIGS. 47A-47B. The second leg 156 includes a second tip 178 which in one variation commences to taper from the elbow 206. Since the staple 204 is disposed inside a cartridge at an angle as described above, when the staple 204 is urged upwardly by an advancing slider (not shown), both the first and second tips 176 and 178 contact the flat anvil surface 58 substantially simultaneously as shown in FIG. 47B. Continued urging of the staple 204 into the anvil surface 58 results in the first leg 154 bending towards the second leg 156 and the second leg 156 bending towards the first leg 154 as shown in FIG. 47C. The angled or chamfered outer surface at the first tip 176 assists in directing the first leg 154 towards the second leg 156. The elbow 206 and angled second leg 156 assist in directing the second leg 156 towards the first leg 154. Because the staple pockets 118 retain the staples 204 at an angle to the flat anvil surface 58, the second leg 156 has to be slightly longer and angled such that the portion of the second leg 156 that is distal to the elbow 206 is substantially perpendicular to the flat anvil surface 58 when the second tip 178 contacts the flat anvil surface 58. This variation advantageously does not require anvil pockets formed in the anvil surface and precise alignment of the staple legs 154, 156 with anvil pockets to effect deflection of staple legs 154, 156 towards each other. Such deflection is accomplished against a flat anvil surface 58.

Figure 48:
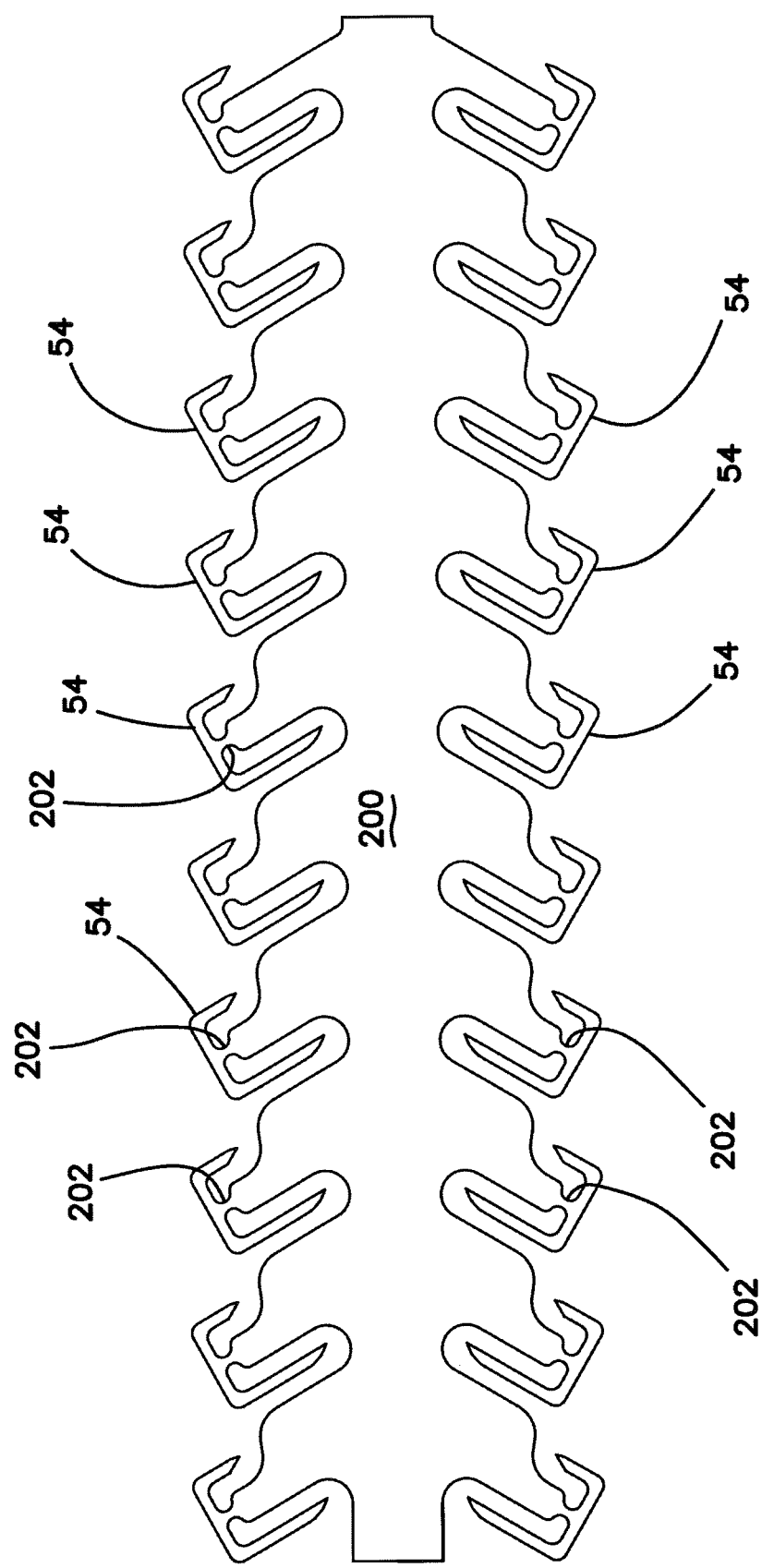
FIG. 48 is a top view of a plurality of staples connected to a backbone according to the present invention.

With reference to FIG. 48, there is shown a plurality of staples 54 connected to a backbone 200 illustrating the formation of staples 54 in a fishbone style for ease of manufacturing, assembly and handling. A sheet of metal such as surgical steel, stainless steel, or titanium is provided and a plurality of staples 54 is cut into the sheet of metal on a wire electrical discharge machining (EDM) machine. The staples 54 may also be formed utilizing a micro-water jet, photo etching or by stamping. The staples 54 remain connected to the backbone 200 via narrow connecting tabs 202 until the staples 54 are broken off at the tabs 202 and then loaded into a staple cartridge. After a staple 54 is broken off a portion of the connecting tab 202 remains attached to the staple 54. The remnant tab 202 serves as a barb 180 for increasing mechanical holding onto tissue captured inside a closed staple 54 after deployment. Therefore, the staple 54 is manufactured without the need for post-processing such as bending and sharpening. Also, the backbone 200 can be an aid in the storage of staples 54 and in the assembly of staple cartridges.

Figure 49:
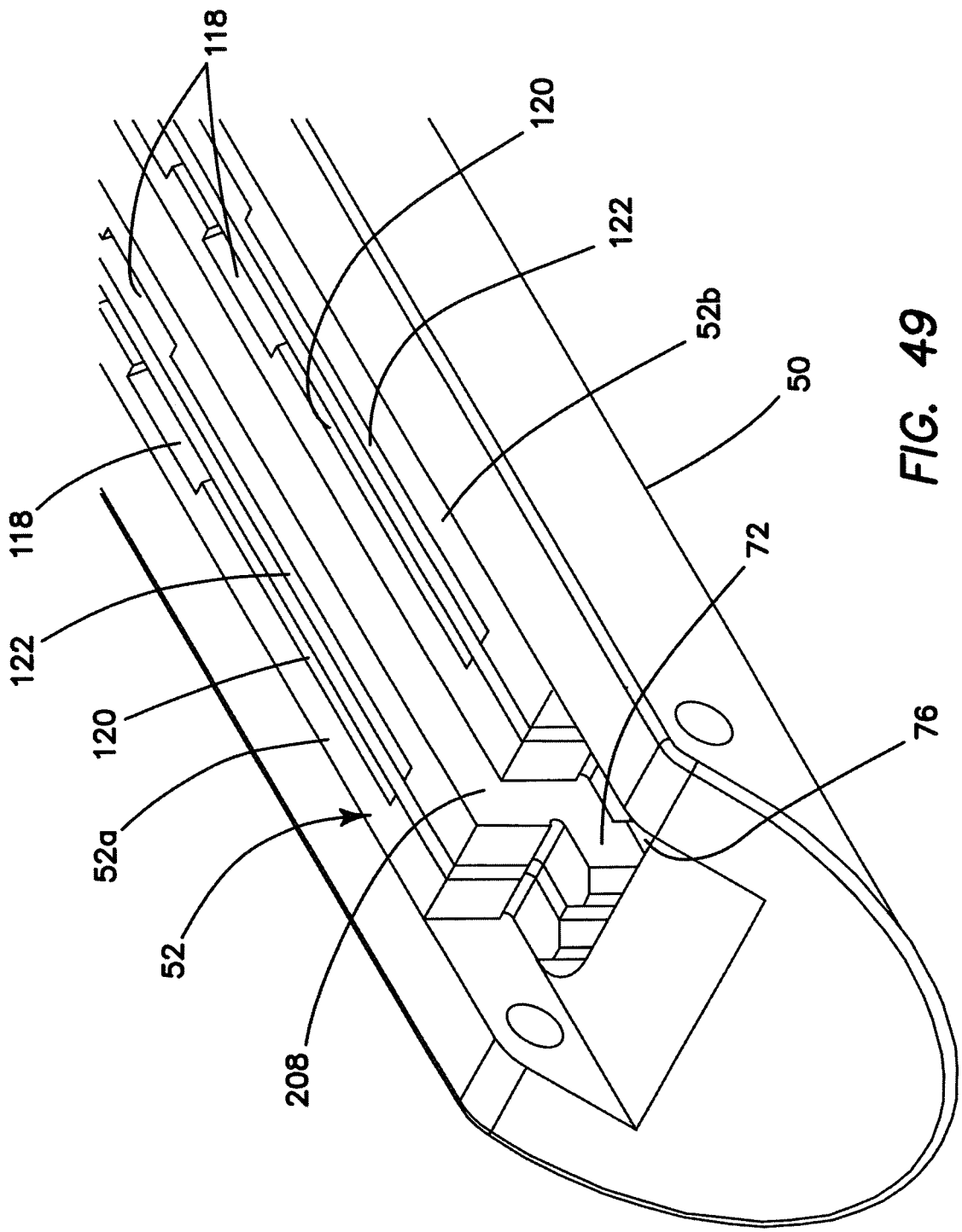
FIG. 49 is a top perspective view of a staple cartridge inserted in a lower jaw according to the present invention.
Figure 50:
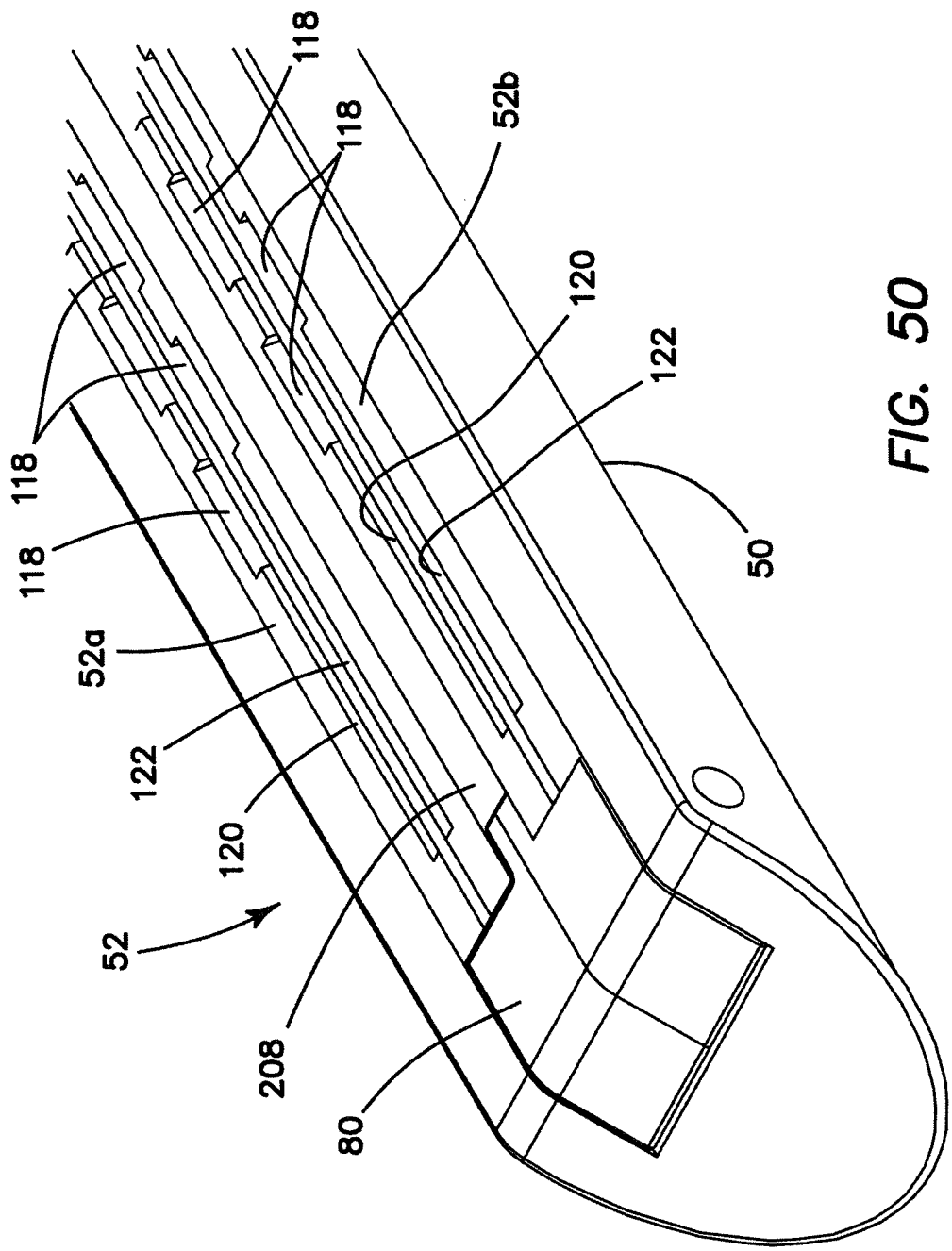
FIG. 50 is a top perspective view of a staple cartridge inserted in a lower jaw according to the present invention.

Turning to FIGS. 49-50, a staple cartridge 52 in the form of a single unit is inserted into the staple cartridge receiving portion 72 of the lower jaw 50. The staple cartridge 52 may also be in the form of two units 52a, 52b with each unit having two slots 120, 122 with two rows of staples 54 residing inside staple pockets 118. An asymmetrical cartridge as described above can also be employed. The staple cartridge 52 is inserted such that the grooves 104, 108, 116 of first, second and third plates 82, 84, 86, respectively, engage the tongue 78 at the proximal end of the lower jaw 50 and the tongues 102, 106, 114 of the first, second and third plates 82, 84, 86, respectively, engage the ledge 76 at the distal end of the lower jaw 50. A cartridge retainer 80 is connected covering the tongues 102, 106, 114 as shown in FIG. 50 to secure the cartridge in position. Each cartridge 52 can include a cover slip of paper (not shown) covering the staple pockets 118 to retain the staples 54 inside the pockets 118 during storage and handling. The cover slip is then removed by peeling away just prior to or after installation of the cartridge 52. Each cartridge 52 also contains a slider 56 disposed inside the cartridge 52 such that the angled caming surfaces 150a, 150b of the slider 56 reside in slots 120, 122, respectively on one side of the I-beam receiving portion 152 and the angled caming surfaces 150c, 150d of the slider 56 reside in slots 120, 122, respectively on the other side of the I-beam receiving portion 152. One side of the cartridge 52a is spaced apart from the other side of the cartridge 52b to create a central passageway 208 to allow passage of the translating I-beam 32.

Figure 51:
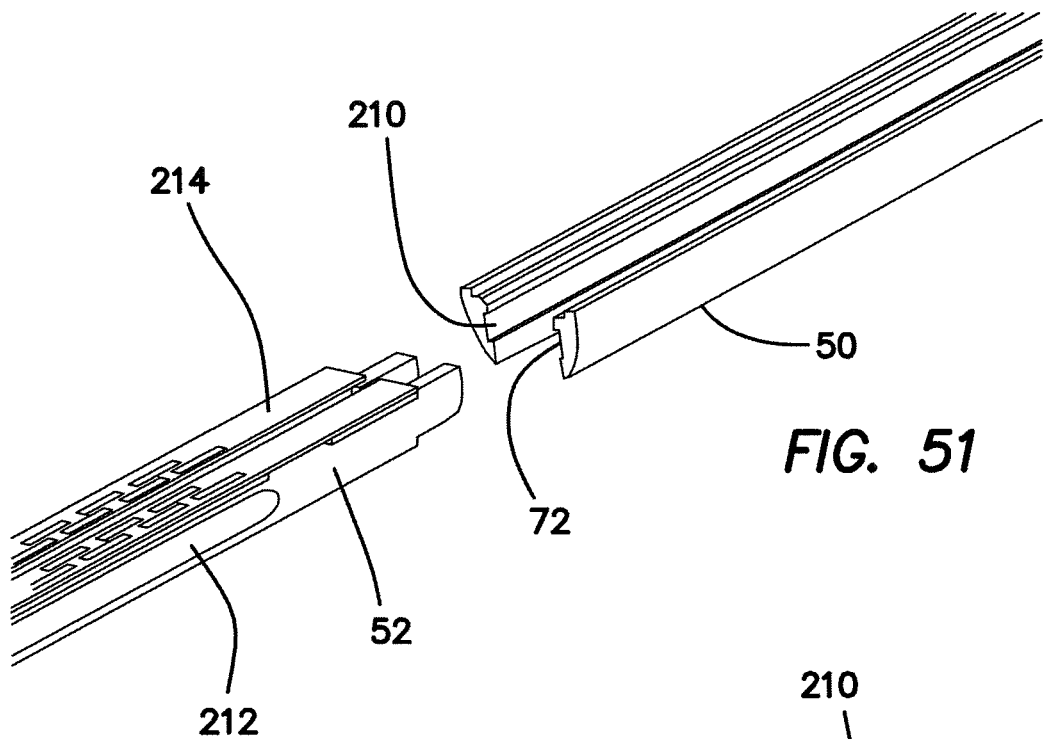
FIG. 51 is a top perspective view of a staple cartridge being inserted into a lower jaw according to the present invention.
Figure 52:
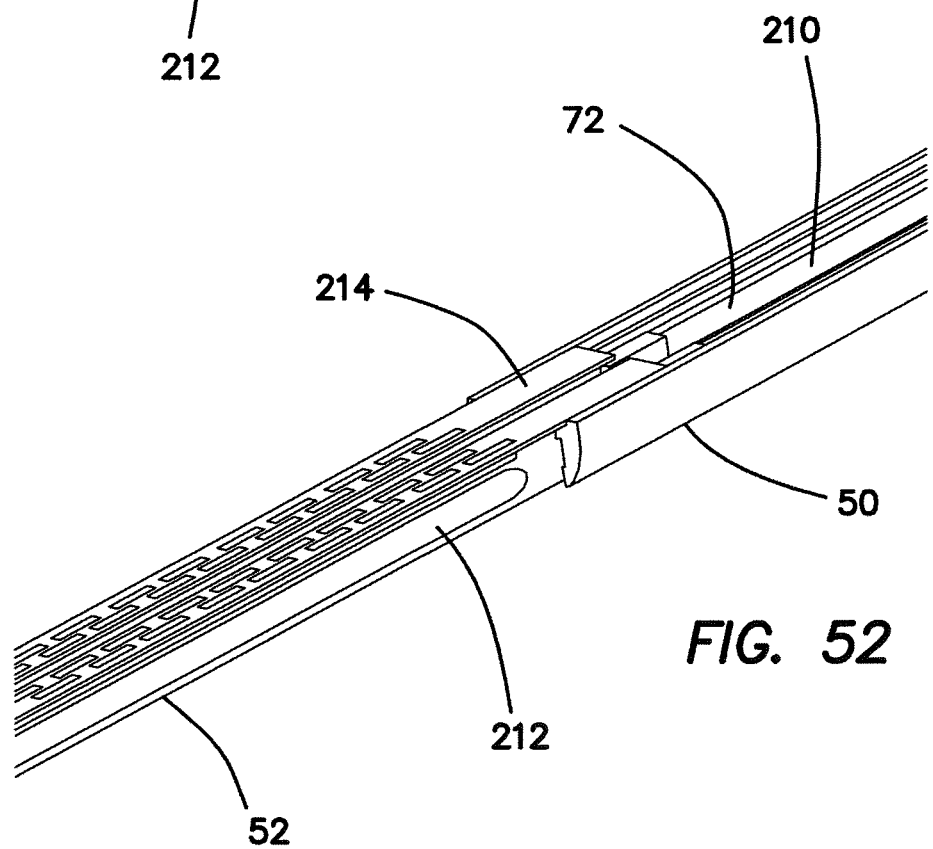
FIG. 52 is a top perspective view of a staple cartridge being inserted into a lower jaw according to the present invention.

Another variation of cartridge 52 installation is shown in FIGS. 51-52. In this variation, the front or distal end of the lower jaw 50 is open and the cartridge 52 includes rails 212 that engage tracks 210 formed in the staple cartridge receiving portion 72 of the lower jaw 50. The cartridge 52 slides in through the open distal end of the lower jaw 50 which is then closed with a cap or latch (not shown). The cartridge 52 is shown to include a top plate 214 which increases the strength across the width of the device. After the staples 54 are expended, the staple cartridge 52 can be removed and disposed and a new cartridge inserted for continued stapling. In another variation, the staple cartridge 52 is pre-installed inside the stapler cartridge assembly 14 and after the staples 54 are expended the entire stapler cartridge assembly 14 is removed and disposed and a new stapler cartridge assembly 14 is connected to the handle assembly 12 for continue stapling.

With the stapler cartridge assembly 14 connected to the handle assembly 12, the actuator shaft 22 connects to the actuator shaft 216 inside the handle assembly 12. The handle assembly 12 is then used to operate the stapler 10 in three different functions or modes of operation. The first mode allows the user to open and close the jaws 48, 50 of the end effector 18. The second mode fires the staples and the third mode of operation returns the I-beam 32 to its original proximal position following the firing of staples.

Figure 53:
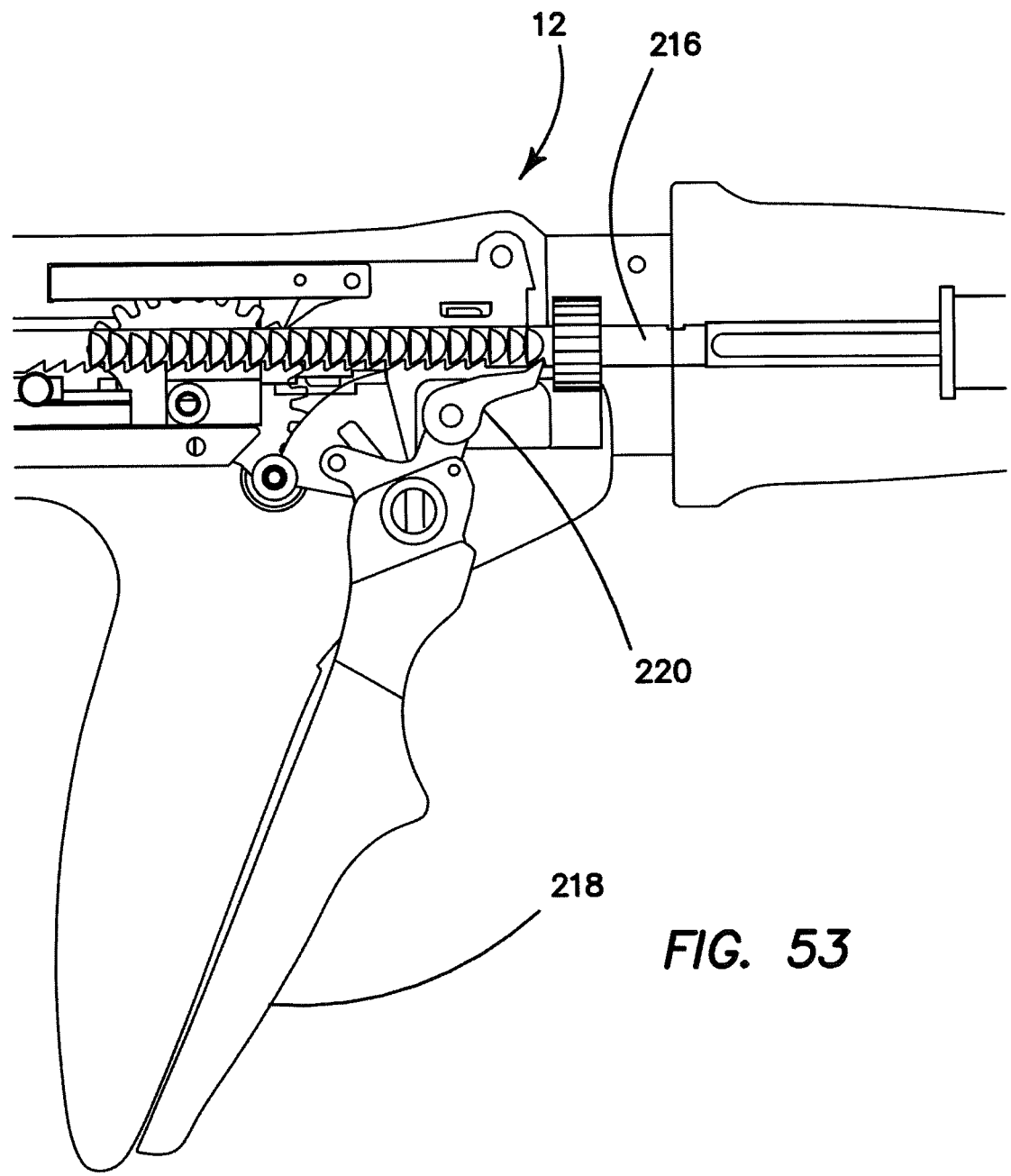
FIG. 53 is a transparent sectional view of a handle assembly according to the present invention.
Figure 54:
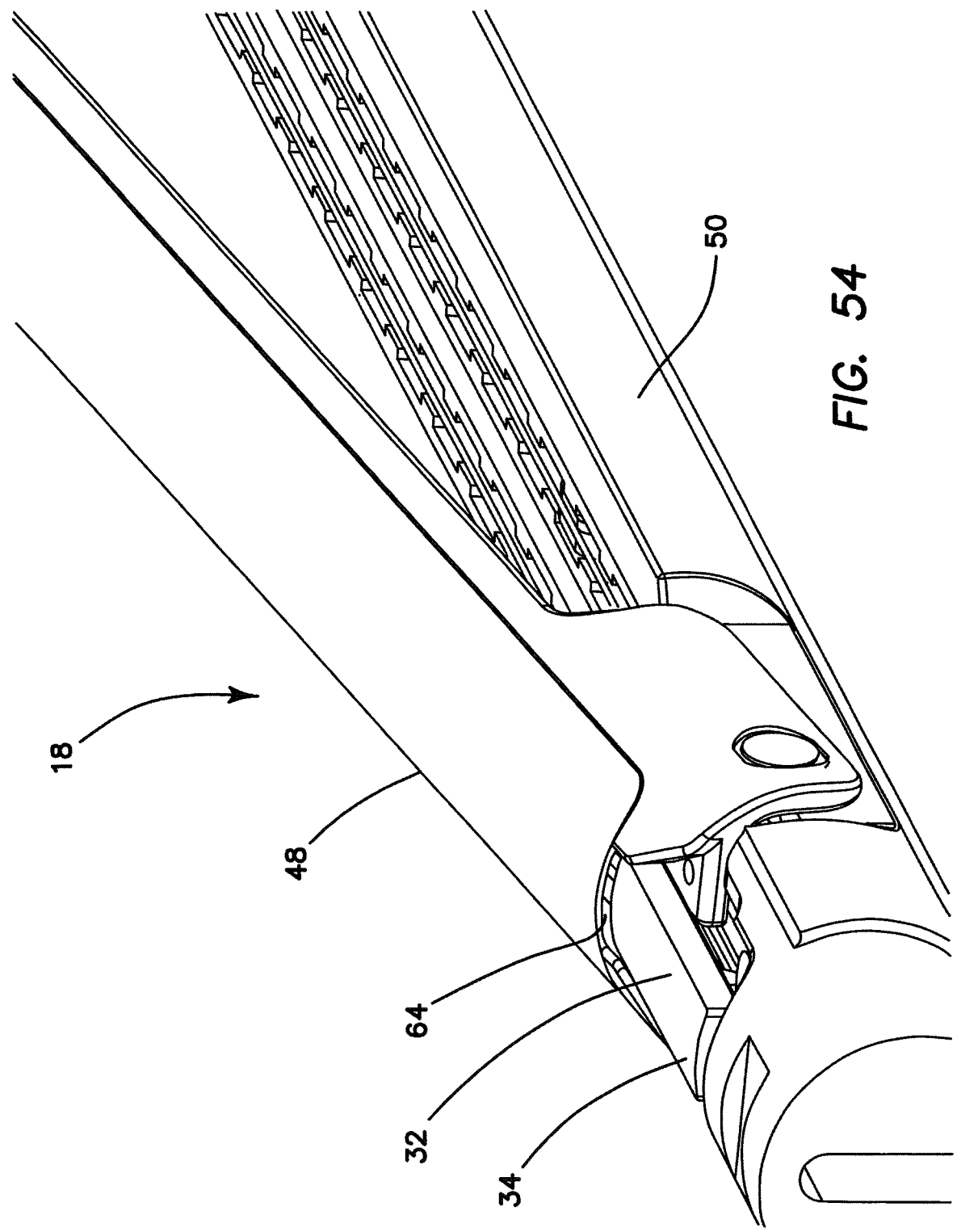
FIG. 54 is a rear top perspective view of an end effector with an upper jaw in an open position according to the present invention.
Figure 55:
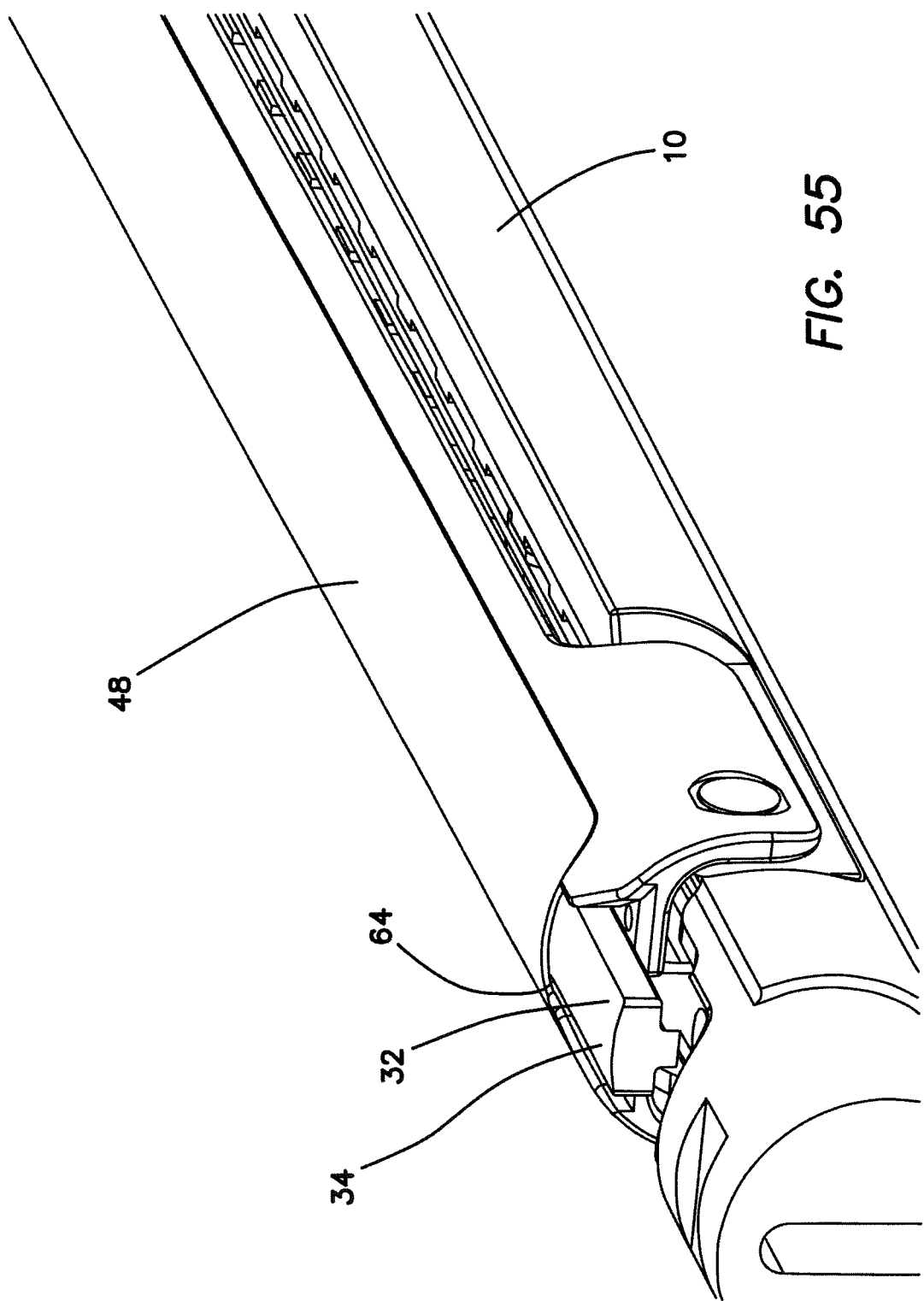
FIG. 55 is a rear top perspective view of an end effector with the upper jaw in a closed position according to the present invention.
Figure 56:
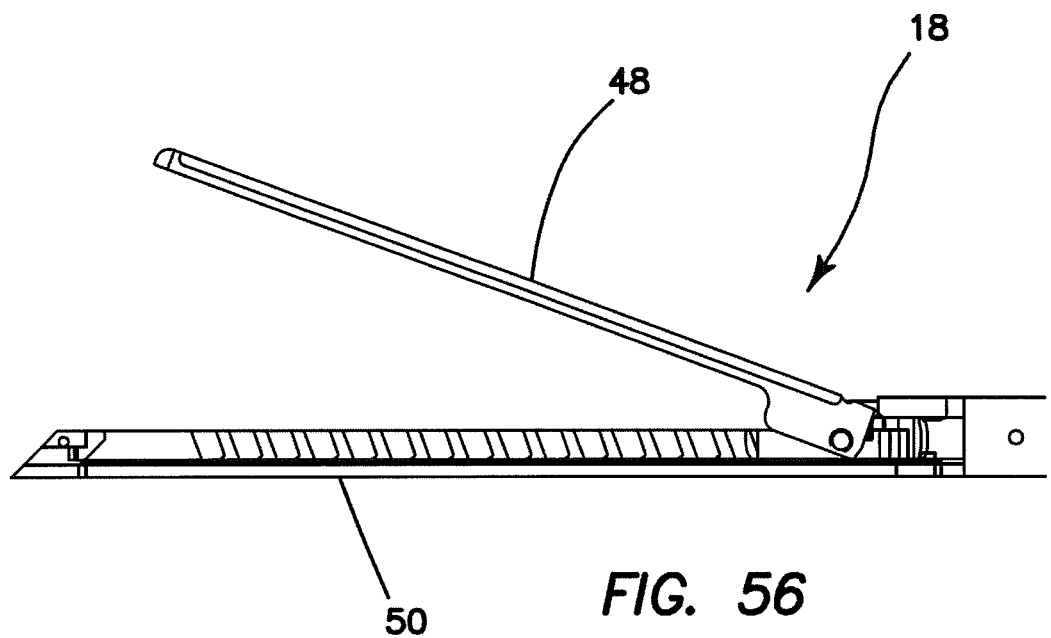
FIG. 56 is a side elevational view of an end effector with an upper jaw in an open position according to the present invention.
Figure 57:
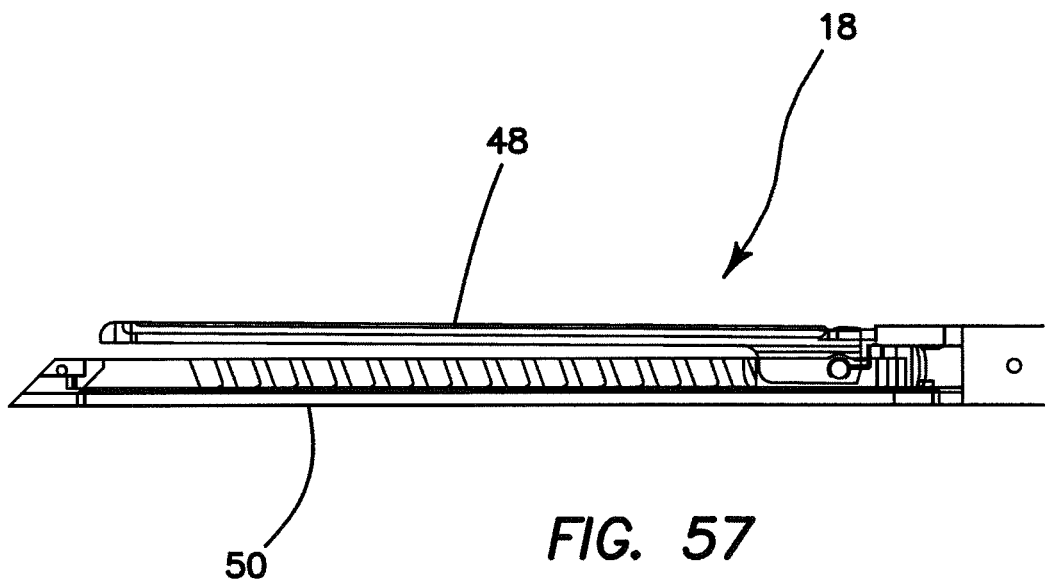
FIG. 57 is a side elevational view of an end effector with an upper jaw in a closed position according to the present invention.

With reference to FIG. 53, the handle 218 is connected to a forward driver 220 which engages a forward tooth on the actuator shaft 216. When the handle 218 is depressed, the actuator 216 is moved slightly forward which in turn moves the actuator shaft 22 of the stapler cartridge assembly 14 forward. Since the actuator shaft 22 is connected to the I-beam 32, the I-beam 32 advances forward with the depression of the handle 218. As the I-beam 32 advances, the beveled front end 40 of the top portion 34 of the I-beam 32 enters the passageway 64 in the upper jaw 48 which deflects the open and spring biased upper jaw 48 downward from an open position to a closed position as shown in FIGS. 54-55. The upper jaw 48 is connected to the lower jaw 50 with a pin such that the upper jaw 48 pivots with respect to the lower jaw 50. Springs (not shown) are included to create a spring bias that urges the upper jaw 48 in an open position with respect to the lower jaw 50. The top portion 34 of the I-beam 32 is shown entering the passageway 64 in FIG. 54 with the jaws biased in an open position. In FIG. 55, the top portion 34 of the I-beam 32 has entered the passageway 64 and moved the upper jaw 48 into a closed orientation with respect to the lower jaw 50. When the handle 218 is released the actuator shafts 216, 22 move proximally pulling the I-beam 32 also proximally allowing the spring bias to open the jaws as the top portion 34 exits the passageway 64. The user can open and close the jaws of the end effector 18 by pressing and releasing the handle 218 to position the targeted tissue between the upper and lower jaws of stapler 10. The end effector 18 is shown in an open position in FIG. 56 and in a closed position in FIG. 57 in which the distance across the gap between the upper jaw 48 and lower jaw 50 is approximately 0.040 inches when in the closed position.

Figure 58:
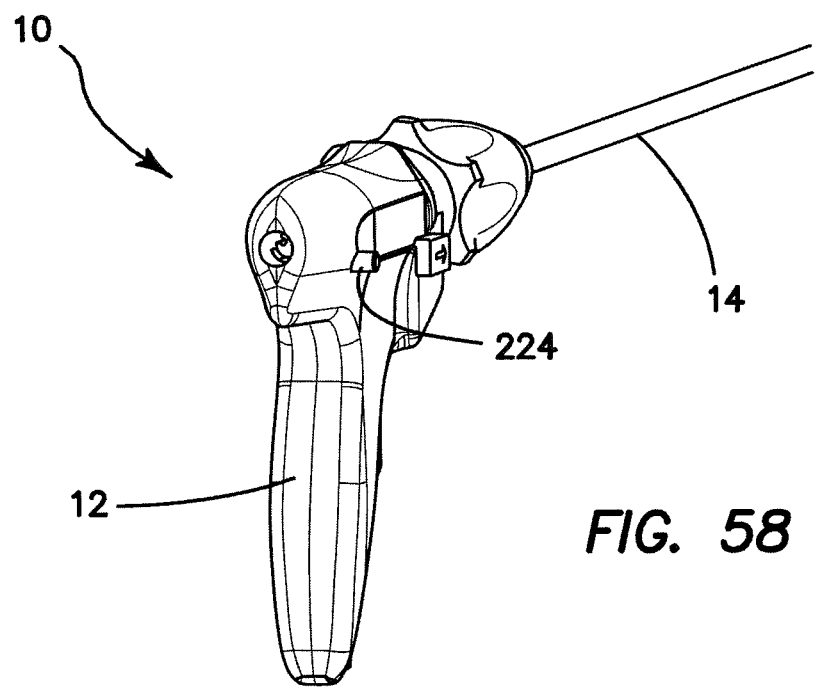
FIG. 58 is a rear, top perspective, sectional view of a surgical stapler according to the present invention.
Figure 59:
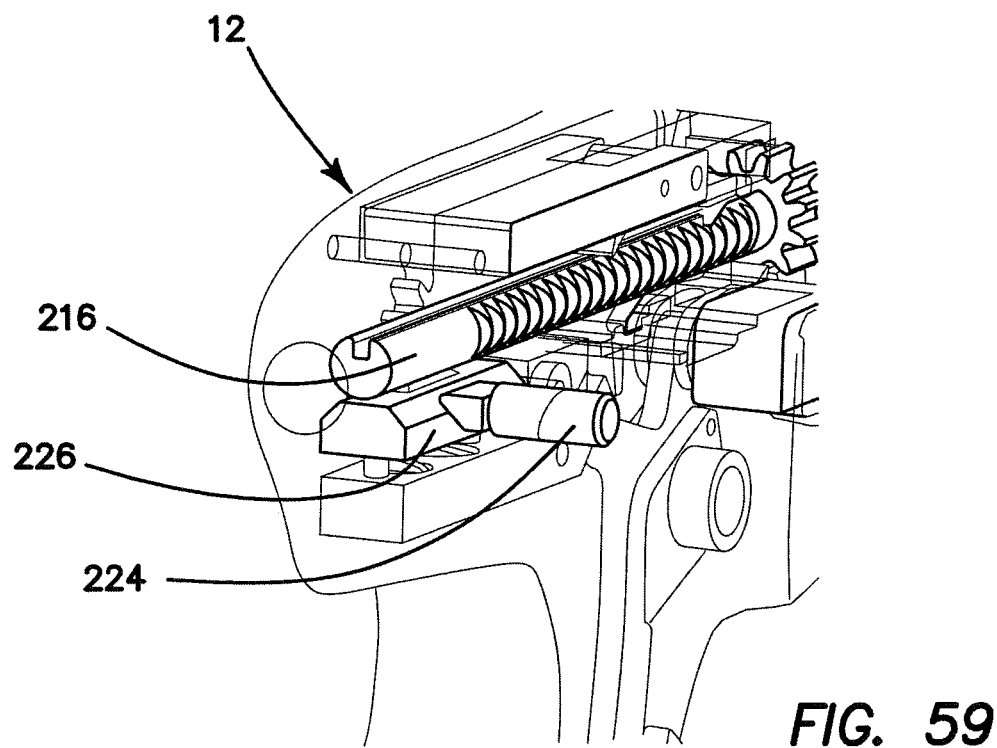
FIG. 59 is a rear, semi-transparent, top perspective, sectional view of a handle assembly according to the present invention.
Figure 60:
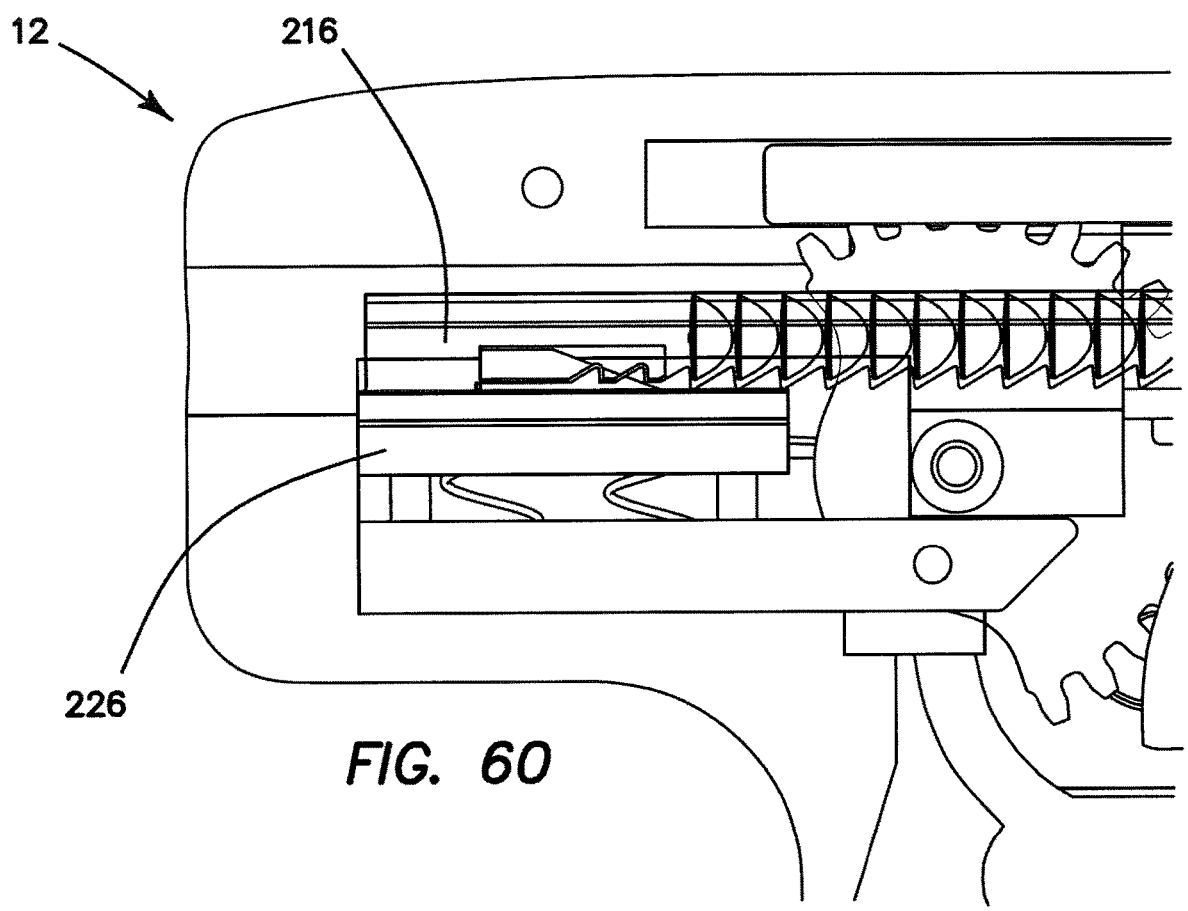
FIG. 60 is a side elevational, sectional view of a handle assembly according to the present invention.

After the jaws are closed in position at the targeted tissue location, the stapler 10 is switched to operate in fire mode by depressing a fire button 224 on the handle assembly 12 as shown in FIG. 58. The fire button 224 disengages an open driver 226 from the actuator shaft 216 as shown in FIGS. 59-60 freeing it for longitudinal movement. The open driver 226 is shown engaged with the teeth of the actuator shaft 216 in FIG. 60. In FIG. 59, the open driver 226 is shown disengaged from the teeth of the actuator shaft 216 with the fire button 224 depressed. With the open driver 226 disengaged, the trigger handle 218 swings out and the forward driver 220 engages with forward teeth on the actuator 216. Depressing the handle 218 advances the actuator shaft 216 forward as the forward driver 220 freely engages teeth with each squeeze of the trigger handle 218. The handle 218 is squeezed multiple times to advance the I-beam 32 all the way to the distal end of the cartridge 52. The handle assembly 14 may also include a rotatable rack described in co-pending U.S. Provisional Patent Application entitled "Surgical stapler having actuation mechanism with rotatable shaft" incorporated herein by reference in its entirety.

Turning now to FIG. 61, there is shown the end effector 18 with the jaws 48, 50 in a closed position. As the I-beam 32 is advanced distally, the top portion 34 of the I-beam 32 travels in the upper passageway 64 and the bottom portion 36 of the I-beam 32 enters the slot 148 of the slider 56 engaging with the slider 56 and pushing it distally. As the angled caming surface 150 leads, it contacts staples (not shown) to urge them out of staple holding locations 92. The blade 42 of the I-beam 32 resides in the gap 228 between the upper jaw 48 and the lower jaw 50 cutting tissue captured between the jaws in between tissue resolved with two or more rows of staples on either side of the blade 42.

Figure 62:
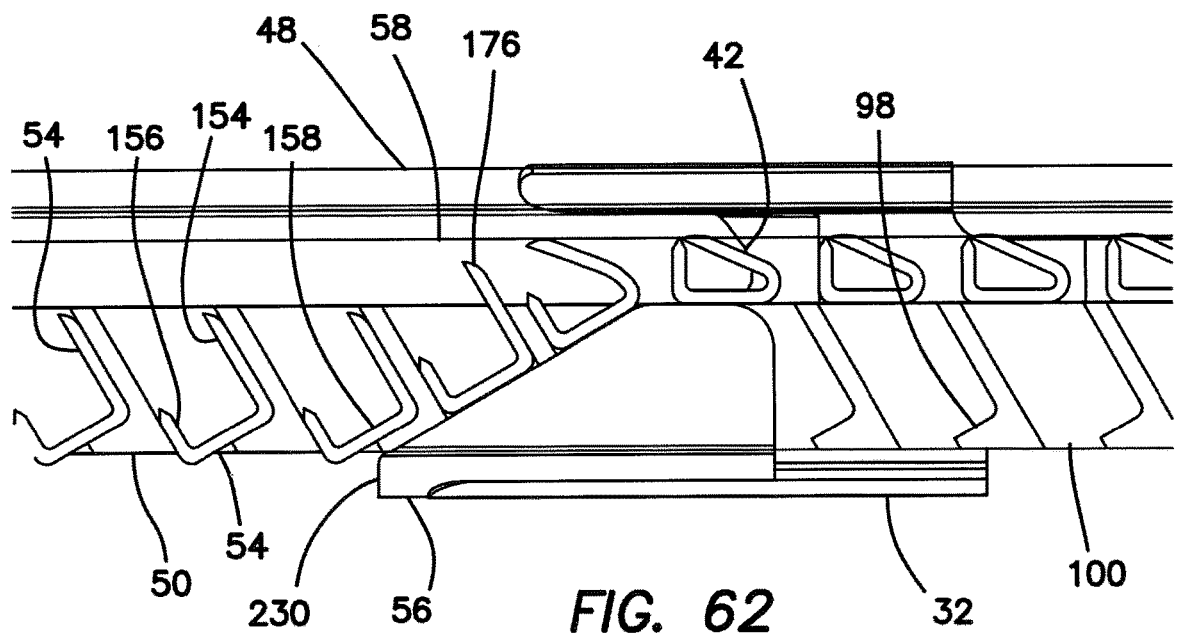
FIG. 62 is a semi-transparent, side elevational, sectional view of an end effector according to the present invention.
Figure 63:
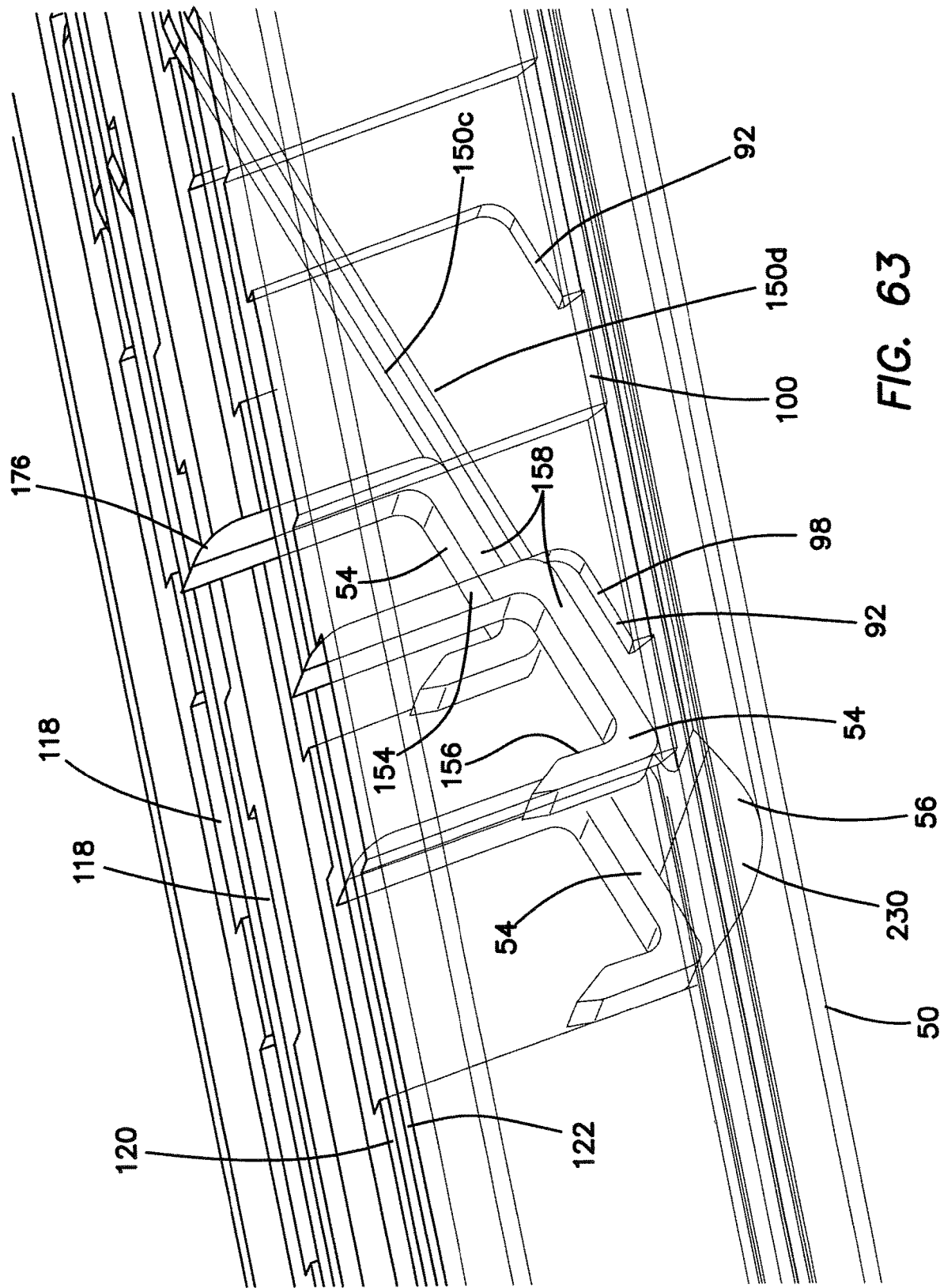
FIG. 63 is a semi-transparent, top perspective, sectional view of an end effector according to the present invention.

FIGS. 62-63 illustrate the deployment of staples 54 as the slider 56 and I-beam 32 advance in the distal direction. The staples 54 are disposed inside staple pockets 118 such that at least a portion of the staple 54 rests against U-shaped staple holding locations 92 such that the longer first leg 154 is located proximally relative to the shorter second leg 156. As the slider 56 advances, the angled caming surfaces 150 sequentially contact the staples. In one variation, a beveled front end 230 of the slider 56 contacts that portion of the outer surface 166 of the staple 54 such as the base 158 of the staple 54 that is in the gap 100 in the bottom wall 98 of the U-shaped staple holding location 92 and urges the staple 54 upwardly. As the slider 56 advances the angled caming surfaces 150 of the slider 56 contact the staples 54 and continue to urge them sequentially upwardly with distal translation of the slider 56. With sufficient deployment height, the longer first leg 154 of the staple 54 contacts the flat anvil surface 58 of the upper jaw 48. In particular, the first tip 176 contacts the flat anvil surface 58. Because the first tip 176 includes a curved, chamfered or beveled outer surface 166, contact of this curved outer surface with the flat anvil surface 58 assists in bending the first leg 154 towards the second leg 156. The curved outer surface 166 of the first tip 176 slides against the flat anvil surface 58 as the first leg 154 bends into a closed triangular configuration. The shorter second leg 156 is not bent or deformed. Unlike a conventional staple, which is fired with the staple legs perpendicular to the forming anvil, the staple of the present invention is fired at an angle with respect to a flat anvil surface 58. There are no staple forming pockets in the anvil surface of the present invention. As the long leg 154 contacts the flat anvil surface 58, the tip 176 of the long leg 154 slides freely along the anvil surface while the staple 54 is progressively pushed normal to the staple base 158 because the staple is at the same angle as the angled caming surface 150 of the slider 56 until the tip 176 of the long leg 154 meets the tip of the shorter second leg 156 and the staple is closed capturing tissue inside the triangular shaped closure. The closure force of the staple 54 of the present invention is advantageously relatively low when compared to conventional staples because only one leg is being deformed, the longer first leg 154; whereas, in conventional staplers, both legs of a staple are deformed simultaneously. Furthermore, closure forces are further reduced by the fact that the long leg is simply being bent over as opposed to being forced to buckle against an anvil pocket. Buckling forces of a beam are much greater than bending forces and conventional staples require the buckling of two staple legs simultaneously. Conventional stapling devices require high firing forces to apply the staple lines. The staple legs are forced perpendicular to the anvil pockets forcing them to buckle. These high forces apply significant stresses to the device components and can cause fatigue for the user. Therefore, the present stapler 10 greatly reduces forces required to deploy and deform staples. The staple forming forces of the present invention are relatively low when compared with conventional staple designs. Since only a single leg bends over in contact with the anvil surface, the user and device is benefited through reduced stresses on the components and reduced actuation forces for the user.

The staple deployment method of the present invention drives a slanted slider down the jaws of the stapling device. The slider 56 comes in direct contact with the staples 54 as it passes through the same space as the staples being deployed. The staples are partially held in place by pockets 118 in the interior jaws or cartridge 52 of the device. These pockets provide guidance for the staples as they are pushed out of the device and formed into tissue. The staples are held in the cartridge in such a way that only part of the staple thickness is resting in a pocket while the other part is in an open channel that is coplanar with the slider 56. One side of the staple is held against the first plate inside staple receiving locations 92 while the other side of the staple is held against the smooth wall of the second plate or, alternatively, in staple holding locations 124 also formed in the second plate. Each slider caming surface 150 travels down the center of the staple in each slot 120, 122. As the slider 56 is pushed distally along the length of the jaw, the angled slider ramp drives the staples out of the guided cartridge pockets. The angled caming surface 150 of the slider pushes normal to the staple base 158. The slider only contacts a part of the staple, while the remaining part of the staple is held against the staple holding locations 92 which serve as guides directing the staple out of the cartridge.

Figure 64:
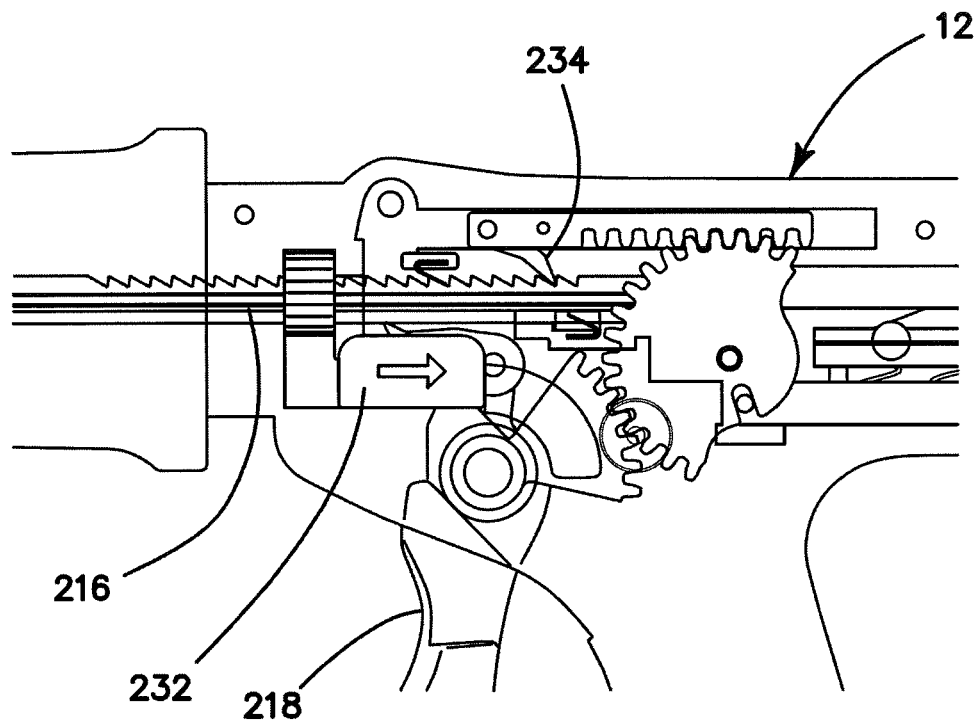
FIG. 64 is a semi-transparent, side elevational, sectional view of a handle assembly according to the present invention.
Figure 65:
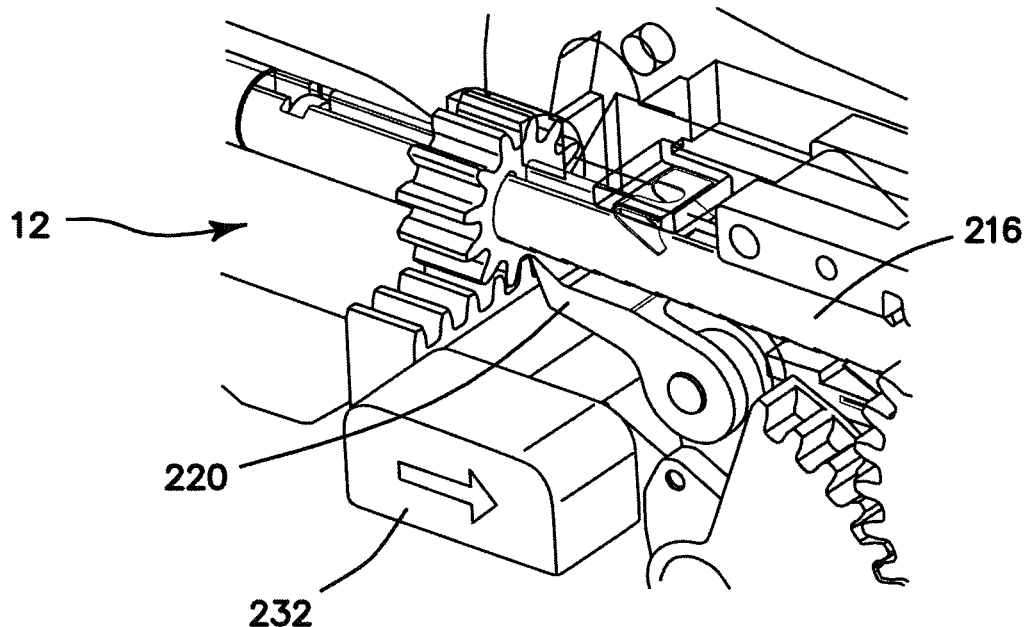
FIG. 65 is a semi-transparent, top perspective, sectional view of a handle assembly according to the present invention.
Figure 66:
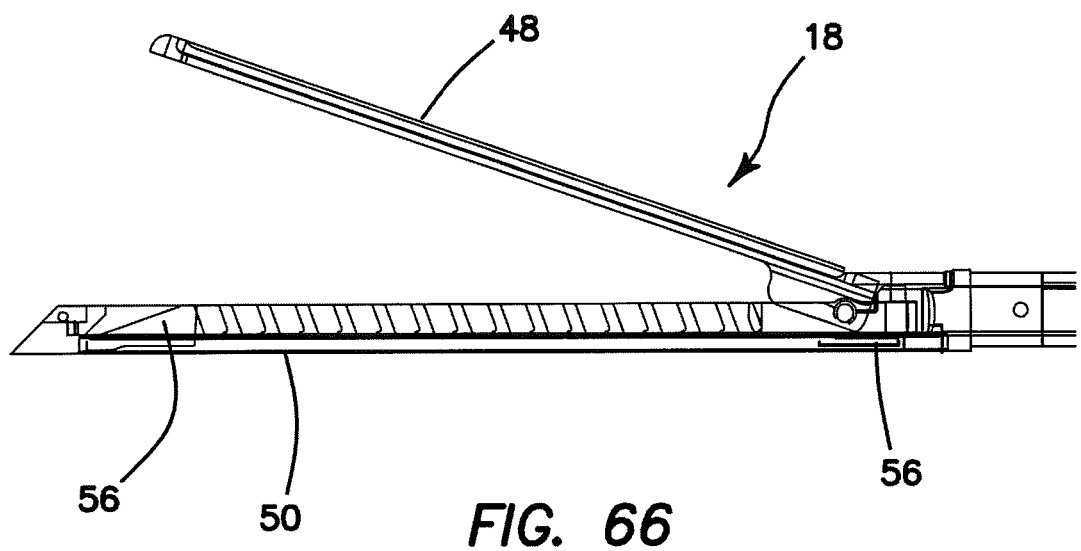
FIG. 66 is a semi-transparent, side elevational view of an end effector with an upper jaw in an open position according to the present invention.

Turning now to FIGS. 64-65, after the staples are fired, the handle assembly 12 is switched into the third mode of operation in which the I-beam 32 is returned proximally to its starting position. A gear switch button 232 is depressed which rotates the actuator shaft 216 90 degrees so that the reverse teeth on the actuator 216 come into contact with the reverse driver 234. The reverse driver 234 is connected to the handle 218 by a series of gears. When the handle 218 is squeezed, the reverse driver 234 pulls the actuator 216 and I-beam 32 back. The trigger handle 218 is squeezed multiple times to return the I-beam 32 to its original position. The I-beam 32 is returned to its original proximal position to open the jaws 48, 50. With the I-beam 32 returned, the slider 56 is left in its distal fired position. FIG. 66 illustrates, the I-beam 32 returned and fully retracted resulting in the spring biased upper jaw 48 becoming open while the slider 56 is left in its distal location allowing the stapled tissue to be released from the jaws. When the actuator 216 and I-beam 32 is returned, the stapler cartridge assembly 14 can be detached from the handle assembly 12 and new stapler cartridge assembly 14 can be attached to continue stapling.

Figure 67:
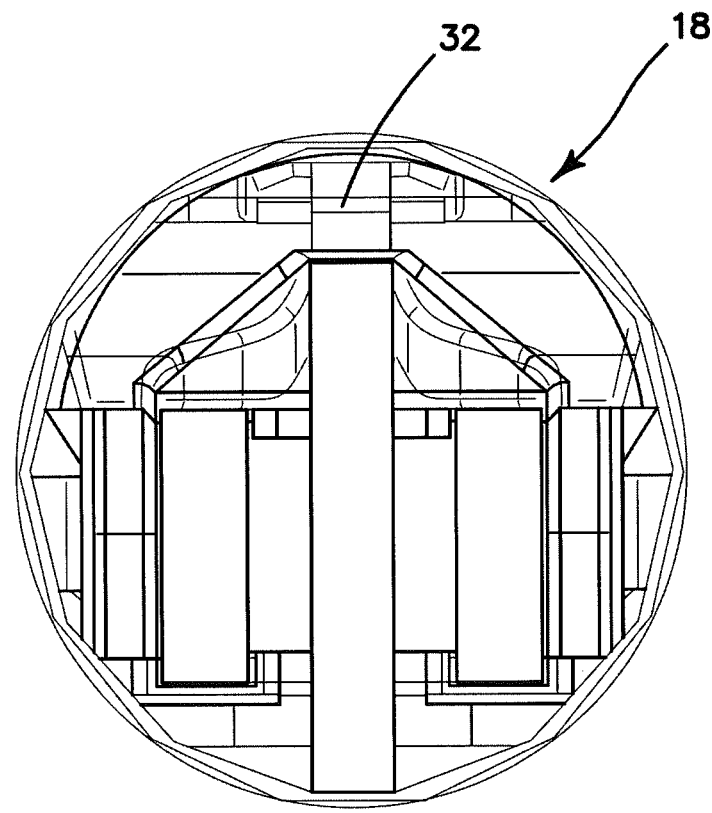
FIG. 67 is a semi-transparent end view of an end effector according to the present invention.

The conventional laparoscopic stapler is currently approximately 12 millimeters in diameter which requires a larger sized cannula for insertion and, hence, a larger incision in the patient. The laparoscopic stapler 10 of the present invention has a diameter of approximately 0.271 inches as shown in FIG. 67 which will advantageously fit inside smaller diameter cannulas that require smaller incisions in the patient. The smaller incision results in less pain, faster patient recovery times and a smaller scar visible after the operation. FIG. 67 illustrates that the I-beam 32 substantially defines the diameter of the end effector 18. Approximately a little less than half the diameter of the device is consumed with the upper jaw and gap between the upper and lower jaw leaving approximately half the diameter of the device, approximately 0.130 inches for housing the staples and mechanisms for staple deployment including the slider.

The problem presented in traditional staplers is that they require larger diameters and larger incisions as well as higher firing forces in order to deploy staples. This is due to the fact that traditional staples require a pusher to deploy staples. The pusher is an intermediate caming surface disposed between each staple and the slider. Typically, each pusher is of equal height as the staple and resides directly below the staple. The height of the pusher has to be approximately equal to the height of the staple in order to fully urge the staple out of the staple pockets and into the gap between the upper and lower jaws. The pusher typically includes an angled lower surface that cams against an angled slider. The upper surface of the pusher is typically flat and horizontal and cams normal to the base of the staple. In essence, the pusher takes up valuable space when trying to achieve a smaller stapler that will fit in a smaller sized cannula which is typically called a 5 millimeter cannula. The present invention successfully eliminates the pusher altogether due to the angled positioning of the staple such that the base of the staple is parallel to the angled caming surface of the slider. Because the staple of the present invention is placed at an angle, the horizontally traveling slider comes in direct contact with the staple during deployment without having any additional pusher between the staple and slider. Because there is no pusher required in the present invention, a great deal of space is saved resulting in a much smaller diameter device.

It is not just a matter of reducing staple size but also effectively deploying staples that form a closed staple configuration capable of holding tissue in a manner that is just as strong as a conventional stapler and doing so in a reliable and repeatable manner that is an important factor achieved by the stapler of the present invention. Another problem of conventional staplers that the present invention addresses and successfully avoids pertains to the anvil surface. Traditional anvil surfaces include detailed anvil pockets formed in the anvil surface. These anvil surface formations are necessary in order to reliably and repeatedly form staples in conventional staplers. The anvil surface is especially important as traditional staples are placed normal to the anvil surface and without anvil surface formations to guide the buckling staple legs the staple legs would splay in any direction and not form a nice closure important for securing tissue. Furthermore, the anvil pockets of traditional staplers require that the anvil of the upper jaw be perfectly aligned with the staple pockets and in particular, the staples residing in the pockets in order to effect perfect staple formation. Anvil surface formations or pockets are a necessity for staple formation reliability; however, they also increase manufacturing costs that result from not only forming detailed surface formation but also in making sure the anvil surface formations are in alignment with the staple trajectory. The present invention advantageously eliminates anvil surface formations and provides a smooth, flat anvil surface against which the staple legs are deformed. Typically, without anvil surface formations the staple legs would splay in any direction and not form a perfect closure. However, the present invention provides for angled staple holding locations that hold the staple at an angle with respect to the anvil surface. Furthermore, the staple has one longer leg and a shorter leg. As a result of this design, as the staple is ejected from the lower jaw, it is the longer leg that leads staple ejection. Because the longer leg leads, this leg will be the first leg to contact the anvil surface and instead of splaying in any direction the first leg is reliably bent towards the second leg. Misalignment of staple tips is eliminated because as the longer leg is being deformed against the flat anvil surface the remaining portion of the staple including the shorter leg remains substantially contained and guided in the staple pocket or staple holding location and prevented from lateral displacement that would result in a malformed staple. Also, the tip of the longer leg is curved or chamfered which provides a predilection for the staple to bend towards the second leg. Also, the curved tip allows the tip of the longer leg to slide against the smooth anvil surface as the longer leg of the staple is being deformed. Hence, the present invention not only reduces the overall diameter of the end effector, it also does so without sacrificing staple formation repeatability and reliability.

The problem of fitting a surgical stapler into a 5 mm cannula is solved by the absence of intermediate caming portions that are also known as "pushers" located between the slider and the staple. Typically, the legs of a staple are located in receiving pockets such that they are perpendicular to the anvil. The angled slider contacts the pushers which then contact the staple to drive it out of the staple pocket. Without an intermediate caming portion or pusher, the slider would have to contact the staple directly risking angular forces upon the staple that would angulate the staple legs out of alignment with the anvil surface formations resulting in malformed staples or angulate the staple legs with respect to the pocket resulting in the staple jamming against the pocket. Typically, the staples are stacked above the pushers. Therefore, removal of pushers saves tremendous space in the design and angled staples contact an angled slider directly. The elimination of pushers also further reduces manufacturing costs as the number of components is reduced and eases manufacturing as pushers are no longer required to be assembled. The angled orientation of the staples themselves is also a tremendous space saver as opposed to the staples being vertically oriented as in traditional staplers. Since there is no target pocket or anvil surface formation for the staple legs to come into contact with, the reliability of staple formation is greatly improved as the staple is free to deform against a smooth anvil surface without risking misalignment with anvil pockets as in traditional staplers. Valuable space is also saved by the slider moving through the same space or slots in which the staples reside.

Figure 68:
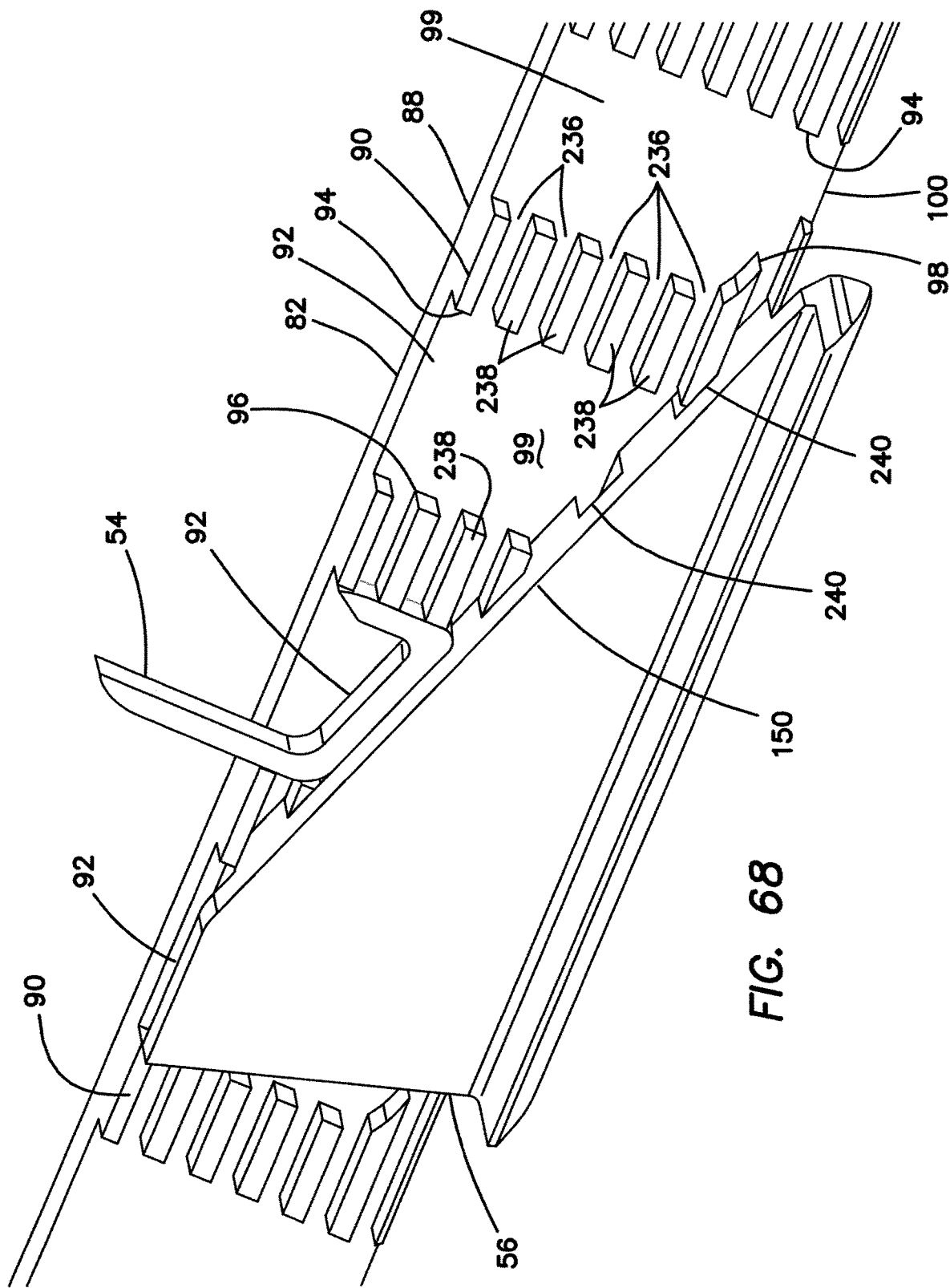
FIG. 68 is a top perspective, sectional view of a plate, slider and staple according to the present invention.

Turning now to FIG. 68, there is shown another variation of a staple cartridge 52 similar to that described above with respect to FIGS. 17-21 wherein like numbers are used to describe like parts. As described above, the cartridge 52 comprises at least two plates sandwiched together to form a single row of staple receiving pockets with additional plates added to increase the desired number of staple rows. The outer surface 88 of the first plate 82 is smooth and the inner surface 90 is formed with a plurality of staple holding locations 92. The staple holding locations 92 are recesses formed in the inner surface 90 of the first plate 82. Each staple holding location 92 is substantially U-shaped and defined by a front sidewall 94 formed oppositely and substantially parallel to a rear sidewall 96. The rear sidewall 96 is interconnected to a bottom wall 98 forming an L-shaped wall defining a gap 100 between the bottom wall 98 and the front sidewall 94. In one variation, no gap 100 is formed. Instead, the bottom wall 98 interconnects with both the front sidewall 94 and rear sidewall 96 to form a complete U-shaped staple holding location 92. The U-shaped staple holding locations are angled approximately 30-90 degrees with 90 degrees being a vertical non-angled orientation. FIG. 68 illustrates the U-shaped staple holding location being at 90 degrees or substantially perpendicular. The recessed wall 99 is recessed with respect to the inner surface 90. Segments of the inner surface 90 that are located between the staple holding locations 92 include a plurality of horizontal grooves 236 that extend between the staple receiving locations 92. The grooves 236 are rectangular and have square or rectangular cross-sections. The grooves 236 have a depth equal to the depth of the recessed wall 99. The grooves 236 are separated by lands 238 that constitute the inner surface 90 and therefore are equal in height to the inner surface 90. The grooves 236 stretch across the entire length of the first plate intersecting each sidewall 94, 96 and bottom wall 98 of the staple holding locations 92. The staple holding locations 92 are configured for partially receiving and holding a complementary, substantially U-shaped staple that is thicker than the thickness of the grooved sidewalls 94, 96, 98. In one variation, the staple holding locations 92 receive the entire thickness of a complementarily U-shaped staple as shown in FIG. 68 such that no portion of the staple 54 resides outside the staple holding location 92. The slider 56 includes an angled caming surface 150 with a side surface that is also formed with a plurality of horizontal grooves 240 forming channels for receiving the upstanding lands 238 that are located between staple holding locations 92. A second plate 84 or shim is not shown in FIG. 68 but together with the first plate 84 define a slot 120 therebetween inside which the angled caming surface 150 of the slider 56 is capable of translating interconnected on the side surface with interlocked grooves 240 and lands 238. Because a staple 54 is resident in a grooved staple receiving portion 92, the angled caming surface 150 of the slider 56 is still able to contact the outer surface 166 of the staple 54 as the angled caming surface 150 translates through the grooves 236 to urge staple 54 upwardly and out. The grooved inner surface 90 of the first plate 82 advantageously allows the use of very thin staples; for example, staples that are the same depth as the staple pocket depth or depth of the staple holding location 92. The depth of the staple pocket is approximately 0.0085 inches which is also the thickness of the staple 54 that can be used in this variation of the invention. Therefore, the grooved plate 82 not only allows for extremely thin staples, it further reduces the size of the staple or allows additional space for structures that make the end effector stronger.

The stapler of the present invention is particularly suited for laparoscopic procedures; however, the invention is not so limited and the stapler of the present invention can be used in open surgical procedures equally effectively. In laparoscopic procedures, the stapler of the present invention can be used, for example, for the closure and anastomosis of tissue such as colon, small intestines, and stomach.

It is understood that various modifications may be made to the embodiments of the surgical stapler disclosed herein. Therefore, the above description should not be construed as limiting, but merely as exemplifications of preferred embodiments. Those skilled in the art will envision other modifications within the scope and spirit of the present disclosure.

We claim:

1. A surgical stapler comprising:
a handle assembly;
a cartridge assembly connected to the handle assembly; the cartridge assembly having a proximal end and a distal end and a jaw assembly at the distal end; the jaw assembly includes a first jaw connected to a second jaw; the first jaw has an anvil surface and the second jaw has a top surface; the first jaw is connected to the second jaw such that the second jaw is movable relative to the first jaw; the jaw assembly includes a closed position in which the anvil surface is adjacent to the top surface and a gap is defined between the top surface and the anvil surface; the second jaw includes a first surface and a second surface parallel to each other and perpendicular to the top surface; the first surface includes a plurality of recesses formed into the first surface; each recess has a recessed wall, a front sidewall, a rear sidewall and a bottom wall; the second jaw includes a plurality of staple pockets; each staple pocket is defined by each recess including an opening to the top surface of the second jaw; the first surface includes a plurality of longitudinally extending grooves formed into the first surface; the surgical stapler further includes an actuator coupled to the handle assembly and a first caming surface movable by the actuator; the first caming surface includes a plurality of projections sized and configured to fit within the longitudinally extending grooves of the first surface and translate therein; the first caming surface is movable by the actuator along a length of the second jaw; and a plurality of staples positioned in the plurality of staple pockets; each staple has a staple width and is positioned within and supported by a staple pocket;

wherein, with translation of the first caming surface along the jaw assembly, the projections of the first caming surface are sized and configured to pass through one or more staple pockets making contact with a portion of the staple width to urge the staple out of the opening and against the anvil surface.

2. The surgical stapler of claim 1 further including a gap defined between the bottom wall and the front sidewall.

3. The surgical stapler of claim 1 wherein the grooves have a depth equal to a depth of the recessed wall.

4. The surgical stapler of claim 1 wherein the grooves are separated by lands that constitute the first surface.

* * * * *